(12) United States Patent
Bentley et al.

(10) Patent No.: US 9,475,820 B2
(45) Date of Patent: Oct. 25, 2016

(54) SUBSTITUTED IMIDAZO[1,2-A]PYRAZINES AS TNF ACTIVITY MODULATORS

(71) Applicant: UCB Biopharma SPRL, Brussels (BE)

(72) Inventors: Jonathan Mark Bentley, Abingdon (GB); Daniel Christopher Brookings, Slough (GB); Julien Alistair Brown, Slough (GB); Thomas Paul Cain, Abingdon (GB); Laura Jane Gleave, Abingdon (GB); Alexander Heifetz, Abingdon (GB); Victoria Elizabeth Jackson, Slough (GB); Craig Johnstone, Abingdon (GB); Deborah Leigh, Abingdon (GB); James Madden, Abingdon (GB); John Robert Porter, Slough (GB); Matthew Duncan Selby, Slough (GB); Zhaoning Zhu, Slough (GB)

(73) Assignee: UCB Biopharma SPRL, Brussels (BE)

( * ) Notice: Subject to any disclaimer, the term of this patent is extended or adjusted under 35 U.S.C. 154(b) by 144 days.

(21) Appl. No.: 14/414,299

(22) PCT Filed: Jul. 5, 2013

(86) PCT No.: PCT/EP2013/064332
§ 371 (c)(1),
(2) Date: Jan. 12, 2015

(87) PCT Pub. No.: WO2014/009296
PCT Pub. Date: Jan. 16, 2014

(65) Prior Publication Data
US 2015/0191482 A1    Jul. 9, 2015

(30) Foreign Application Priority Data
Jul. 13, 2012    (GB) .................. 1212513.4

(51) Int. Cl.
| | |
|---|---|
| A61K 31/4985 | (2006.01) |
| C07D 241/36 | (2006.01) |
| C07D 491/107 | (2006.01) |
| C07D 487/04 | (2006.01) |
| A61K 31/506 | (2006.01) |
| A61K 31/5377 | (2006.01) |
| A61K 31/5513 | (2006.01) |
| C07D 451/02 | (2006.01) |
| C07D 471/08 | (2006.01) |

(52) U.S. Cl.
CPC ....... *C07D 491/107* (2013.01); *A61K 31/4985* (2013.01); *A61K 31/506* (2013.01); *A61K 31/5377* (2013.01); *A61K 31/5513* (2013.01); *C07D 451/02* (2013.01); *C07D 471/08* (2013.01); *C07D 487/04* (2013.01)

(58) Field of Classification Search
CPC .................. A61K 31/4985; C07D 241/36

USPC ......... 514/249; 540/575; 544/117, 333, 350, 544/359; 546/199, 268.1; 548/202, 250, 548/373.1, 469, 518; 549/13, 356
See application file for complete search history.

(56) References Cited

U.S. PATENT DOCUMENTS

| | | | |
|---|---|---|---|
| 2004/0220189 A1 | 11/2004 | Sun et al. | |
| 2005/0009832 A1 | 1/2005 | Sun et al. | |

FOREIGN PATENT DOCUMENTS

| | | |
|---|---|---|
| WO | 01/64674 A1 | 9/2001 |
| WO | 2011/022439 A1 | 2/2011 |
| WO | 2011/100502 A1 | 8/2011 |
| WO | 2013/034048 A1 | 3/2013 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Hackam, et al. JAMA, 296(14), 2006, 1731-1732.*
Matthews, et al. Bioorganic & Medicinal Chemistry Letters, 20(14), 2010, 4045-4049.*
Myadaraboina, et al. European Journal of Medicinal Chemistry, 45(11), 2010, 5208-5216.*
Matthews et al., "Design and evaluation of 3,6-di(hetero)aryl imidazo[1,2-a]pyrazines as inhibitors of checkpoint and other kinases", Bioorganic & Medicinal Chemistry Letters, Jul. 2010, 20(14), 4045-4049.
Lyon et al., "Glyoxylic Acid and MP-Glyoxylate: Efficient Formaldehyde Equivalents in the 3-CC of 2-Aminoazines, Aldehydes, and Isonitriles", Organic Letters, Dec. 2004, 6(26), 4989-4992.

(Continued)

*Primary Examiner* — Douglas M Willis
(74) *Attorney, Agent, or Firm* — McDonnell Boehnen Hulbert & Berghoff LLP

(57) ABSTRACT

A series of imidazo[1,2-a]pyrazine derivatives, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders. The imidazo[1,2-a]pyrazine derivatives of the disclosure are of general formula

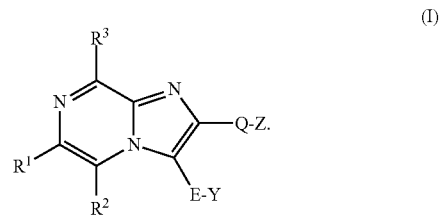

14 Claims, No Drawings

(56) References Cited

OTHER PUBLICATIONS

Maccoss et al., "Synthesis and Biological Evaluation of Nucleosides Containing 8-Amino-imidazo[1,2-a]pyrazine as an Isosteric Replacement for Adenine", Journal of Heterocyclic Chemistry, Oct. 1993, 30(5), 1213-1220.

Guchhait et al., "C-H Bond Functionalization under Metalation-Deprotonation Process: Regioselective Direct Arylation of 3-Aminoimidazo[1,2-a]pyrazine", The Journal of Organic Chemistry, Sep. 2012, 77(18), 8321-8328.

Caballero et al., "Docking and quantitative structure-activity relationship studies for imidazo[1,2-a]pyrazines as inhibitors of checkpoint kinase-1", Medicinal Chemistry Research, 2012, 21(8), 1912-1920.

Tansey et al., "The TNF superfamily in 2009: new pathways, new indications, and new drugs", Drug Discovery Today, Dec. 2009, 14(23/24), 1082-1088.

Carneiro et al., "Emerging Role for TNF-alpha in Erectile Dysfunction", J. Sexual Medicine, Dec. 2010, vol. 7, 3823-3834.

* cited by examiner

SUBSTITUTED IMIDAZO[1,2-A]PYRAZINES AS TNF ACTIVITY MODULATORS

CROSS-REFERENCE TO RELATED APPLICATIONS

This application is a US national phase of International Application No. PCT/EP2013/064332 filed on Jul. 5, 2013, which claims priority to Great Britain Patent Application No. 1212513.4 filed on Jul. 13, 2012.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to a class of fused imidazole derivatives, and to their use in therapy. More particularly, this invention is concerned with pharmacologically active substituted imidazo[1,2-α]pyrazine derivatives. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

(2) Description of Related Art (Including Information Disclosed Under 37 CFR 1.97 and 1.98)

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certulizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

BRIEF SUMMARY OF THE INVENTION

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

The compounds in accordance with the present invention potently neutralise the activity of TNFα in a commercially available HEK-293 derived reporter cell line known as HEK-Blue™ CD40L. This cell line is a stable transfectant expressing SEAP (secreted alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, the compounds of the present invention exhibit an $IC_{50}$ value of 50 µM or less, generally of 20 µM or less, usually of 5 µM or less, typically of 1 µM or less, suitably of 500 nM or less, ideally of 100 nM or less, and preferably of 20 nM or less (the skilled person will appreciate that a lower $IC_{50}$ figure denotes a more active compound).

BRIEF DESCRIPTION OF THE SEVERAL VIEWS OF THE DRAWINGS

Not Applicable

DETAILED DESCRIPTION OF THE INVENTION

The present invention provides a compound of formula (I) or an N-oxide thereof, or a pharmaceutically acceptable salt or solvate thereof, or a glucuronide derivative thereof, or a co-crystal thereof:

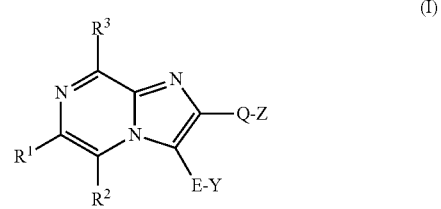

wherein

E represents a covalent bond; or E represents —O—, —S—, —S(O)—, —S(O)$_2$— or —N(R$^4$)—; or E represents an optionally substituted straight or branched C$_{1-4}$ alkylene chain;

Q represents a covalent bond; or Q represents —O—, —S—, —S(O)—, —S(O)$_2$—, —N(R$^5$)—, —C(O)N(R$^5$)—, —N(R$^5$)C(O)—, —S(O)$_2$N(R$^5$)— or —N(R$^5$)S(O)$_2$—; or Q represents an optionally substituted straight or branched C$_{1-6}$ alkylene chain optionally comprising one, two or three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—;

Y represents C$_{3-7}$ cycloalkyl, aryl, C$_{3-7}$ heterocycloalkyl or heteroaryl, any of which groups may be optionally substituted by one or more substituents;

Z represents hydrogen, halogen or trifluoromethyl; or Z represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents;

Z$^1$ represents a divalent radical derived from an aryl, C$_{3-7}$ heterocycloalkyl or heteroaryl group;

Z$^2$ represents aryl, C$_{3-7}$ heterocycloalkyl, C$_{3-7}$ heterocycloalkenyl or heteroaryl;

R$^1$, R$^2$ and R$^3$ independently represent hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, C$_{4-9}$ heterobicycloalkenyl, heteroaryl, heteroaryl(C$_{1-6}$)alkyl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{4-7}$)cycloalkenyl-heteroaryl-, (C$_{3-7}$) heterocyclo alkyl-heteroaryl-, (C$_{3-7}$)heterocycloalkyl (C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents;

R$^4$ and R$^5$ independently represent hydrogen or C$_{1-6}$ alkyl;

R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl (C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$) alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl and propargyl.

Suitable $C_{3-7}$ cycloalkyl groups, which may comprise benzo-fused analogues thereof, include cyclopropyl, cyclobutyl, benzocyclobutenyl, cyclopentyl, indanyl, cyclohexyl and cycloheptyl.

Suitable $C_{4-7}$ cycloalkenyl groups include cyclobutenyl, cyclopentenyl, cyclohexenyl and cycloheptenyl.

Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include azetidinyl, tetrahydrofuranyl, dihydrobenzofuranyl, pyrrolidinyl, indolinyl, oxazolidinyl, thiazolidinyl, imidazolidinyl, tetrahydropyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl, thiomorpholinyl, diazepanyl, thiadiazepanyl and azocanyl. Additional values include oxetanyl, dihydrobenzothienyl, isoindolinyl and isothiazolidinyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

Typical heterobicycloalkyl groups include 3-azabicyclo[3.1.0]hexanyl, 2-oxa-5-azabicyclo[2.2.1]heptanyl, quinuclidinyl, 2-oxa-5-azabicyclo[2.2.2]octanyl, 8-azabicyclo[3.2.1]octanyl, 3,8-diazabicyclo[3.2.1]octanyl and 3,9-diazabicyclo[4.2.1]nonanyl. Additional values include 6-azabicyclo[3.2.0]heptanyl, 3-azabicyclo[4.1.0]heptanyl, 3-azabicyclo[3.2.1]octanyl and 3,6-diazabicyclo[3.2.2]nonanyl.

Typical heterobicycloalkenyl groups include 8-azabicyclo[3.2.1]octenyl.

Suitable spiroheterocycloalkyl groups include 2-oxa-6-azaspiro[3.3]heptanyl, 2-oxa-6-azaspiro[3.4]octanyl, 2-oxa-6-azaspiro[3.5]nonanyl and 2-oxa-7-azaspiro[3.5]-nonanyl. Additional values include 2-azaspiro[3.3]heptanyl, 5-azaspiro[2.4]heptanyl and 7-oxa-2-azaspiro[3.5]nonanyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups. Additional values include thieno[2,3-c]pyrazolyl, thieno[3,4-b][1,4]dioxinyl, pyrrolo[3,4-b]pyridinyl and imidazo[2,1-b]thiazolyl.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2$C=O) ↔ enol (CH=CHOH) tautomers or amide (NHC=O) ↔ hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one aspect, the present invention provides a compound of formula (I) as depicted above or an N-oxide thereof, or a pharmaceutically acceptable salt or solvate thereof, or a glucuronide derivative thereof, or a co-crystal thereof, wherein Q represents —O—, —S—, —S(O)—, —S(O)$_2$—, —N(R$^5$)—, —C(O)N(R$^5$)—, —N(R$^5$)C(O)—, —S(O)$_2$N(R$^5$)— or —N(R$^5$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—;

Z represents $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents; and E, Y, R$^1$, R$^2$, R$^3$, R$^5$, Z$^1$ and Z$^2$ are as defined above.

In another aspect, the present invention provides a compound of formula (I) as depicted above or an N-oxide thereof, or a pharmaceutically acceptable salt or solvate thereof, or a glucuronide derivative thereof, or a co-crystal thereof, wherein R$^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, $C_{4-9}$ heterobicycloalkenyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents; and E, Q, Y, Z, R$^2$ and R$^3$ are as defined above.

In another aspect, the present invention provides a compound of formula (I) as depicted above or an N-oxide thereof, or a pharmaceutically acceptable salt or solvate thereof, or a glucuronide derivative thereof, or a co-crystal thereof, wherein R$^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents; and E, Q, Y, Z, R$^2$ and R$^3$ are as defined above.

Where the compounds in accordance with the invention comprise an optionally substituted straight or branched alkylene chain, typical values thereof include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, trifluoromethyl, oxo, hydroxy, $C_{1-6}$ alkoxy, trifluoromethoxy, amino, $C_{1-6}$ alkylamino, di($C_{1-6}$)alkylamino, carboxy, tetrazolyl, aminocarbonyl, $C_{1-6}$ alkylaminocarbonyl and di($C_{1-6}$)alkylaminocarbonyl.

Examples of suitable substituents on the alkylene chain which may be present in a compound in accordance with the invention include halogen, trifluoromethyl, hydroxy, $C_{1-6}$ alkoxy, amino, carboxy and tetrazolyl, especially hydroxy or $C_{1-6}$ alkoxy.

Specific examples of suitable substituents on the alkylene chain which may be present in a compound in accordance with the invention include fluoro, trifluoromethyl, hydroxy, methoxy, amino, carboxy and tetrazolyl, especially hydroxy or methoxy.

In a first embodiment, E represents a covalent bond, whereby the integer Y is attached directly to the imidazo[1,2-a]pyrazine nucleus.

In a second embodiment, E represents —O—, —S—, —S(O)—, —S(O)$_2$— or —N(R$^4$)—. In a first aspect of that embodiment, E represents —O—. In a second aspect of that embodiment, E represents —S—. In a third aspect of that embodiment, E represents —S(O)—. In a fourth aspect of that embodiment, E represents —S(O)$_2$—. In a fifth aspect of that embodiment, E represents —N(R$^4$)—.

In a third embodiment, E represents an optionally substituted straight or branched $C_{1-4}$ alkylene chain. In a first aspect of that embodiment, E represents an optionally substituted methylene (—CH$_2$—) linkage. In a second aspect of that embodiment, E represents an optionally substituted (methyl)methylene linkage. In a third aspect of that embodiment, E represents an optionally substituted (ethyl)methylene linkage.

Generally, E represents a covalent bond; or E represents —N(R$^4$)—; or E represents an optionally substituted straight or branched $C_{1-4}$ alkylene chain.

Typically, E represents —N(R$^4$)—; or E represents an optionally substituted straight or branched $C_{1-4}$ alkylene chain.

Suitably, E represents a covalent bond; or E represents —N(R$^4$)—; or E represents methylene (—CH$_2$—), (methyl)methylene or (ethyl)methylene, any of which groups may be optionally substituted by one or more substituents.

Selected examples of typical substituents on the linkage represented by E include halogen, trifluoromethyl, hydroxy, $C_{1-6}$ alkoxy, trifluoromethoxy, amino, $C_{1-6}$ alkylamino, di($C_{1-6}$)alkylamino, carboxy and tetrazolyl, especially hydroxy or $C_{1-6}$ alkoxy.

Specific examples of typical substituents on the linkage represented by E include fluoro, trifluoromethyl, hydroxy, methoxy, trifluoromethoxy, amino, methylamino, dimethylamino, carboxy and tetrazolyl, especially hydroxy or methoxy.

A particular example of a typical substituent on E is hydroxy. Another example of a typical substituent on E is methoxy.

Typical values of E include —N(R$^4$)—, —CH$_2$—, —CH(OH)—, —CH(CH$_3$)— and —CH(CH$_2$CH$_3$)—; or E may represent a covalent bond. Additional values of E include —CH(OCH$_3$)— and —C(CH$_3$)(OH)—.

Suitable values of E include —CH$_2$— and —CH(OH)—. Additional values include —CH(OCH$_3$)—, —CH(CH$_3$)— and —C(CH$_3$)(OH)—.

In a first embodiment, E represents —CH$_2$—.

In a second embodiment, E represents —CH(OH)—.

In a third embodiment, E represents —CH(OCH$_3$)—.

In a fourth embodiment, E represents —CH(CH$_3$)—. In a particular aspect of that embodiment, the —CH(CH$_3$)— linkage represented by E is in the (S) stereochemical configuration.

In a fifth embodiment, E represents —C(CH$_3$)(OH)—.

In a first embodiment, Q represents a covalent bond, whereby the integer Z is attached directly to the imidazo[1,2-a]pyrazine nucleus.

In a second embodiment, Q represents —O—, —S—, —S(O)—, —S(O)$_2$—, —N(R$^5$)—, —C(O)N(R$^5$)—, —N(R$^5$)C(O)—, —S(O)$_2$N(R$^5$)— or —N(R$^5$)S(O)$_2$—. In a first aspect of that embodiment, Q represents —O—. In a second aspect of that embodiment, Q represents —S—. In a third aspect of that embodiment, Q represents —S(O)—. In a fourth aspect of that embodiment, Q represents —S(O)$_2$—. In a fifth aspect of that embodiment, Q represents —N(R$^5$)—. In a sixth aspect of that embodiment, Q represents —C(O)N(R$^5$)—. In a seventh aspect of that embodiment, Q represents —N(R$^5$)C(O)—. In an eighth aspect of that embodiment, Q represents —S(O)$_2$N(R$^5$)—. In a ninth aspect of that embodiment, Q represents —N(R$^5$)S(O)$_2$—.

In a third embodiment, Q represents an optionally substituted straight or branched C$_{1-6}$ alkylene chain optionally comprising one, two or three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—. In a first aspect of that embodiment, Q represents an optionally substituted straight or branched C$_{1-6}$ alkylene chain. In a second aspect of that embodiment, Q represents an optionally substituted straight or branched C$_{1-6}$ alkylene chain comprising one heteroatom-containing linkage independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—. In a third aspect of that embodiment, Q represents an optionally substituted straight or branched C$_{1-6}$ alkylene chain comprising two heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—. In a fourth aspect of that embodiment, Q represents an optionally substituted straight or branched C$_{1-6}$ alkylene chain comprising three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—. In a fifth aspect of that embodiment, Q represents an optionally substituted straight or branched C$_{1-6}$ alkylene chain comprising one, two or three heteroatom-containing linkages independently selected from —O—, —S—, —N(R$^5$)—, —C(O)N(R$^5$)— and —N(R$^5$)C(O)—.

Typically, Q represents a covalent bond; or Q represents —S(O)— or —S(O)$_2$—; or Q represents an optionally substituted straight or branched C$_{1-6}$ alkylene chain optionally comprising one or two heteroatom-containing linkages selected from —O—, —S—, —N(R$^5$)—, —C(O)N(R$^5$)—, and —N(R$^5$)C(O)—.

Selected examples of typical substituents on the linkage represented by Q include halogen, trifluoromethyl, hydroxy, C$_{1-6}$ alkoxy and amino.

Specific examples of typical substituents on the linkage represented by Q include fluoro, trifluoromethyl, hydroxy, methoxy and amino.

Suitably, Q represents a covalent bond; or Q represents —S(O)— or —S(O)$_2$—; or Q represents —CH$_2$—, —CH(F)—, —CF$_2$—, —CH(CH$_3$)—, —CH(OH)—, —CH(OCH$_3$)—, —CH(NH$_2$)—, —CH$_2$CH$_2$—, —CH(OH)CH$_2$—, —CH(OH)CF$_2$—, —CH(OCH$_3$)CH$_2$—, —CH$_2$O—, —CH(CH$_3$)O—, —C(CH$_3$)$_2$O—, —CH(CH$_2$CH$_3$)O—, —CH(CF$_3$)O—, —CH$_2$S—, —CH$_2$N(R$^5$)—, —CH$_2$CH$_2$CH$_2$—, —CH(OH)CH$_2$CH$_2$—, —CH(OCH$_3$)CH$_2$CH$_2$—, —CH$_2$CH$_2$O—, —CH$_2$OCH$_2$—, —CH$_2$OCH(F)—, —CH$_2$OCF$_2$—, —CH$_2$OCH(CH$_3$)—, —CH(CH$_3$)OCH$_2$—, —CH$_2$OC(CH$_3$)$_2$—, —C(CH$_3$)$_2$OCH$_2$—, —CH$_2$SCH$_2$—, —CH$_2$CH$_2$N(R$^5$)—, —CH$_2$N(R$^5$)CH$_2$—, —CH$_2$CH$_2$OCH$_2$—, —CH$_2$CH$_2$N(R$^5$)C(O)—, —CH$_2$OCH$_2$CH$_2$—, —CH$_2$OCH$_2$CF$_2$—, —CH$_2$OCH$_2$CH(CH$_3$)—, —CH$_2$OCH(CH$_3$)CH$_2$—, —CH$_2$OC(CH$_3$)$_2$CH$_2$—, —CH$_2$OCH$_2$CH(CH$_3$)CH$_2$—, —CH$_2$OCH$_2$CH$_2$O—, —CH$_2$OCH$_2$C(O)N(R$^5$)— or —CH$_2$OCH$_2$CH$_2$OCH$_2$—. Additional values include —N(R$^5$)—, —CH(CH$_2$OH)—, —CH$_2$S(O)—, —CH$_2$S(O)$_2$—, —CH$_2$S(O)CH$_2$—, —CH$_2$S(O)$_2$CH$_2$— and —CH$_2$N(R$^5$)C(O)—.

Particular values of Q include —CH$_2$—, —CH$_2$O—, —CH$_2$S— and —CH$_2$OCH$_2$—. In a first embodiment, Q represents —CH$_2$—. In a second embodiment, Q represents —CH$_2$O—. In a third embodiment, Q represents —CH$_2$S—. In a fourth embodiment, Q represents —CH$_2$OCH$_2$—.

Generally, Y represents C$_{3-7}$ cycloalkyl, aryl or heteroaryl, any of which groups may be optionally substituted by one or more substituents.

Typically, Y represents aryl or heteroaryl, either of which groups may be optionally substituted by one or more substituents.

In a first embodiment, Y represents optionally substituted C$_{3-7}$ cycloalkyl. In one aspect of that embodiment, Y represents unsubstituted C$_{3-7}$ cycloalkyl. In another aspect of that embodiment, Y represents monosubstituted C$_{3-7}$ cycloalkyl. In a further aspect of that embodiment, Y represents disubstituted C$_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted C$_{3-7}$ heterocycloalkyl. In one aspect of that embodiment, Y represents unsubstituted C$_{3-7}$ heterocycloalkyl. In another aspect of that embodiment, Y represents monosubstituted C$_{3-7}$ heterocycloalkyl. In a further aspect of that embodiment, Y represents disubstituted C$_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl or pyridinyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Typical examples of optional substituents on the moiety Y include halogen and difluoromethoxy.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical examples of particular substituents on the moiety Y include chloro and difluoromethoxy.

Typical values of Y include benzocyclobutenyl, phenyl, fluorophenyl (including 2-fluorophenyl, 3-fluorophenyl and 4-fluorophenyl), chlorophenyl (including 2-chlorophenyl, 3-chlorophenyl and 4-chlorophenyl), difluorophenyl (including 2,6-difluorophenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoromethyl)phenyl [including 2,5-bis(trifluoromethyl)phenyl], methoxyphenyl (including 2-methoxyphenyl), (difluoromethoxy)phenyl [including 2-(difluoromethoxy)phenyl and 3-(difluoromethoxy)phenyl], (difluoromethoxy)(fluoro)phenyl [including 2-(difluoro-methoxy)-5-fluorophenyl and 5-(difluoromethoxy)-2-fluorophenyl], (chloro)-(difluoromethoxy)phenyl [including 5-chloro-2-(difluoromethoxy)phenyl and 6-chloro-2-(difluoromethoxy)phenyl], (trifluoromethoxy)phenyl [including 2-(trifluoromethoxy)-phenyl], (amino)(chloro)phenyl (including 5-amino-2-chlorophenyl), methylthienyl (including 3-methylthien-2-yl), methylthiazolyl (including 2-methyl-1,3-thiazol-4-yl), (chloro)(methyl)thiazolyl (including 5-chloro-2-methyl-1,3-thiazol-4-yl), dimethyl-thiazolyl (including 2,4-dimethyl-1,3-thiazol-5-yl) and pyridinyl (including pyridin-3-yl and pyridin-4-yl).

Suitable values of Y include dichlorophenyl and (difluoromethoxy)phenyl.

In one embodiment, Y represents 2,5-dichlorophenyl.

In a particular embodiment, Y represents 2-(difluoromethoxy)phenyl.

In one embodiment, Z represents hydrogen.

In another embodiment, Z is other than hydrogen.

In a selected embodiment, Z represents hydrogen; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents $-Z^1-Z^2$ or $-Z^1-C(O)-Z^2$, either of which moieties may be optionally substituted by one or more substituents.

In a further embodiment, Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents $-Z^1-Z^2$ or $-Z^1-C(O)-Z^2$, either of which moieties may be optionally substituted by one or more substituents.

Typically, Z represents hydrogen, fluoro or trifluoromethyl; or Z represents methyl, ethyl, n-propyl, isopropyl, n-butyl, sec-butyl, isobutyl, tert-butyl, cyclopropyl, cyclobutyl, cyclopentyl, cyclohexyl, phenyl, tetrahydrofuranyl, pyrrolidinyl, indolinyl, tetrahydropyranyl, piperidinyl, 1,2,3,4-tetrahydroquinolinyl, morpholinyl, azocanyl, thiazolinyl, furyl, thienyl, pyrazolyl, 4,5,6,7-tetrahydroindazolyl, benzoxazolyl, isoxazolyl, thiazolyl, benzothiazolyl, imidazolyl, benzimidazolyl, [1,2,4]triazolo[1,5-a]-pyrimidinyl, tetrazolyl, pyridinyl, quinolinyl, isoquinolinyl, phthalazinyl, pyrimidinyl or pyrazinyl, any of which groups may be optionally substituted by one or more substituents; or Z represents $-Z^1-Z^2$ or $-Z^1-C(O)-Z^2$, either of which moieties may be optionally substituted by one or more substituents.

The moiety $Z^1$ represents a divalent radical derived from an aryl, $C_{3-7}$ heterocycloalkyl or heteroaryl group, any of which groups may be optionally substituted by one or more substituents. Typically, the moiety $Z^1$ represents a divalent radical derived from a phenyl, pyrrolidinyl, piperazinyl, pyrazolyl, thiazolyl, triazolyl, tetrazolyl or pyridinyl group, any of which groups may be optionally substituted by one or more substituents. Typical values of the moiety $Z^1$ include the groups of formula (Za), (Zb), (Zc), (Zd), (Ze), (Zf), (Zg), (Zh) and (Zj):

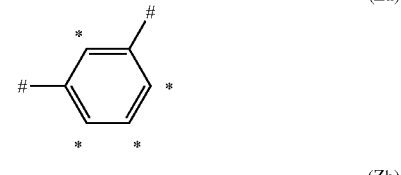

(Za)

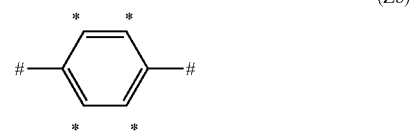

(Zb)

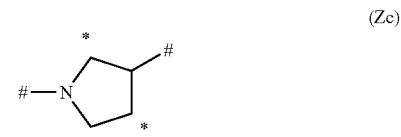

(Zc)

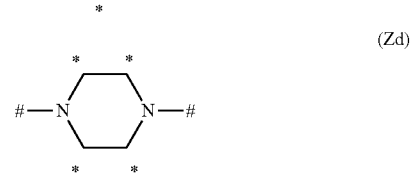

(Zd)

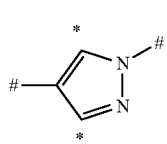
(Ze)

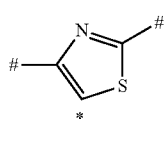
(Zf)

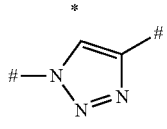
(Zg)

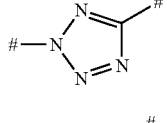
(Zh)

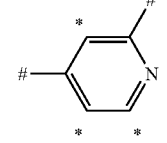
(Zj)

wherein the symbols # represent the points of attachment of the moiety $Z^1$ to the remainder of the molecule; and the asterisks (*) represent the site of attachment of optional substituents.

Particular values of the moiety Z' include the groups of formula (Za), (Zc), (Ze), (Zf), (Zg), (Zh) and (Zj) as depicted above.

The moiety $Z^2$ represents aryl, $C_{3-7}$ heterocycloalkyl, $C_{3-7}$ heterocycloalkenyl or heteroaryl, any of which groups may be optionally substituted by one or more substituents. Typically, $Z^2$ represents phenyl, pyrrolidinyl, oxazolidinyl, imidazolidinyl, morpholinyl, imidazolinyl, thiazolyl, imidazolyl, tetrazolyl or pyridinyl, any of which groups may be optionally substituted by one or more substituents.

Examples of optional substituents which may be present on the moiety Z, $Z^1$ or $Z^2$ include one, two or three substituents independently selected from halogen, cyano, nitro, $C_{1-6}$ alkyl, trifluoromethyl, oxo, hydroxy, hydroxy($C_{1-6}$)alkyl, $C_{1-6}$ alkoxy, difluoro-methoxy, trifluoromethoxy, $C_{1-3}$ alkylenedioxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, aminocarbonylamino and hydrazinocarbonyl.

Typical examples of optional substituents on the moiety Z, $Z^1$ or $Z^2$ include halogen, cyano, nitro, $C_{1-6}$ alkyl, trifluoromethyl, oxo, hydroxy, hydroxy($C_{1-6}$)alkyl, $C_{1-6}$ alkoxy, difluoromethoxy, trifluoromethoxy, $C_{1-3}$ alkylenedioxy, $C_{1-6}$ alkylsulfonyl, amino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, carboxy, $C_{2-6}$ alkoxycarbonyl, aminocarbonyl, $C_{1-6}$ alkylaminocarbonyl, di($C_{1-6}$)alkylaminocarbonyl, aminocarbonylamino and hydrazinocarbonyl.

Examples of particular substituents on the moiety Z, $Z^1$ or $Z^2$ include fluoro, chloro, bromo, cyano, nitro, methyl, ethyl, isopropyl, trifluoromethyl, oxo, hydroxy, hydroxymethyl, methoxy, difluoromethoxy, trifluoromethoxy, methylenedioxy, methylthio, methylsulfinyl, methylsulfonyl, amino, methylamino, tert-butylamino, dimethylamino, dimethylaminomethyl, dimethylaminoethyl, acetylamino, methylsulfonylamino, formyl, acetyl, carboxy, methoxycarbonyl, tert-butoxycarbonyl, aminocarbonyl, methylaminocarbonyl, dimethylaminocarbonyl, aminosulfonyl, methylaminosulfonyl, dimethylaminosulfonyl, aminocarbonylamino and hydrazinocarbonyl.

Typical examples of particular substituents on the moiety Z, $Z^1$ or $Z^2$ include fluoro, chloro, bromo, cyano, nitro, methyl, ethyl, trifluoromethyl, oxo, hydroxy, hydroxymethyl, methoxy, difluoromethoxy, trifluoromethoxy, methylenedioxy, methylsulfonyl, amino, dimethylamino, dimethylaminomethyl, dimethylaminoethyl, acetylamino, methylsulfonylamino, formyl, carboxy, methoxycarbonyl, tert-butoxycarbonyl, aminocarbonyl, methylaminocarbonyl, dimethylaminocarbonyl, aminocarbonylamino and hydrazinocarbonyl.

Typical values of $Z^2$ include phenyl, hydroxyphenyl, oxopyrrolidinyl, dioxo-pyrrolidinyl, (hydroxy)(oxo)pyrrolidinyl, (amino)(oxo)pyrrolidinyl, (oxo)oxazolidinyl, oxoimidazolidinyl, morpholinyl, imidazolinyl, methylthiazolyl, formylthiazolyl, imidazolyl, tetrazolyl and pyridinyl.

Selected values of $Z^2$ include oxopyrrolidinyl and (oxo) oxazolidinyl. In one embodiment, $Z^2$ represents oxopyrrolidinyl. In another embodiment, $Z^2$ represents (oxo)oxazolidinyl.

Typical values of Z include hydrogen, fluoro, trifluoromethyl, methyl, ethyl, n-propyl, isopropyl, isobutyl, tert-butyl, cyclopropyl, cyclopentyl, cyclohexyl, oxo-cyclohexyl, phenyl, bromophenyl, cyanophenyl, nitrophenyl, methoxyphenyl, difluoro-methoxyphenyl, trifluoromethoxyphenyl, methylenedioxyphenyl, methylsulfonylphenyl, dimethylaminophenyl, acetylaminophenyl, methylsulfonylaminophenyl, carboxyphenyl, aminocarbonylphenyl, methylaminocarbonylphenyl, dimethylaminocarbonylphenyl, aminocarbonylaminophenyl, tetrahydrofuranyl, oxopyrrolidinyl, dimethylamino-pyrrolidinyl, tert-butoxycarbonylpyrrolidinyl, indolinyl, tetrahydropyranyl, piperidinyl, ethylpiperidinyl, tert-butoxycarbonylpiperidinyl, aminocarbonylpiperidinyl, 2-oxo-3,4-dihydroquinolinyl, morpholinyl, azocanyl, oxothiazolinyl, furyl, hydroxymethylfuryl, thienyl, methylpyrazolyl, dimethylpyrazolyl, 4,5,6,7-tetrahydroindazolyl, benzoxazolyl, methylisoxazolyl, dimethylisoxazolyl, methylthiazolyl, aminothiazolyl, benzothiazolyl, methylbenzothiazolyl, aminobenzothiazolyl, imidazolyl, methylimidazolyl, methyl-benzimidazolyl, dimethyl[1,2,4] triazolo[1,5-a]pyrimidinyl, dimethylaminoethyltetrazolyl, pyridinyl, fluoropyridinyl, chloropyridinyl, cyanopyridinyl, methylpyridinyl, (cyano)-(methyl)pyridinyl, trifluoromethylpyridinyl, oxopyridinyl, methoxypyridinyl, dimethylaminomethylpyridinyl, acetylaminopyridinyl, carboxypyridinyl, methoxycarbonyl-pyridinyl, aminocarbonylpyridinyl, (aminocarbonyl)(fluoro)pyridinyl, methylaminocarbonylpyridinyl, dimethylaminocarbonylpyridinyl, hydrazinocarbonylpyridinyl, quinolinyl, isoquinolinyl, (methyl)(oxo)phthalazinyl, pyrimidinyl, pyrazinyl, oxopyrrolidinylphenyl, dioxopyrrolidinylphenyl, (hydroxy)(oxo)pyrrolidinylphenyl, (amino)(oxo)pyrrolidinylphenyl, (oxo)oxazolidinylphenyl, oxoimidazolidinylphenyl, imidazolinylphenyl, methylthiazolylphenyl, formylthiazolylphenyl, imidazolylphenyl, tetrazolylphenyl, phenylpyrrolidinyl, hydroxyphenylpiperazinyl, (methyl)(phenyl)-pyrazolyl, oxoimidazolidinylthiazolyl, hydroxyphenyltriazolyl, morpholinyltetrazolyl, oxopyrrolidinylpyridinyl, (oxo)oxazolidinylpyridinyl, oxoimidazolidinylpyridinyl, pyridinylthiazolyl, pyridinyltetrazolyl and morpholinylcarbonylphenyl.

Particular values of Z include hydrogen, methyl, methylsulfonylphenyl, pyridinyl, oxopyrrolidinylphenyl, (hydroxy)(oxo)pyrrolidinylphenyl and (oxo)oxazolidinylphenyl. In a first embodiment, Z represents hydrogen. In a second embodiment, Z represents methyl. In a third embodiment, Z represents methylsulfonylphenyl. In one aspect of that embodiment, Z represents 3-(methylsulfonyl)phenyl. In a fourth embodiment, Z represents pyridinyl. In one aspect of that embodiment, Z represents pyridin-4-yl. In a fifth embodiment, Z represents oxopyrrolidinylphenyl. In one aspect of that embodiment, Z represents 3-(2-oxopyrrolidin-1-yl)phenyl. In a sixth embodiment, Z represents (hydroxy)(oxo)pyrrolidinylphenyl. In one aspect of that embodiment, Z represents 3-(3-hydroxy-2-oxopyrrolidin-1-yl)phenyl. In another aspect of that embodiment, Z represents 3-(4-hydroxy-2-oxopyrrolidin-1-yl)phenyl. In a seventh embodiment, Z represents (oxo)oxazolidinylphenyl. In one aspect of that embodiment, Z represents 3-(2-oxooxazolidin-3-yl)phenyl.

Generally, $R^1$, $R^2$ and $R^3$ independently represent hydrogen, halogen, cyano, nitro, hydroxy, trifluoromethyl, trifluoromethoxy, —$OR^a$, —$SR^a$, —$SOR^a$, —$SO_2R^a$, —$SF_5$, —$NR^bR^c$, —$NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl-($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl-($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Typically, $R^1$, $R^2$ and $R^3$ independently represent hydrogen, halogen, cyano or —$CO_2R^d$; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents. Additionally, $R^1$, $R^2$ and $R^3$ may independently represent $C_{4-9}$ heterobicycloalkenyl or ($C_{3-7}$)cycloalkyl-heteroaryl-, either of which groups may be optionally substituted by one or more substituents.

Examples of optional substituents which may be present on $R^1$, $R^2$ or $R^3$ include one, two or three substituents independently selected from halogen, cyano, cyano($C_{1-6}$)alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy($C_{1-6}$)-alkyl, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy-($C_{1-6}$)alkyl]amino, $C_{2-6}$ alkylcarbonylamino, $C_{2-6}$ alkoxycarbonylamino, $C_{1-6}$ alkylaminocarbonylamino, $C_{1-6}$ alkylsulphonylamino, formyl, $C_{2-6}$ alkylcarbonyl, carboxy, carboxy-($C_{1-6}$)alkyl, $C_{2-6}$ alkoxycarbonyl, $C_{2-6}$ alkoxycarbonyl($C_{1-6}$)alkyl, tetrazolyl, aminocarbonyl, $C_{1-6}$ alkylaminocarbonyl, di($C_{1-6}$)alkylaminocarbonyl, $C_{1-6}$ alkylsulphonylaminocarbonyl, aminosulphonyl, $C_{1-6}$ alkylaminosulphonyl and di($C_{1-6}$)alkylaminosulphonyl. Additional examples include halo($C_{1-6}$)alkyl, difluoromethyl, difluoroethyl, hydroxy($C_{1-6}$)alkyl, $C_{1-6}$ alkylsulphinyl, amino($C_{1-6}$)alkyl, hydroxy($C_{1-6}$)alkylamino, [($C_{1-6}$)alkoxy](hydroxy)($C_{1-6}$)alkylamino, [($C_{1-6}$)alkylthio](hydroxy)($C_{1-6}$)alkylamino, di($C_{1-6}$)alkylamino($C_{1-6}$)alkylamino, N—[di($C_{1-6}$)alkylamino($C_{1-6}$)alkyl]-N-[hydroxy ($C_{1-6}$)-alkyl]amino, hydroxy($C_{1-6}$)alkyl($C_{3-7}$)cycloalkylamino, (hydroxy)[($C_{3-7}$)cycloalkyl($C_{1-6}$)-alkyl]amino, ($C_{3-7}$)heterocycloalkylamino, ($C_{3-7}$)heterocycloalkyl($C_{1-6}$)alkylamino, oxo-($C_{3-7}$)heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, N—[($C_{1-6}$)alkyl]-N—[($C_{2-6}$)alkylcarbonyl]-amino, ($C_{2-6}$)alkylcarbonylamino ($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, N-[carboxy($C_{1-6}$)-alkyl]-N—[($C_{1-6}$)alkyl]amino, $C_{2-6}$ alkoxycarbonyl($C_{1-6}$)alkylamino, N—[($C_{1-6}$)alkyl]-N—[($C_{1-6}$)alkylsulphonyl]amino, ($C_{1-6}$) alkylsulphonylamino($C_{1-6}$)alkyl, ($C_{3-7}$)cycloalkylcarbonyl, phenylcarbonyl, tetrazolyl($C_{1-6}$)alkyl, aminocarbonyl($C_{1-6}$) alkyl and hydroxy-($C_{1-6}$)alkylaminocarbonyl.

In particular, $R^1$, $R^2$ or $R^3$ may be substituted by a carboxylic acid isostere or prodrug moiety. By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). Typical examples of suitable carboxylic acid isostere or prodrug moieties include the functional groups of formula (i) to (xli):

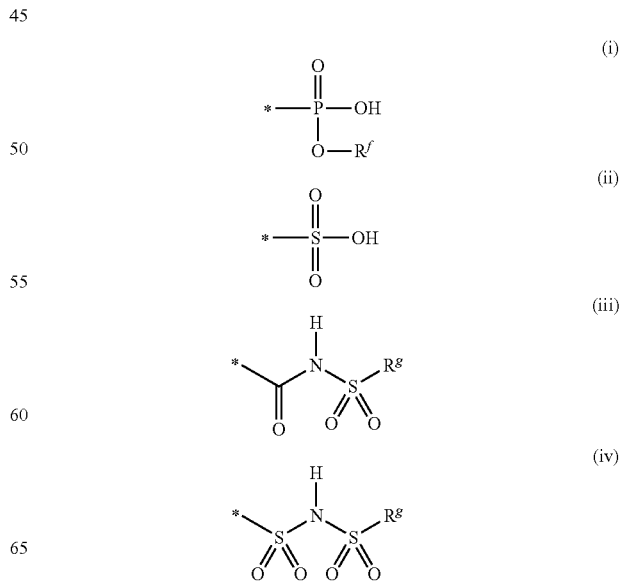

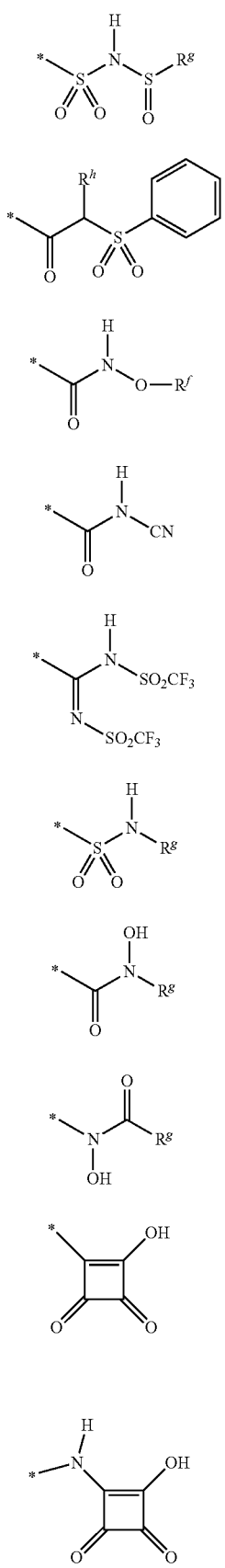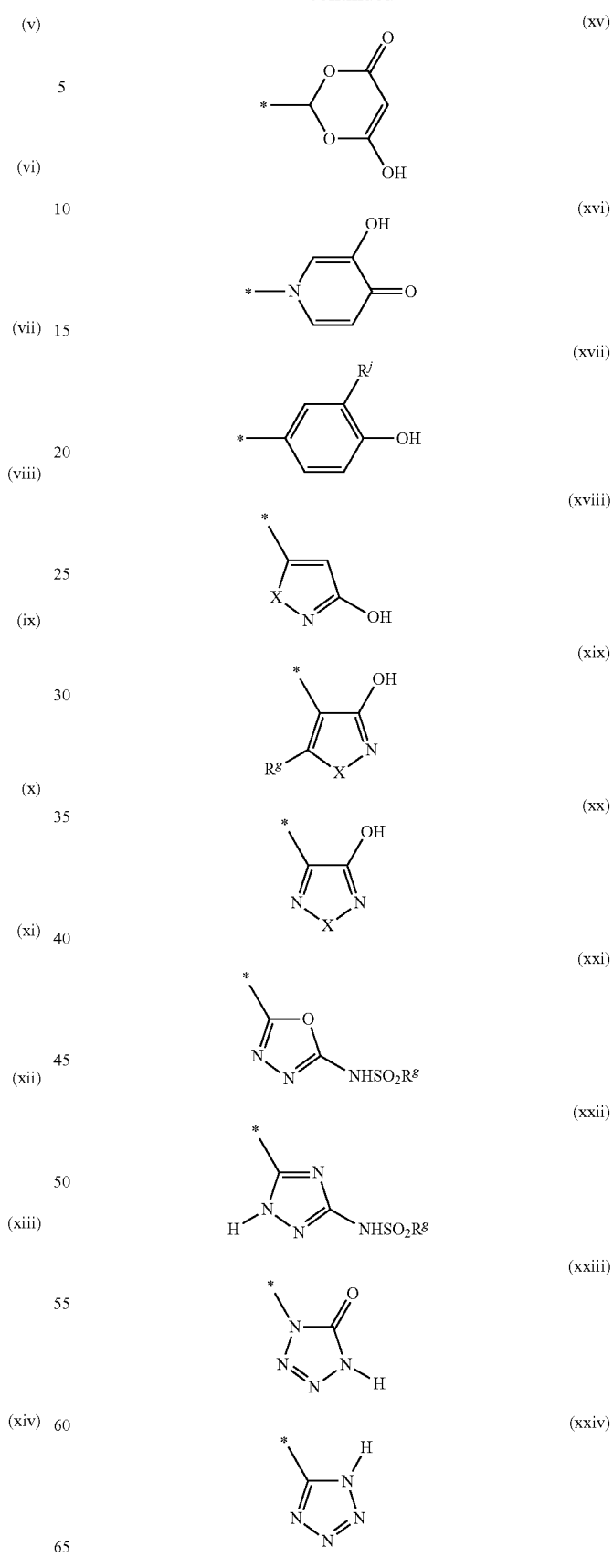

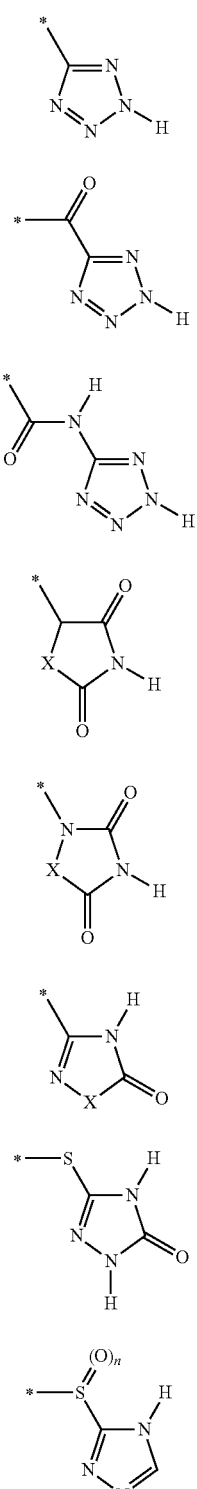
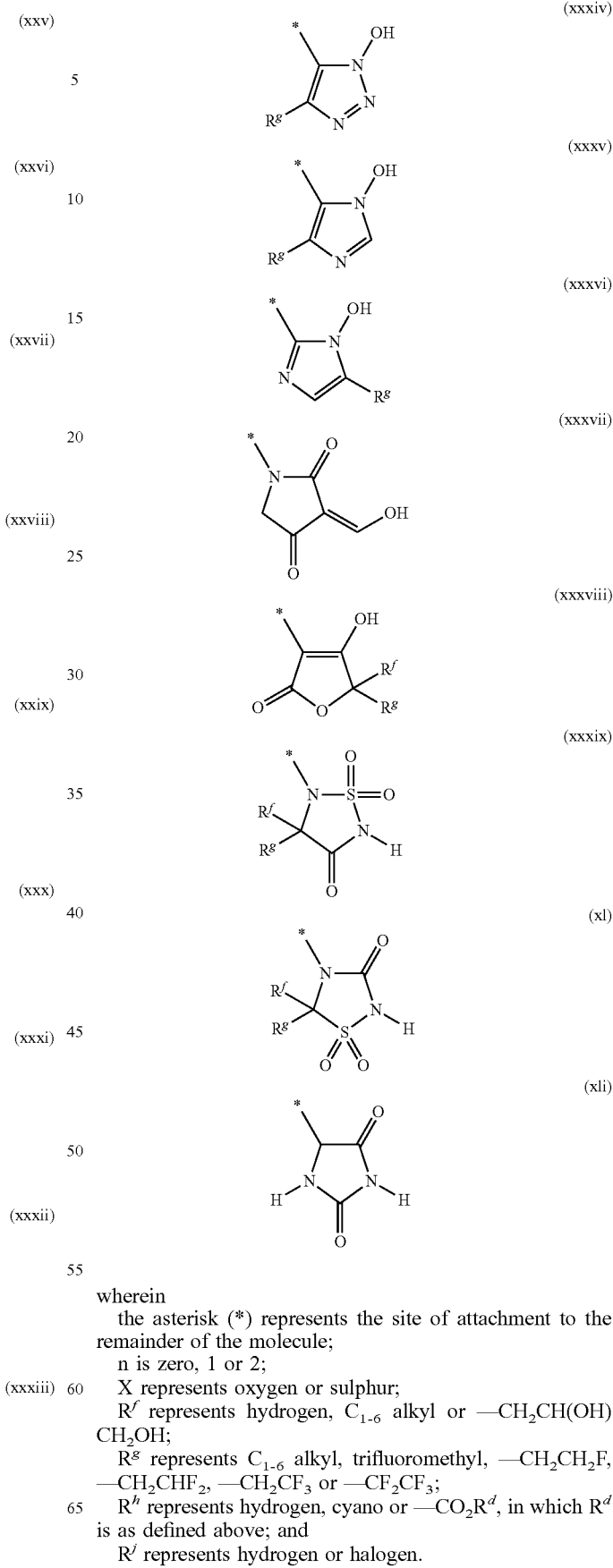

wherein
the asterisk (*) represents the site of attachment to the remainder of the molecule;
n is zero, 1 or 2;
X represents oxygen or sulphur;
$R^f$ represents hydrogen, $C_{1-6}$ alkyl or —CH$_2$CH(OH)CH$_2$OH;
$R^g$ represents $C_{1-6}$ alkyl, trifluoromethyl, —CH$_2$CH$_2$F, —CH$_2$CHF$_2$, —CH$_2$CF$_3$ or —CF$_2$CF$_3$;
$R^h$ represents hydrogen, cyano or —CO$_2$R$^d$, in which $R^d$ is as defined above; and
$R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —$CH_2CH(OH)CH_2OH$.

In one embodiment, $R^g$ represents $C_{1-6}$ alkyl, especially methyl. In another embodiment, $R^g$ represents trifluoromethyl, —$CH_2CH_2F$, —$CH_2CHF_2$, —$CH_2CF_3$ or —$CF_2CF_3$. In a first aspect of that embodiment, $R^g$ represents trifluoromethyl. In a second aspect of that embodiment, $R^g$ represents —$CH_2CH_2F$. In a third aspect of that embodiment, $R^g$ represents —$CH_2CHF_2$. In a fourth aspect of that embodiment, $R^g$ represents —$CH_2CF_3$. In a fifth aspect of that embodiment, $R^g$ represents —$CF_2CF_3$.

In one embodiment, $R^h$ is hydrogen. In another embodiment, $R^h$ represents cyano. In a further embodiment, $R^h$ represents —$CO_2R^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents ($C_{1-6}$)alkylcarbonylaminosulphonyl, i.e. a moiety of formula (v) as depicted above wherein $R^g$ represents $C_{1-6}$ alkyl.

Additional examples of suitable carboxylic acid isostere or prodrug moieties represented by Ω include the functional group of formula (xlii):

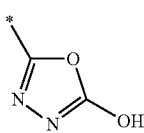

(xlii)

wherein
the asterisk (*) represents the site of attachment to the remainder of the molecule.

Suitable examples of optional substituents which may be present on $R^1$, $R^2$ or $R^3$ include one, two or three substituents independently selected from halogen, cyano, $C_{1-6}$ alkyl, hydroxy, $C_{1-6}$ alkoxy, $C_{1-6}$ alkylsulphonyl, oxo, $C_{2-6}$ alkylcarbonyl, carboxy, carboxy($C_{1-6}$)alkyl, $C_{2-6}$ alkoxycarbonyl and aminosulphonyl. Additional examples include hydroxy ($C_{1-6}$)alkyl, ($C_{3-7}$)heterocycloalkylamino, tetrazolyl($C_{1-6}$) alkyl and aminocarbonyl($C_{1-6}$)alkyl.

Examples of particular substituents on $R^1$, $R^2$ or $R^3$ include fluoro, chloro, bromo, cyano, cyanoethyl, nitro, methyl, ethyl, tert-butyl, trifluoromethyl, trifluoroethyl, ethenyl, hydroxy, methoxy, isopropoxy, difluoromethoxy, trifluoromethoxy, trifluoroethoxy, methylenedioxy, ethylenedioxy, methoxymethyl, methylthio, methylsulphonyl, methylsulphonylethyl, oxo, amino, methylamino, dimethylamino, methoxyethylamino, N-(hydroxyethyl)-N-(methyl) amino, acetylamino, methoxycarbonylamino, ethoxycarbonylamino, ethylaminocarbonylamino, butylaminocarbonylamino, methylsulphonylamino, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonylmethyl, methylaminocarbonyl, dimethylaminocarbonyl, methylsulphonylaminocarbonyl, aminosulphonyl, methylaminosulphonyl and dimethylaminosulphonyl. Additional examples include isopropyl, isobutyl, difluoromethyl, difluoroethyl, hydroxymethyl, hydroxyethyl, hydroxyisopropyl, methoxyethyl, methylsulphinyl, ethylamino, hydroxyethylamino, hydroxypropylamino, (hydroxy)(methyl)propylamino, (hydroxy)-(methoxy)(methyl)propylamino, (hydroxy)(methylthio)butylamino, dimethylaminoethylamino, (dimethylamino)(methyl)propylamino, N-(dimethylaminoethyl)-N-(hydroxyethyl)-amino, hydroxymethylcyclopentylamino, hydroxycyclobutylmethylamino, (cyclopropyl)-(hydroxy)propylamino, tetrahydrofuranylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, N-acetyl-N-methylamino, N-isopropylcarbonyl-N-methylamino, ethenylcarbonylamino, bis(ethenylcarbonyl)amino, N-cyclopropylcarbonyl-N-methylamino, N-(carboxymethyl)-N-methylamino, N-(carboxyethyl)-N-methylamino, tert-butoxycarbonylamino, methoxycarbonylethylamino, N-methyl-N-(methylsulphonyl)amino, isopropylcarbonyl, cyclobutylcarbonyl, phenylcarbonyl, tetrazolylmethyl, aminocarbonylmethyl and hydroxyethylaminocarbonyl.

Suitable examples of particular substituents on $R^1$, $R^2$ or $R^3$ include fluoro, cyano, methyl, hydroxy, methoxy, methylsulphonyl, oxo, acetyl, carboxy, carboxymethyl, carboxyethyl, ethoxycarbonyl, tert-butoxycarbonyl and amino sulphonyl. Additional examples include hydroxyisopropyl, tetrahydrofuranylamino, tetrazolylmethyl and aminocarbonylmethyl.

Typically, $R^1$ represents hydrogen, halogen, cyano or —$CO_2R^d$; or $C_{1-6}$ alkyl, aryl, $C_{3-7}$ heterocycloalkyl, $C_{3-7}$ heterocycloalkenyl, heteroaryl, ($C_{3-7}$)heterocycloalkyl-($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents. Additionally, $R^1$ may represent ($C_{4-9}$)-heterobicycloalkenyl- or ($C_{3-7}$)cycloalkyl-heteroaryl-, either of which groups may be optionally substituted by one or more substituents.

Suitably, $R^1$ represents halogen, cyano or —$CO_2R^d$; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents. Additionally, $R^1$ may represent ($C_{4-9}$)-heterobicycloalkenyl- or ($C_{3-7}$)cycloalkyl-heteroaryl-, either of which groups may be optionally substituted by one or more substituents.

Generally, $R^1$ represents halogen or cyano; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl ($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents. Additionally, $R^1$ may represent ($C_{4-9}$)-heterobicycloalkenyl- or ($C_{3-7}$)cycloalkyl-heteroaryl-, either of which groups may be optionally substituted by one or more substituents.

More generally, $R^1$ represents halogen or cyano; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl($C_{3-7}$)heterocycloalkyl-, ($C_{3-7}$)heterocycloalkyl-heteroaryl-, ($C_{3-7}$)heterocycloalkyl($C_{1-6}$)alkyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents. Additionally, $R^1$ may represent ($C_{4-9}$)-heterobicycloalkenyl- or ($C_{3-7}$)cycloalkyl-heteroaryl-, either of which groups may be optionally substituted by one or more substituents.

Still more generally, $R^1$ represents halogen; or aryl, $C_{3-7}$ heterocycloalkyl, $C_{3-7}$ heterocycloalkenyl, ($C_{4-9}$)heterobicycloalkenyl-, heteroaryl, ($C_{3-7}$)cycloalkyl-heteroaryl-, ($C_{3-7}$) heterocycloalkyl-heteroaryl-, ($C_{4-9}$)heterobicycloalkyl-heteroaryl- or ($C_{4-9}$)-spiroheterocycloalkyl-heteroaryl-, any of which groups may be optionally substituted by one or more substituents.

Even more generally, $R^1$ represents heteroaryl or ($C_{3-7}$) heterocycloalkyl-heteroaryl-, either of which groups may be optionally substituted by one or more substituents. Additionally, $R^1$ may represent aryl, $C_{3-7}$ heterocycloalkyl, $C_{3-7}$ heterocycloalkenyl, ($C_{4-9}$)heterobicycloalkyl-heteroaryl- or ($C_{4-9}$)spiroheterocycloalkyl-heteroaryl-, any of which groups may be optionally substituted by one or more substituents. Additionally, $R^1$ may represent halogen.

In a first embodiment, $R^1$ represents hydrogen.

In a second embodiment, $R^1$ represents halogen. In one aspect of that embodiment, $R^1$ represents bromo.

In a third embodiment, $R^1$ represents cyano.

In a fourth embodiment, $R^1$ represents $-CO_2R^d$.

In a fifth embodiment, $R^1$ represents optionally substituted $C_{1-6}$ alkyl. In one aspect of that embodiment, $R^1$ represents optionally substituted ethyl.

In a sixth embodiment, $R^1$ represents optionally substituted aryl. In one aspect of that embodiment, $R^1$ represents optionally substituted phenyl.

In a seventh embodiment, $R^1$ represents optionally substituted $C_{3-7}$ heterocycloalkyl. In one aspect of that embodiment, $R^1$ represents optionally substituted piperidinyl.

In an eighth embodiment, $R^1$ represents optionally substituted $C_{3-7}$ heterocycloalkenyl. In a first aspect of that embodiment, $R^1$ represents optionally substituted dihydropyranyl. In a second aspect of that embodiment, $R^1$ represents optionally substituted dihydrothiopyranyl. In a third aspect of that embodiment, $R^1$ represents optionally substituted 1,2,3,6-tetrahydropyridinyl.

In a ninth embodiment, $R^1$ represents optionally substituted ($C_{4-9}$)-heterobicycloalkenyl-. In one aspect of that embodiment, $R^1$ represents optionally substituted 8-azabicyclo[3.2.1]octenyl.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted ($C_{3-7}$)-heterocycloalkyl($C_{1-6}$)alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl($C_{3-7}$)-heterocycloalkyl-. In one aspect of that embodiment, $R^1$ represents optionally substituted pyridinylpiperazinyl-.

In a thirteenth embodiment, $R^1$ represents optionally substituted ($C_{3-7}$)cycloalkyl-heteroaryl-. In one aspect of that embodiment, $R^1$ represents optionally substituted cyclohexylpyrimidinyl-.

In a fourteenth embodiment, $R^1$ represents optionally substituted ($C_{4-7}$)-cycloalkenyl-heteroaryl-.

In a fifteenth embodiment, $R^1$ represents optionally substituted ($C_{3-7}$)-heterocycloalkyl-heteroaryl-. In a first aspect of that embodiment, $R^1$ represents optionally substituted morpholinylthiazolyl-. In a second aspect of that embodiment, $R^1$ represents optionally substituted pyrrolidinylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinylpyridinyl-. In a seventh aspect of that embodiment, $R^1$ represents optionally substituted diazepanylpyridinyl-. In an eighth aspect of that embodiment, $R^1$ represents optionally substituted pyrrolidinylpyrimidinyl-. In a ninth aspect of that embodiment, $R^1$ represents optionally substituted piperidinylpyrimidinyl-. In a tenth aspect of that embodiment, $R^1$ represents optionally substituted piperazinylpyrimidinyl-. In an eleventh aspect of that embodiment, $R^1$ represents optionally substituted morpholinylpyrimidinyl-. In a twelfth aspect of that embodiment, $R^1$ represents optionally substituted thiomorpholinylpyrimidinyl-. In a thirteenth aspect of that embodiment, $R^1$ represents optionally substituted diazepanylpyrimidinyl-. In a fourteenth aspect of that embodiment, $R^1$ represents optionally substituted thiadiazepanylpyrimidinyl-.

In a sixteenth embodiment, $R^1$ represents optionally substituted ($C_{3-7}$)-heterocycloalkyl($C_{1-6}$)alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted ($C_{3-7}$)-heterocycloalkenyl-heteroaryl-.

In an eighteenth embodiment, $R^1$ represents optionally substituted ($C_{4-9}$)-heterobicycloalkyl-heteroaryl-.

In a nineteenth embodiment, $R^1$ represents optionally substituted ($C_{4-9}$)-spiroheterocycloalkyl-heteroaryl-.

Appositely, $R^1$ represents hydrogen, bromo, cyano or $-CO_2R^d$; or ethyl, phenyl, piperidinyl, piperazinyl, morpholinyl, 1,2,3,6-tetrahydropyridinyl, benzofuryl, thienyl, indolyl, pyrazolyl, indazolyl, isoxazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, pyrrolidinylpyridinyl, piperidinylpyridinyl, piperazinylpyridinyl, morpholinylpyridinyl, thiomorpholinylpyridinyl, diazepanylpyridinyl, pyrrolidinylpyrimidinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl, morpholinylmethylthienyl, morpholinylethylpyrazolyl, 2-oxa-5-azabicyclo[2.2.1]-heptanylpyrimidinyl, 2-oxa-6-azaspiro[3.3]heptanylpyrimidinyl, 2-oxa-6-azaspiro[3.4]- octanylpyrimidinyl, 2-oxa-6-azaspiro[3.5]nonanylpyrimidinyl or 2-oxa-7-azaspiro[3.5]nonanylpyrimidinyl, any of which groups may be optionally substituted by one or more substituents. Additionally, $R^1$ may represent chloro, trifluoromethyl, —$OR^a$, —$SO_2R^a$ or —$CONR^bR^c$; or methyl, dihydropyranyl, dihydrothiopyranyl, 8-azabicyclo[3.2.1]octenyl, dihydrothieno[3,4-b][1,4]dioxinyl, dihydropyrrolo[3,4-b]pyridinyl, imidazolylmethyl, triazolylmethyl, pyridinylmethyl, morpholinylmethylphenyl, cyclopropylpyrimidinyl, cyclobutylpyrimidinyl, cyclopentylpyrimidinyl, cyclohexylpyrimidinyl, cyclohexenyl-pyrimidinyl, morpholinylthiazolyl, azetidinylpyridinyl, isothiazolidinylpyridinyl, imidazolidinylpyridinyl, oxetanylpyrimidinyl, azetidinylpyrimidinyl, tetrahydrofuranyl-pyrimidinyl, isothiazolidinylpyrimidinyl, tetrahydropyranylpyrimidinyl, azetidinylmethyl-pyridinyl, piperazinylmethylpyridinyl, morpholinylmethylpyridinyl, thiomorpholinyl-methylpyridinyl, morpholinylmethylpyrimidinyl, 3-azabicyclo[3.1.0]hexanylpyrimidinyl, 3-azabicyclo[4.1.0]heptanylpyrimidinyl, 3-azabicyclo[3.2.1]octanylpyrimidinyl, 3,6-diazabicyclo[3.2.2]nonanylpyrimidinyl, 2-oxa-6-azaspiro[3.4]octanylpyridinyl, 2-azaspiro[3.3]heptanylpyrimidinyl, 5-azaspiro[2.4]heptanylpyrimidinyl or 7-oxa-2-azaspiro[3.5]nonanylpyrimidinyl, any of which groups may be optionally substituted by one or more substituents.

Definitively, $R^1$ represents bromo; or phenyl, piperidinyl, dihydropyranyl, dihydrothiopyranyl, 1,2,3,6-tetrahydropyridinyl, 8-azabicyclo[3.2.1]octenyl, indolyl, pyrazolyl, pyridinyl, pyrimidinyl, cyclohexylpyrimidinyl, morpholinylthiazolyl, piperidinylpyridinyl, piperazinylpyridinyl, morpholinylpyridinyl, pyrrolidinylpyrimidinyl, piperidinylpyrimidinyl, piperazinylpyrimidinyl, morpholinylpyrimidinyl, diazepanylpyrimidinyl, 3-azabicyclo[3.1.0]hexanylpyrimidinyl, 3-azabicyclo[4.1.0]heptanylpyrimidinyl, 3,6-diazabicyclo[3.2.2]nonanylpyrimidinyl, 2-azaspiro[3.3]heptanylpyrimidinyl or 2-oxa-6-azaspiro[3.3]heptanylpyrimidinyl, any of which groups may be optionally substituted by one or more substituents.

Illustratively, $R^1$ represents pyridinyl, piperazinylpyrimidinyl or diazepanylpyrimidinyl, any of which groups may be optionally substituted by one or more substituents.

Typical examples of optional substituents on $R^1$ include one, two or three substituents independently selected from halogen, cyano, cyano($C_{1-6}$)alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, ($C_{1-6}$)alkylsulphonyl($C_{1-6}$)alkyl, oxo, amino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, $C_{1-6}$ alkylsulphonylamino, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl, aminocarbonyl and $C_{1-6}$ alkylsulphonylaminocarbonyl. Additional examples include halo($C_{1-6}$)alkyl, difluoromethyl, difluoroethyl, hydroxy($C_{1-6}$)alkyl, $C_{1-6}$ alkoxy($C_{1-6}$)alkyl, $C_{1-6}$ alkylsulphinyl, amino($C_{1-6}$)-alkyl, $C_{1-6}$ alkylamino, hydroxy($C_{1-6}$)alkylamino, [($C_{1-6}$)alkoxy](hydroxy)($C_{1-6}$)alkylamino, [($C_{1-6}$)alkylthio](hydroxy)($C_{1-6}$)alkylamino, di($C_{1-6}$)alkylamino($C_{1-6}$)alkylamino, N-[di($C_{1-6}$)alkylamino($C_{1-6}$)alkyl]-N-[hydroxy($C_{1-6}$)alkyl]amino, hydroxy($C_{1-6}$)alkyl-($C_{3-7}$)cycloalkylamino, (hydroxy)[($C_{3-7}$)cycloalkyl($C_{1-6}$)alkyl]amino, ($C_{3-7}$)-heterocycloalkylamino, ($C_{3-7}$)heterocycloalkyl($C_{1-6}$)alkylamino, oxo($C_{3-7}$)-heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, $C_{2-6}$ alkylcarbonylamino, ($C_{2-6}$)alkylcarbonylamino-($C_{1-6}$)alkyl, N—[($C_{1-6}$)alkyl]-N—[($C_{2-6}$)alkylcarbonyl]amino, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]-amino, N-[carboxy($C_{1-6}$)alkyl]-N—[($C_{1-6}$)alkyl]amino, $C_{2-6}$ alkoxycarbonylamino, $C_{2-6}$ alkoxycarbonyl($C_{1-6}$)alkylamino, N—[($C_{1-6}$)alkyl]-N—[($C_{1-6}$)alkylsulphonyl]amino, ($C_{1-6}$)-alkylsulphonylamino($C_{1-6}$)alkyl, formyl, ($C_{3-7}$)cycloalkylcarbonyl, phenylcarbonyl, tetrazolyl($C_{1-6}$)alkyl, aminocarbonyl($C_{1-6}$)alkyl, $C_{1-6}$ alkylaminocarbonyl, hydroxy($C_{1-6}$)-alkylaminocarbonyl, di($C_{1-6}$)alkylaminocarbonyl and aminosulphonyl.

Selected examples of optional substituents on $R^1$ include one, two or three substituents independently selected from halogen, cyano, $C_{1-6}$ alkyl, hydroxy, $C_{1-6}$ alkoxy, $C_{1-6}$ alkylsulphonyl, oxo, $C_{2-6}$ alkylcarbonyl, carboxy, carboxy($C_{1-6}$)alkyl and $C_{2-6}$ alkoxycarbonyl. Additional examples include hydroxy($C_{1-6}$)alkyl, ($C_{3-7}$)heterocycloalkylamino, tetrazolyl($C_{1-6}$)alkyl, aminocarbonyl($C_{1-6}$)alkyl and aminosulphonyl.

Suitable examples of optional substituents on $R^1$ include one, two or three substituents independently selected from $C_{1-6}$ alkoxy and oxo.

Typical examples of particular substituents on $R^1$ include one, two or three substituents independently selected from fluoro, chloro, cyano, cyanoethyl, methyl, trifluoromethyl, trifluoroethyl, ethenyl, hydroxy, methoxy, isopropoxy, trifluoroethoxy, methylsulphonyl, methylsulphonylethyl, oxo, amino, dimethylamino, methoxyethylamino, N-(hydroxyethyl)-N-(methyl)amino, methylsulphonylamino, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl and methylsulphonylaminocarbonyl. Additional examples include ethyl, isopropyl, isobutyl, difluoromethyl, difluoroethyl, hydroxymethyl, hydroxyethyl, hydroxyisopropyl, methoxymethyl, methoxyethyl, methylsulphinyl, ethylamino, hydroxyethylamino, hydroxypropylamino, (hydroxy)-(methyl)propylamino, (hydroxy)(methoxy)(methyl)propylamino, (hydroxy)(methylthio)-butylamino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, tetrahydrofuranylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, ethenylcarbonylamino, bis(ethenylcarbonyl)amino, N-cyclopropylcarbonyl-N-methylamino, N-(carboxymethyl)-N-methylamino, N-(carboxyethyl)-N-methylamino, tert-butoxycarbonylamino, methoxycarbonylethylamino, N-methyl-N-(methylsulphonyl)amino, formyl, isopropylcarbonyl, cyclobutylcarbonyl, phenylcarbonyl, tetrazolylmethyl, aminocarbonylmethyl, methylaminocarbonyl, hydroxyethylaminocarbonyl, dimethylaminocarbonyl and aminosulphonyl.

Selected examples of particular substituents on $R^1$ include one, two or three substituents independently selected from fluoro, cyano, methyl, hydroxy, methoxy, methylsulphonyl, oxo, acetyl, carboxy, carboxymethyl, carboxyethyl, ethoxycarbonyl and tert-butoxycarbonyl. Additional examples include hydroxyisopropyl, tetrahydrofuranylamino, tetrazolylmethyl, aminocarbonylmethyl and aminosulphonyl.

Suitable examples of particular substituents on $R^1$ include one, two or three substituents independently selected from methoxy and oxo.

Selected values of $R^1$ include hydrogen, bromo, cyano, —$CO_2R^a$, methoxycarbonylethyl, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)-(methyl)pyridinyl, isopropoxypyridinyl, trifluoroethoxypyridinyl, (methyl)(trifluoroethoxy)pyridinyl, oxopyridinyl, (methyl)(oxo)pyridinyl, (dimethyl)(oxo)pyridinyl, aminopyridinyl, dimethylaminopyridinyl, methoxyethylaminopyridinyl, N-(hydroxyethyl)-N-(methyl)aminopyridinyl, methylsulphonylaminopyridinyl, carboxypyridinyl, quinolinyl, hydroxypyridazinyl, pyrimidinyl, methoxypyrimidinyl, oxopyrimidinyl, aminopyrimidinyl, dimethylaminopyrimidinyl, methoxyethylaminopyrimidinyl, hydroxypyrazinyl, pyrrolidinylmethylphenyl, piperazinylmethylphenyl, pyridinylpiperazinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)-pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, carboxypiperidinylpyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, dioxothiomorpholinylpyrimidinyl, oxodiazepanylpyrimidinyl, dioxothiadiazepanylpyrimidinyl, morpholinylmethylthienyl, morpholinylethylpyrazolyl, 2-oxa-5-azabicyclo[2.2.1]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl. Additional values include chloro, trifluoromethyl, —$OR^a$, —$SO_2R^a$, —$CONR^bR^c$ N-isopropylcarbonyl-N-methylaminomethyl, N-cyclopropylcarbonyl-N-methylaminomethyl, methylsulphinylphenyl, methylsulphonylphenyl, (methyl)(methylsulphonyl)phenyl, ethenylcarbonylaminophenyl, tert-butoxycarbonylaminophenyl, phenylcarbonylphenyl, aminosulphonylphenyl, methylsulphonylpiperidinyl, acetylpiperidinyl, isopropylcarbonylpiperidinyl, cyclobutylcarbonylpiperidinyl, methoxycarbonylpiperidinyl, tert-butoxycarbonylpiperidinyl, dihydropyranyl, dihydrothiopyranyl, methylsulphonyl-1,2,3,6-tetrahydropyridinyl, acetyl-1,2,3,6-tetrahydropyridinyl, methylsulphonyl-8-azabicyclo[3.2.1]octenyl, tert-butoxycarbonyl-8-azabicyclo[3.2.1]octenyl, methylthienyl, dihydrothieno[3,4-b][1,4]dioxinyl, oxoindolyl, oxodihydropyrrolo[3,4-b]pyridinyl, hydroxyisopropylpyridinyl, methylsulphonylpyridinyl, (difluoromethyl)(oxo)pyridinyl, (oxo)(trifluoromethyl)pyridinyl, (methoxy)(oxo)pyridinyl, acetylaminopyridinyl, bis(ethenylcarbonyl)aminopyridinyl, N-methyl-N-(methylsulphonyl)aminopyridinyl, formylpyridinyl, aminocarbonylpyridinyl, (aminocarbonyl)(methyl)pyridinyl, methylaminocarbonylpyridinyl, hydroxyethylaminocarbonylpyridinyl, dimethylaminocarbonylpyridinyl, (isopropyl)(methyl)pyrimidinyl, (isobutyl)(methyl)pyrimidinyl, hydroxyisopropylpyrimidinyl, (methoxymethyl)(methyl)pyrimidinyl, (methoxyethyl)-(methyl)pyrimidinyl, methylsulphonylpyrimidinyl, dioxopyrimidinyl, ethylaminopyrimidinyl, hydroxyethylaminopyrimidinyl, hydroxypropylaminopyrimidinyl, (hydroxy)(methyl)propylaminopyrimidinyl, (hydroxy)(methoxy)(methyl)propylaminopyrimidinyl, (hydroxy)(methylthio)butylaminopyrimidinyl, dimethylaminoethylaminopyrimidinyl, (dimethylamino)(methyl)propylaminopyrimidinyl, N-(dimethylaminoethyl)-N-(hydroxyethyl)aminopyrimidinyl, hydroxymethylcyclopentylaminopyrimidinyl, hydroxycyclobutylmethylaminopyrimidinyl, (cyclopropyl)(hydroxy)propylaminopyrimidinyl, tetrahydrofuranylaminopyrimidinyl, morpholinylethylaminopyrimidinyl, oxopyrrolidinylmethylaminopyrimidinyl, ethyloxadiazolylaminopyrimidinyl, methylthiadiazolylaminopyrimidinyl, thiazolylmethylaminopyrimidinyl, thiazolylethylaminopyrimidinyl, pyrimidinylmethylaminopyrimidinyl, methylpyrazolylmethylaminopyrimidinyl, acetylaminopyrimidinyl, N-acetyl-N-methylaminopyrimidinyl, N-(carboxymethyl)-N-methylaminopyrimidinyl, N-(carboxyethyl)-N-methylaminopyrimidinyl, methoxycarbonylethylaminopyrimidinyl, N-methyl-N-(methylsulphonyl)-aminopyrimidinyl, pyrazinyl, methylimidazolylmethyl, triazolylmethyl, methylpyridinylmethyl, methoxypyridinylmethyl, morpholinylmethylphenyl, (cyclopropyl)(methyl)-pyrimidinyl, hydroxycyclobutylpyrimidinyl, (cyclopentyl)(methyl)pyrimidinyl, carboxycyclohexylpyrimidinyl, carboxycyclohexenylpyrimidinyl, morpholinylthiazolyl, oxopyrrolidinylpyridinyl, dioxoisothiazolidinylpyridinyl, oxoimidazolidinylpyridinyl, (hydroxy)(methyl)piperidinylpyridinyl, carboxypiperidinylpyridinyl, (carboxy)(methyl)-piperidinylpyridinyl, (chloro)(piperazinyl)pyridinyl, difluoroethylpiperazinylpyridinyl, (methyl)(oxopiperazinyl)pyridinyl, (methyl)(morpholinyl)pyridinyl, oxomorpholinylpyridinyl, (methyl)(thiomorpholinyl)pyridinyl, (methyl)(oxothiomorpholinyl)pyridinyl, hydroxyoxetanylpyrimidinyl, hydroxyazetidinylpyrimidinyl, hydroxyethylazetidinylpyrimidinyl, (tert-butoxycarbonyl)(hydroxy)azetidinylpyrimidinyl, (methyl)-(tetrahydrofuranyl)pyrimidinyl, hydroxymethylpyrrolidinylpyrimidinyl, methoxypyrrolidinylpyrimidinyl, methoxymethylpyrrolidinylpyrimidinyl, oxopyrrolidinylpyrimidinyl, (methyl)(oxo)pyrrolidinylpyrimidinyl, dimethylaminopyrrolidinylpyrimidinyl, carboxypyrrolidinylpyrimidinyl, dioxoisothiazolidinylpyrimidinyl, hydroxytetrahydropyranylpyrimidinyl, difluoropiperidinylpyrimidinyl, hydroxypiperidinylpyrimidinyl, hydroxymethylpiperidinylpyrimidinyl, methoxypiperidinylpyrimidinyl, oxopiperidinylpyrimidinyl, (carboxy)(methyl)piperidinylpyrimidinyl, (carboxy)(hydroxy)piperidinylpyrimidinyl, (amino)(carboxy)piperidinylpyrimidinyl, (ethoxycarbonyl)(methyl)piperidinylpyrimidinyl, aminocarbonylpiperidinylpyrimidinyl, hydroxyethylpiperazinylpyrimidinyl, (methyl)(oxopiperazinyl)pyrimidinyl, carboxymethylpiperazinylpyrimidinyl, carboxyethylpiperazinylpyrimidinyl, tetrazolylmethylpiperazinylpyrimidinyl, aminocarbonylmethylpiperazinylpyrimidinyl, methylmorpholinylpyrimidinyl, dimethylmorpholinylpyrimidinyl, oxomorpholinylpyrimidinyl, hydroxymethylazetidinylcarbonylpyridinyl, piperazinylcarbonylpyridinyl, methylpiperazinylcarbonylpyridinyl, morpholinylcarbonylpyridinyl, thiomorpholinylcarbonylpyridinyl, dioxothiomorpholinylcarbonylpyridinyl, (methyl)(morpholinylmethyl)-pyrimidinyl, carboxy-3- azabicyclo[3.1.0]hexanylpyrimidinyl, ethoxycarbonyl-3-azabicyclo[3.1.0]hexanylpyrimidinyl, carboxy-3-azabicyclo[4.1.0]heptanylpyrimidinyl, carboxy-3-azabicyclo[3.2.1]octanylpyrimidinyl, methoxycarbonyl-3-azabicyclo[3.2.1]-octanylpyrimidinyl, oxo-3,6-diazabicyclo[3.2.2]nonanylpyrimidinyl, oxo-2-oxa-6-azaspiro[3.4]octanylpyridinyl, difluoro-5-azaspiro[2.4]heptanylpyrimidinyl, carboxy-2-azaspiro[3.3]heptanylpyrimidinyl and 7-oxa-2-azaspiro[3.5]nonanylpyrimidinyl.

Definitive values of $R^1$ include bromo, tert-butoxycarbonyl-1,2,3,6-tetrahydropyridinyl, methylpyrazolyl, cyanopyridinyl, methoxypyridinyl, oxopyridinyl, piperazinylpyridinyl, morpholinylpyridinyl, carboxypiperidinylpyrimidinyl, piperazinylpyrimidinyl, methylsulphonylpiperazinylpyrimidinyl, oxopiperazinylpyrimidinyl, oxodiazepanylpyrimidinyl and 2-oxa-6-azaspiro[3.3]heptanylpyrimidinyl. Additional values include aminosulphonylphenyl, methylsulphonylpiperidinyl, acetylpiperidinyl, tert-butoxycarbonylpiperidinyl, dihydropyranyl, dihydrothiopyranyl, methylsulphonyl-1,2,3,6-tetrahydropyridinyl, acetyl-1,2,3,6-tetrahydropyridinyl, methylsulphonyl-8-azabicyclo[3.2.1]octenyl, tert-butoxycarbonyl-8-azabicyclo[3.2.1]octenyl, oxoindolyl, hydroxyisopropylpyrimidinyl, tetrahydrofuranylaminopyrimidinyl, carboxycyclohexylpyrimidinyl, morpholinylthiazolyl, carboxypiperidinylpyridinyl, (carboxy)(methyl)-piperidinylpyridinyl, (methyl)(oxopiperazinyl)pyridinyl, methoxypyrrolidinylpyrimidinyl, carboxypyrrolidinylpyrimidinyl, difluoropiperidinylpyrimidinyl, (carboxy)(methyl)-piperidinylpyrimidinyl, (carboxy)(hydroxy)piperidinylpyrimidinyl, (ethoxycarbonyl)-(methyl)piperidinylpyrimidinyl, carboxymethylpiperazinylpyrimidinyl, carboxyethylpiperazinylpyrimidinyl, tetrazolylmethylpiperazinylpyrimidinyl, aminocarbonylmethylpiperazinylpyrimidinyl, dimethylmorpholinylpyrimidinyl, carboxy-3-azabicyclo[3.1.0]-hexanylpyrimidinyl, ethoxycarbonyl-3-azabicyclo[3.1.0]hexanylpyrimidinyl, carboxy-3-azabicyclo[4.1.0]heptanylpyrimidinyl, oxo-3,6-diazabicyclo[3.2.2]nonanylpyrimidinyl and carboxy-2-azaspiro[3.3]heptanylpyrimidinyl.

Illustrative values of $R^1$ include methoxypyridinyl, oxopyridinyl, piperazinylpyrimidinyl, oxopiperazinylpyrimidinyl and oxodiazepanylpyrimidinyl.

Typically, $R^2$ represents hydrogen, halogen or optionally substituted $C_{1-6}$ alkyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In a third embodiment, $R^2$ represents optionally substituted $C_{1-6}$ alkyl. In one aspect of that embodiment, $R^2$ represents monosubstituted methyl or monosubstituted ethyl.

Selected values of $R^2$ include hydrogen, fluoro and ethoxycarbonylethyl.

In a particular embodiment, $R^3$ represents hydrogen.

Suitably, $R^4$ represents hydrogen or methyl.

In a first embodiment, $R^4$ represents hydrogen. In a second embodiment, $R^4$ represents $C_{1-6}$ alkyl, especially methyl.

Suitably, $R^5$ represents hydrogen, methyl or ethyl.

In a first embodiment, $R^5$ represents hydrogen. In a second embodiment, $R^5$ represents $C_{1-6}$ alkyl, especially methyl or ethyl. In one aspect of that embodiment, $R^5$ represents methyl. In another aspect of that embodiment, $R^5$ represents ethyl.

Typical examples of suitable substituents on $R^aR^b$, —$R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylamino carbonyl.

Typical examples of specific substituents on $R^a$, $R^b$, $R^c$, $R^d$, or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-$(C_{1-6})$ alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy$(C_{1-6})$alkyl, amino$(C_{1-6})$alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino $(C_{1-6})$alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, amino azetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxooxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts and solvates thereof, and glucuronide derivatives thereof, and co-crystals thereof:

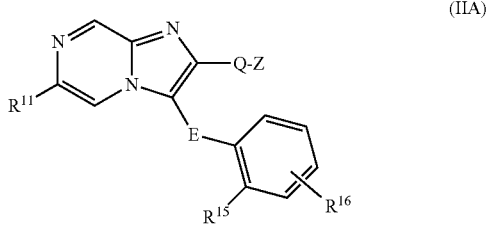

(IIA)

wherein $R^{11}$ represents halogen or cyano; or $C_{1-6}$ alkyl, aryl, $C_{3-7}$ heterocycloalkyl, $C_{3-7}$ heterocycloalkenyl, $(C_{4-9})$heterobicycloalkenyl, heteroaryl, $(C_{3-7})$heterocycloalkyl$(C_{1-6})$-alkyl-aryl-, heteroaryl-$(C_{3-7})$heterocycloalkyl-, $(C_{3-7})$cycloalkyl-heteroaryl-, $(C_{4-7})$cycloalkenyl-heteroaryl-, $(C_{3-7})$heterocycloalkyl-heteroaryl-, $(C_{3-7})$heterocycloalkyl-$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents;

$R^{15}$ and $R^{16}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; and E, Q and Z are as defined above.

Suitably, $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$heterocycloalkyl-, $(C_{4-7})$cycloalkenyl-heteroaryl-, $(C_{3-7})$-heterocycloalkyl-heteroaryl-, $(C_{3-7})$heterocycloalkyl($C_{1-6}$)alkyl-heteroaryl-, $(C_{3-7})$-heterocycloalkenyl-heteroaryl-, $(C_{4-9})$heterobicycloalkyl-heteroaryl- or $(C_{4-9})$-spiroheterocycloalkyl-heteroaryl-, any of which groups may be optionally substituted by one or more substituents.

Aptly, $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$heterocycloalkyl-, $(C_{3-7})$heterocycloalkyl-heteroaryl-, $(C_{3-7})$heterocycloalkyl-$(C_{1-6})$alkyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^{11}$ may represent $(C_{4-9})$heterobicycloalkenyl- or $(C_{3-7})$-cycloalkyl-heteroaryl-, either of which groups may be optionally substituted by one or more substituents.

Examples of optional substituents which may be present on $R^{11}$ include one, two or three substituents independently selected from halogen, cyano, cyano($C_{1-6}$)alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy ($C_{1-6}$)alkyl, $C_{1-6}$ alkylthio, $C_{1-6}$ alkylsulphonyl, ($C_{1-6}$)alkylsulphonyl($C_{1-6}$) alkyl, oxo, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, $C_{2-6}$ alkylcarbonylamino, $C_{2-6}$ alkoxycarbonylamino, $C_{1-6}$ alkylaminocarbonyl-amino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl, aminocarbonyl, $C_{1-6}$ alkylaminocarbonyl, di($C_{1-6}$)alkylaminocarbonyl, $C_{1-6}$ alkylsulphonylamino carbonyl, aminosulphonyl, $C_{1-6}$ alkylaminosulphonyl and di($C_{1-6}$)alkylaminosulphonyl. Additional examples include difluoromethyl, difluoroethyl, hydroxy($C_{1-6}$)alkyl, $C_{1-6}$ alkylsulphinyl, hydroxy($C_{1-6}$)alkylamino, [($C_{1-6}$)alkoxy](hydroxy)($C_{1-6}$)alkylamino, [($C_{1-6}$) alkylthio]-(hydroxy)($C_{1-6}$)alkylamino, di($C_{1-6}$)alkylamino ($C_{1-6}$)alkylamino, N-[di($C_{1-6}$)alkylamino-($C_{1-6}$)alkyl]-N-[hydroxy($C_{1-6}$)alkyl]amino, hydroxy($C_{1-6}$)alkyl($C_{3-7}$) cycloalkylamino, (hydroxy)[($C_{3-7}$)cycloalkyl($C_{1-6}$)alkyl] amino, ($C_{3-7}$)heterocycloalkylamino, ($C_{3-7}$)-heterocycloalkyl($C_{1-6}$)alkylamino, oxo($C_{3-7}$) heterocycloalkyl($C_{1-6}$)alkylamino, ($C_{1-6}$) alkylheteroarylamino, heteroaryl($C_{1-6}$)alkylamino, ($C_{1-6}$) alkylheteroaryl($C_{1-6}$)alkylamino, N—[($C_{1-6}$)alkyl]-N—[($C_{2-6}$)alkylcarbonyl]amino, $C_{3-6}$ alkenylcarbonylamino, bis [($C_{3-6}$)alkenylcarbonyl]amino, N—[($C_{1-6}$)alkyl]-N—[($C_{3-7}$) cycloalkylcarbonyl]amino, N-[carboxy($C_{1-6}$)-alkyl]-N—[($C_{1-6}$)alkyl]amino, $C_{2-6}$ alkoxycarbonyl($C_{1-6}$)alkylamino, N—[($C_{1-6}$)-alkyl]-N—[($C_{1-6}$)alkylsulphonyl]amino, ($C_{3-7}$) cycloalkylcarbonyl, phenylcarbonyl, tetrazolyl($C_{1-6}$)-alkyl, aminocarbonyl($C_{1-6}$)alkyl and hydroxy($C_{1-6}$)alkylaminocarbonyl.

Suitable examples of optional substituents which may be present on $R^{11}$ include one, two or three substituents independently selected from halogen, cyano, $C_{1-6}$ alkyl, hydroxy, $C_{1-6}$ alkoxy, $C_{1-6}$ alkylsulphonyl, oxo, $C_{2-6}$ alkylcarbonyl, carboxy, carboxy($C_{1-6}$)-alkyl, $C_{2-6}$ alkoxycarbonyl and aminosulphonyl. Additional examples include hydroxy-($C_{1-6}$)alkyl, ($C_{3-7}$)heterocycloalkylamino, tetrazolyl($C_{1-6}$) alkyl and aminocarbonyl($C_{1-6}$)-alkyl.

Examples of particular substituents on $R^{11}$ include fluoro, chloro, bromo, cyano, cyanoethyl, nitro, methyl, ethyl, tert-butyl, trifluoromethyl, trifluoroethyl, ethenyl, hydroxy, methoxy, isopropoxy, difluoromethoxy, trifluoromethoxy, trifluoroethoxy, methylenedioxy, ethylenedioxy, methoxymethyl, methylthio, methylsulphonyl, methylsulphonylethyl, oxo, amino, methylamino, dimethylamino, methoxyethylamino, N-(hydroxyethyl)-N-(methyl)amino, acetylamino, methoxycarbonylamino, ethoxycarbonylamino, ethylaminocarbonylamino, butylaminocarbonylamino, methylsulphonylamino, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl, methylaminocarbonyl, dimethylaminocarbonyl, methylsulphonylaminocarbonyl, aminosulphonyl, methylaminosulphonyl and dimethylaminosulphonyl. Additional examples include isopropyl, isobutyl, difluoromethyl, difluoroethyl, hydroxymethyl, hydroxyethyl, hydroxyisopropyl, methoxyethyl, methylsulphinyl, ethylamino, hydroxyethylamino, hydroxypropylamino, (hydroxy)(methyl)propylamino, (hydroxy)-(methoxy)(methyl)propylamino, (hydroxy)(methylthio)butylamino, dimethylaminoethylamino, (dimethylamino)(methyl)propylamino, N-(dimethylaminoethyl)-N-(hydroxyethyl)-amino, hydroxymethylcyclopentylamino, hydroxycyclobutylmethylamino, (cyclopropyl)-(hydroxy)propylamino, tetrahydrofuranylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, N-acetyl-N-methylamino, N-isopropylcarbonyl-N-methylamino, ethenylcarbonylamino, bis(ethenylcarbonyl)amino, N-cyclopropylcarbonyl-N-methylamino, N-(carboxymethyl)-N-methylamino, N-(carboxyethyl)-N-methylamino, tert-butoxycarbonylamino, methoxycarbonylethylamino, N-methyl-N-(methylsulphonyl)amino, isopropylcarbonyl, cyclobutylcarbonyl, phenylcarbonyl, tetrazolylmethyl, aminocarbonylmethyl and hydroxyethylaminocarbonyl.

Suitable examples of particular substituents on $R^{11}$ include fluoro, cyano, methyl, hydroxy, methoxy, methylsulphonyl, oxo, acetyl, carboxy, carboxymethyl, carboxyethyl, ethoxycarbonyl, tert-butoxycarbonyl and aminosulphonyl. Additional examples include hydroxyisopropyl, tetrahydrofuranylamino, tetrazolylmethyl and aminocarbonylmethyl.

Generally, $R^{11}$ represents $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl-$(C_{3-7})$heterocycloalkyl-, $(C_{4-7})$cycloalkenyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^{11}$ may represent $(C_{4-9})$heterobicycloalkenyl- or $(C_{3-7})$cycloalkyl-heteroaryl-, either of which groups may be optionally substituted by one or more substituents. Additionally, $R^{11}$ may represent halogen.

More generally, $R^{11}$ represents $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl-$(C_{3-7})$heterocycloalkyl-, $(C_{3-7})$heterocycloalkyl-heteroaryl-, $(C_{3-7})$heterocycloalkyl-$(C_{1-6})$alkyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^{11}$ may represent $(C_{4-9})$heterobicycloalkenyl- or $(C_{3-7})$-cycloalkyl-heteroaryl-, either of which groups may be optionally substituted by one or more substituents. Additionally, $R^{11}$ may represent halogen.

Still more generally, $R^{11}$ represents halogen; or aryl, $C_{3-7}$ heterocycloalkyl, $C_{3-7}$ heterocycloalkenyl, $(C_{4-9})$heterobicycloalkenyl-, heteroaryl, $(C_{3-7})$cycloalkyl-heteroaryl-, $(C_{3-7})$heterocycloalkyl-heteroaryl-, $(C_{4-9})$heterobicycloalkyl-heteroaryl- or $(C_{4-9})$-spiroheterocycloalkyl-heteroaryl-, any of which groups may be optionally substituted by one or more substituents.

Even more generally, $R^{11}$ represents heteroaryl or $(C_{3-7})$heterocycloalkyl-heteroaryl-, either of which groups may be optionally substituted by one or more substituents. Additionally, $R^{11}$ may represent aryl, $C_{3-7}$ heterocycloalkyl, $C_{3-7}$ heterocycloalkenyl, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^{11}$ may represent halogen.

In a first embodiment, $R^{11}$ represents halogen. In one aspect of that embodiment, $R^{11}$ represents bromo.

In a second embodiment, $R^{11}$ represents cyano.

In a third embodiment, $R^{11}$ represents optionally substituted $C_{1-6}$ alkyl. In one aspect of that embodiment, $R^{11}$ represents optionally substituted ethyl.

In a fourth embodiment, $R^{11}$ represents optionally substituted aryl. In one aspect of that embodiment, $R^{11}$ represents optionally substituted phenyl.

In a fifth embodiment, $R^{11}$ represents optionally substituted $C_{3-7}$ heterocycloalkyl.

In one aspect of that embodiment, $R^{11}$ represents optionally substituted piperidinyl.

In a sixth embodiment, $R^{11}$ represents optionally substituted $C_{3-7}$ heterocycloalkenyl. In a first aspect of that embodiment, $R^{11}$ represents optionally substituted dihydropyranyl. In a second aspect of that embodiment, $R^{11}$ represents optionally substituted dihydrothiopyranyl. In a third aspect of that embodiment, $R^{11}$ represents optionally substituted 1,2,3,6-tetrahydropyridinyl.

In a seventh embodiment, $R^{11}$ represents optionally substituted $(C_{4-9})$-heterobicycloalkenyl-. In one aspect of that embodiment, $R^{11}$ represents optionally substituted 8-azabicyclo[3.2.1]octenyl.

In an eighth embodiment, $R^{11}$ represents optionally substituted heteroaryl. In selected aspects of that embodiment, $R^{11}$ represents benzofuryl, thienyl, indolyl, pyrazolyl, indazolyl, isoxazolyl, imidazolyl, pyridinyl, quinolinyl, pyridazinyl, pyrimidinyl or pyrazinyl, any of which groups may be optionally substituted by one or more substituents.

In a ninth embodiment, $R^{11}$ represents optionally substituted $(C_{3-7})$heterocycloalkyl$(C_{1-6})$alkyl-aryl-. In a first aspect of that embodiment, $R^{11}$ represents optionally substituted pyrrolidinylmethylphenyl-. In a second aspect of that embodiment, $R^{11}$ represents optionally substituted piperazinylmethylphenyl-.

In a tenth embodiment, $R^{11}$ represents optionally substituted heteroaryl$(C_{3-7})$-heterocycloalkyl-. In one aspect of that embodiment, $R^{11}$ represents optionally substituted pyridinylpiperazinyl-.

In an eleventh embodiment, $R^{11}$ represents optionally substituted $(C_{3-7})$cycloalkyl-heteroaryl-. In one aspect of that embodiment, $R^{11}$ represents optionally substituted cyclohexylpyrimidinyl-.

In a twelfth embodiment, $R^{11}$ represents optionally substituted $(C_{4-7})$cycloalkenyl-heteroaryl-.

In a thirteenth embodiment, $R^{11}$ represents optionally substituted $(C_{3-7})$-heterocycloalkyl-heteroaryl-. In a first aspect of that embodiment, $R^{11}$ represents optionally substituted morpholinylthiazolyl-. In a second aspect of that embodiment, $R^{11}$ represents optionally substituted pyrrolidinylpyridinyl-. In a third aspect of that embodiment, $R^{11}$ represents optionally substituted piperidinylpyridinyl-. In a fourth aspect of that embodiment, $R^{11}$ represents optionally substituted piperazinylpyridinyl-. In a fifth aspect of that embodiment, $R^{11}$ represents optionally substituted morpholinylpyridinyl-. In a sixth aspect of that embodiment, $R^{11}$ represents optionally substituted thiomorpholinylpyridinyl-. In a seventh aspect of that embodiment, $R^{11}$ represents optionally substituted diazepanylpyridinyl-. In an eighth aspect of that embodiment, $R^{11}$ represents optionally substituted pyrrolidinylpyrimidinyl-. In a ninth aspect of that embodiment, $R^{11}$ represents optionally substituted piperidinylpyrimidinyl-. In a tenth aspect of that embodiment, $R^{11}$ represents optionally substituted piperazinylpyrimidinyl-.

In an eleventh aspect of that embodiment, $R^{11}$ represents optionally substituted morpholinylpyrimidinyl-. In a twelfth aspect of that embodiment, $R^{11}$ represents optionally substituted thiomorpholinylpyrimidinyl-. In a thirteenth aspect of that embodiment, $R^{11}$ represents optionally substituted diazepanylpyrimidinyl-. In a fourteenth aspect of that embodiment, $R^{11}$ represents optionally substituted thiadiazepanylpyrimidinyl-.

In a fourteenth embodiment, $R^{11}$ represents optionally substituted $(C_{3-7})$-heterocycloalkyl$(C_{1-6})$alkyl-heteroaryl-. In a first aspect of that embodiment, $R^{11}$ represents optionally substituted morpholinylmethylthienyl-. In a second aspect of that embodiment, $R^{11}$ represents optionally substituted morpholinylethylpyrazolyl-.

In a fifteenth embodiment, $R^{11}$ represents optionally substituted $(C_{3-7})$-heterocycloalkenyl-heteroaryl-.

In a sixteenth embodiment, $R^{11}$ represents optionally substituted $(C_{4-9})$-heterobicycloalkyl-heteroaryl-.

In a seventeenth embodiment, $R^{11}$ represents optionally substituted $(C_{4-9})$-spiroheterocycloalkyl-heteroaryl-.

Appositely, $R^{11}$ represents bromo or cyano; or ethyl, phenyl, piperidinyl, piperazinyl, morpholinyl, 1,2,3,6-tetrahydropyridinyl, benzofuryl, thienyl, indolyl, pyrazolyl, indazolyl, isoxazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, pyrrolidinylpyridinyl, piperidinylpyridinyl, piperazinylpyridinyl, morpholinylpyridinyl, thiomorpholinylpyridinyl, diazepanylpyridinyl, pyrrolidinylpyrimidinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl, morpholinylmethylthienyl, morpholinylethylpyrazolyl, 2-oxa-5-azabicyclo[2.2.1]-heptanylpyrimidinyl, 2-oxa-6-azaspiro[3.3]heptanylpyrimidinyl, 2-oxa-6-azaspiro[3.4]-octanylpyrimidinyl, 2-oxa-6-azaspiro[3.5]nonanylpyrimidinyl or 2-oxa-7-azaspiro[3.5]-nonanylpyrimidinyl, any of which groups may be optionally substituted by one or more substituents. Additionally, $R^{11}$ may represent chloro, trifluoromethyl, —$OR^a$, —$SO_2R^a$ or —$CONR^bR^c$; or methyl, dihydropyranyl, dihydrothiopyranyl, 8-azabicyclo[3.2.1]octenyl, dihydrothieno[3,4-b][1,4]dioxinyl, dihydropyrrolo[3,4-b]pyridinyl, imidazolylmethyl, triazolylmethyl, pyridinylmethyl, morpholinylmethylphenyl, cyclopropylpyrimidinyl, cyclobutylpyrimidinyl, cyclopentylpyrimidinyl, cyclohexylpyrimidinyl, cyclohexenyl-pyrimidinyl, morpholinylthiazolyl, azetidinylpyridinyl, isothiazolidinylpyridinyl, imidazolidinylpyridinyl, oxetanylpyrimidinyl, azetidinylpyrimidinyl, tetrahydrofuranyl-pyrimidinyl, isothiazolidinylpyrimidinyl, tetrahydropyranylpyrimidinyl, azetidinylmethyl-pyridinyl, piperazinylmethylpyridinyl, morpholinylmethylpyridinyl, thiomorpholinyl-methylpyridinyl, morpholinylmethylpyrimidinyl, 3-azabicyclo[3.1.0]hexanylpyrimidinyl, 3-azabicyclo[4.1.0]heptanylpyrimidinyl, 3-azabicyclo[3.2.1]octanylpyrimidinyl, 3,6-diazabicyclo[3.2.2]nonanylpyrimidinyl, 2-oxa-6-azaspiro[3.4]octanylpyridinyl, 2-azaspiro[3.3]heptanylpyrimidinyl, 5-azaspiro[2.4]heptanylpyrimidinyl or 7-oxa-2-azaspiro[3.5]nonanylpyrimidinyl, any of which groups may be optionally substituted by one or more substituents.

Definitively, $R^{11}$ represents bromo; or phenyl, piperidinyl, dihydropyranyl, dihydrothiopyranyl, 1,2,3,6-tetrahydropyridinyl, 8-azabicyclo[3.2.1]octenyl, indolyl, pyrazolyl, pyridinyl, pyrimidinyl, cyclohexylpyrimidinyl, morpholinylthiazolyl, piperidinylpyridinyl, piperazinylpyridinyl, morpholinylpyridinyl, pyrrolidinylpyridinyl, piperidinylpyrimidinyl, piperazinylpyrimidinyl, morpholinylpyrimidinyl, diazepanylpyrimidinyl, 3-azabicyclo[3.1.0]hexanylpyrimidinyl, 3-azabicyclo[4.1.0]heptanylpyrimidinyl, 3,6-diazabicyclo[3.2.2]nonanylpyrimidinyl, 2-azaspiro[3.3]heptanylpyrimidinyl or 2-oxa-6-azaspiro[3.3]heptanylpyrimidinyl, any of which groups may be optionally substituted by one or more substituents.

Illustratively, $R^{11}$ represents pyridinyl, piperazinylpyrimidinyl or diazepanylpyrimidinyl, any of which groups may be optionally substituted by one or more substituents.

Typical examples of optional substituents on $R^{11}$ include one, two or three substituents independently selected from halogen, cyano, cyano$(C_{1-6})$alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, $(C_{1-6})$alkylsulphonyl$(C_{1-6})$alkyl, oxo, amino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $C_{1-6}$ alkylsulphonylamino, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, tetrazolyl, aminocarbonyl and $C_{1-6}$ alkylsulphonylaminocarbonyl. Additional examples include difluoromethyl, difluoroethyl, hydroxy$(C_{1-6})$alkyl, $C_{1-6}$ alkoxy$(C_{1-6})$alkyl, $C_{1-6}$ alkylsulphinyl, $C_{1-6}$ alkylamino, hydroxy$(C_{1-6})$alkylamino, [$(C_{1-6})$alkoxy](hydroxy)$(C_{1-6})$alkylamino, [$(C_{1-6})$alkylthio]-(hydroxy)$(C_{1-6})$alkylamino, di$(C_{1-6})$alkylamino$(C_{1-6})$alkylamino, N-[di$(C_{1-6})$alkylamino-$(C_{1-6})$alkyl]-N-[hydroxy$(C_{1-6})$alkyl]amino, hydroxy$(C_{1-6})$alkyl$(C_{3-7})$cycloalkylamino, (hydroxy)[$(C_{3-7})$cycloalkyl$(C_{1-6})$alkyl]amino, $(C_{3-7})$heterocycloalkylamino, $(C_{3-7})$-heterocycloalkyl$(C_{1-6})$alkylamino, oxo$(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkylamino, $C_{2-6}$ alkylcarbonylamino, N—[$(C_{1-6})$alkyl]-N—[$(C_{2-6})$alkylcarbonyl]amino, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]-amino, N-[carboxy$(C_{1-6})$alkyl]-N—[$(C_{1-6})$alkyl]amino, $C_{2-6}$ alkoxycarbonylamino, $C_{2-6}$ alkoxycarbonyl$(C_{1-6})$alkylamino, N—[$(C_{1-6})$alkyl]-N—[$(C_{1-6})$alkylsulphonyl]amino, formyl, $(C_{3-7})$cycloalkylcarbonyl, phenylcarbonyl, tetrazolyl$(C_{1-6})$alkyl, aminocarbonyl$(C_{1-6})$alkyl, $C_{1-6}$ alkylaminocarbonyl, hydroxy$(C_{1-6})$alkylaminocarbonyl, di$(C_{1-6})$alkylaminocarbonyl and aminosulphonyl.

Selected examples of optional substituents on $R^1$ include one, two or three substituents independently selected from halogen, cyano, $C_{1-6}$ alkyl, hydroxy, $C_{1-6}$ alkoxy, $C_{1-6}$ alkylsulphonyl, oxo, $C_{2-6}$ alkylcarbonyl, carboxy, carboxy$(C_{1-6})$alkyl and $C_{2-6}$ alkoxycarbonyl. Additional examples include hydroxy$(C_{1-6})$alkyl, $(C_{3-7})$heterocycloalkylamino, tetrazolyl$(C_{1-6})$alkyl, aminocarbonyl$(C_{1-6})$alkyl and aminosulphonyl.

Suitable examples of optional substituents on $R^{11}$ include one, two or three substituents independently selected from $C_{1-6}$ alkoxy and oxo.

Typical examples of particular substituents on $R^{11}$ include one, two or three substituents independently selected from fluoro, chloro, cyano, cyanoethyl, methyl, trifluoromethyl, trifluoroethyl, ethenyl, hydroxy, methoxy, isopropoxy, trifluoroethoxy, methylsulphonyl, methylsulphonylethyl, oxo, amino, dimethylamino, methoxyethylamino, N-(hydroxyethyl)-N-(methyl)amino, methylsulphonylamino, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl and methylsulphonylaminocarbonyl. Additional examples include ethyl, isopropyl, isobutyl, difluoromethyl, difluoroethyl, hydroxymethyl, hydroxyethyl, hydroxyisopropyl, methoxymethyl, methoxyethyl, methylsulphinyl, ethylamino, hydroxyethylamino, hydroxypropylamino, (hydroxy)-(methyl)propylamino, (hydroxy)(methoxy)(methyl) propylamino, (hydroxy)(methylthio)-butylamino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, tetrahydrofuranylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, ethenylcarbonylamino, bis(ethenylcarbonyl)amino, N-cyclopropylcarbonyl-N-methylamino, N-(carboxymethyl)-N-methylamino, N-(carboxyethyl)-N-methylamino, tert-butoxycarbonylamino, methoxycarbonylethylamino, N-methyl-N-(methylsulphonyl)amino, formyl, isopropylcarbonyl, cyclobutylcarbonyl, phenylcarbonyl, tetrazolylmethyl, amino carbonylmethyl, methylaminocarbonyl, hydroxyethylaminocarbonyl, dimethylaminocarbonyl and aminosulphonyl.

Selected examples of particular substituents on $R^{11}$ include one, two or three substituents independently selected from fluoro, cyano, methyl, hydroxy, methoxy, methylsulphonyl, oxo, acetyl, carboxy, carboxymethyl, carboxyethyl, ethoxycarbonyl and tert-butoxycarbonyl. Additional examples include hydroxyisopropyl, tetrahydrofuranylamino, tetrazolylmethyl, amino carbonylmethyl and aminosulphonyl.

Suitable examples of particular substituents on $R^{11}$ include one, two or three substituents independently selected from methoxy and oxo.

Selected values of $R^{11}$ include bromo, cyano, methoxycarbonylethyl, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)(methyl)-pyridinyl, isopropoxypyridinyl, trifluoroethoxypyridinyl, (methyl)(trifluoroethoxy)-pyridinyl, oxopyridinyl, (methyl)(oxo)pyridinyl, (dimethyl)(oxo) pyridinyl, aminopyridinyl, dimethylaminopyridinyl, methoxyethylaminopyridinyl, N-(hydroxyethyl)-N-(methyl)aminopyridinyl, methylsulphonylaminopyridinyl, carboxypyridinyl, quinolinyl, hydroxypyridazinyl, pyrimidinyl, methoxypyrimidinyl, oxopyrimidinyl, aminopyrimidinyl, dimethylaminopyrimidinyl, methoxyethylaminopyrimidinyl, hydroxypyrazinyl, pyrrolidinylmethylphenyl, piperazinylmethylphenyl, pyridinylpiperazinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, carboxypiperidinylpyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, dioxothiomorpholinylpyrimidinyl, oxodiazepanylpyrimidinyl, dioxothiadiazepanylpyrimidinyl, morpholinylmethylthienyl, morpholinylethylpyrazolyl, 2-oxa-5-azabicyclo[2.2.1]heptanylpyrimidinyl, 2-oxa-6-azaspiro[3.3]-heptanylpyrimidinyl, 2-oxa-6-azaspiro[3.4]octanylpyrimidinyl, 2-oxa-6-azaspiro[3.5]-nonanylpyrimidinyl and 2-oxa-7-azaspiro[3.5]nonanylpyrimidinyl. Additional values include chloro, N-isopropylcarbonyl-N-methylaminomethyl, N-cyclopropylcarbonyl-N-methylaminomethyl, methylsulphinylphenyl, methylsulphonylphenyl, (methyl)-(methylsulphonyl)phenyl, ethenylcarbonylaminophenyl, tert-butoxycarbonylaminophenyl, phenylcarbonylphenyl, aminosulphonylphenyl, methylsulphonylpiperidinyl, acetylpiperidinyl, isopropylcarbonylpiperidinyl, cyclobutylcarbonylpiperidinyl, methoxycarbonylpiperidinyl, tert-butoxycarbonylpiperidinyl, dihydropyranyl, dihydrothiopyranyl, methylsulphonyl-1,2,3,6-tetrahydropyridinyl, acetyl-1,2,3,6-tetrahydropyridinyl, methylsulphonyl-8-azabicyclo[3.2.1]octenyl, tert-butoxycarbonyl-8-azabicyclo[3.2.1]octenyl, methylthienyl, dihydrothieno[3,4-b][1,4]dioxinyl, oxoindolyl, oxodihydropyrrolo[3,4-b]pyridinyl, hydroxyisopropylpyridinyl, methylsulphonylpyridinyl, (difluoromethyl)(oxo)pyridinyl, (oxo)(trifluoromethyl)pyridinyl, (methoxy)-(oxo)pyridinyl, acetylaminopyridinyl, bis(ethenylcarbonyl)aminopyridinyl, N-methyl-N-(methylsulphonyl)aminopyridinyl, formylpyridinyl, aminocarbonylpyridinyl, (aminocarbonyl)(methyl)pyridinyl, methylaminocarbonylpyridinyl, hydroxyethylaminocarbonylpyridinyl, dimethylaminocarbonylpyridinyl, (isopropyl)(methyl)pyrimidinyl, (isobutyl)(methyl)pyrimidinyl, hydroxyisopropylpyrimidinyl, (methoxymethyl)(methyl)-pyrimidinyl, (methoxyethyl)(methyl)pyrimidinyl, methylsulphonylpyrimidinyl, dioxopyrimidinyl, ethylaminopyrimidinyl, hydroxyethylaminopyrimidinyl, hydroxypropylaminopyrimidinyl, (hydroxy)(methyl)propylaminopyrimidinyl, (hydroxy)-(methoxy)(methyl)propylaminopyrimidinyl, (hydroxy)(methylthio)butylaminopyrimidinyl, dimethylaminoethylaminopyrimidinyl, (dimethylamino)(methyl)propylaminopyrimidinyl, N-(dimethylaminoethyl)-N-(hydroxyethyl)aminopyrimidinyl, hydroxymethylcyclopentylaminopyrimidinyl, hydroxycyclobutylmethylaminopyrimidinyl, (cyclopropyl)(hydroxy) propylaminopyrimidinyl, tetrahydrofuranylaminopyrimidinyl, morpholinylethylaminopyrimidinyl, oxopyrrolidinylmethylaminopyrimidinyl, ethyloxadiazolylaminopyrimidinyl, methylthiadiazolylaminopyrimidinyl, thiazolylmethylaminopyrimidinyl, thiazolylethylaminopyrimidinyl, pyrimidinylmethylaminopyrimidinyl, methylpyrazolylmethylaminopyrimidinyl, acetylaminopyrimidinyl, N-acetyl-N-methylaminopyrimidinyl, N-(carboxymethyl)-N-methylaminopyrimidinyl, N-(carboxyethyl)-N-methylaminopyrimidinyl, methoxycarbonylethylaminopyrimidinyl, N-methyl-N-(methylsulphonyl)aminopyrimidinyl, pyrazinyl, methylimidazolylmethyl, triazolylmethyl, methylpyridinylmethyl, methoxypyridinylmethyl, morpholinylmethylphenyl, (cyclopropyl)(methyl)pyrimidinyl, hydroxycyclobutylpyrimidinyl, (cyclopentyl)-(methyl)pyrimidinyl, carboxycyclobutylpyrimidinyl, carboxycyclohexenylpyrimidinyl, morpholinylthiazolyl, oxopyrrolidinylpyrimidinyl, dioxoisothiazolidinylpyridinyl, oxoimidazolidinylpyridinyl, (hydroxy)(methyl)piperidinylpyridinyl, carboxypiperidinylpyridinyl, (carboxy)(methyl)piperidinylpyridinyl, (chloro)(piperazinyl)pyridinyl, difluoroethylpiperazinylpyridinyl, (methyl)(oxopiperazinyl)pyridinyl, (methyl)-(morpholinyl)pyridinyl, oxomorpholinylpyridinyl, (methyl)(thiomorpholinyl)pyridinyl, (methyl)(oxothiomorpholinyl)pyridinyl, hydroxyoxetanylpyrimidinyl, hydroxyazetidinylpyrimidinyl, hydroxymethylazetidinylpyrimidinyl, (tert-butoxycarbonyl)(hydroxy)-azetidinylpyrimidinyl, (methyl)(tetrahydrofuranyl)pyrimidinyl, hydroxymethylpyrrolidinylpyrimidinyl, methoxypyrrolidinylpyrimidinyl, methoxymethylpyrrolidinylpyrimidinyl, oxopyrrolidinylpyrimidinyl, (methyl)(oxo)pyrrolidinylpyrimidinyl, dimethylaminopyrrolidinylpyrimidinyl, carboxypyrrolidinylpyrimidinyl, dioxoisothiazolidinylpyrimidinyl, hydroxytetrahydropyranylpyrimidinyl, difluoropip eridinylpyrimidinyl, hydroxypiperidinylpyrimidinyl, hydroxymethylpiperidinylpyrimidinyl, methoxypiperidinylpyrimidinyl, oxopiperidinylpyrimidinyl, (carboxy)-(methyl)piperidinylpyrimidinyl, (carboxy)(hydroxy)piperidinylpyrimidinyl, (amino)-(carboxy)piperidinylpyrimidinyl, (ethoxycarbonyl)(methyl)piperidinylpyrimidinyl, aminocarbonylpiperidinylpyrimidinyl, hydroxyethylpiperazinylpyrimidinyl, (methyl)-(oxopiperazinyl)pyrimidinyl, carboxymethylpiperazinylpyrimidinyl, carboxyethylpiperazinylpyrimidinyl, tetrazolylmethylpiperazinylpyrimidinyl, amino carbonylmethyl-piperazinylpyrimidinyl, methylmorpholinylpyrimidinyl, dimethylmorpholinylpyrimidinyl, oxomorpholinylpyrimidinyl, hydroxymethylazetidinylcarbonylpyridinyl, piperazinylcarbonylpyridinyl, methylpiperazinylcarbonylpyridinyl, morpholinylcarbonylpyridinyl, thiomorpholinylcarbonylpyridinyl, dioxothiomorpholinylcarbonylpyridinyl, (methyl)-(morpholinylmethyl)pyrimidinyl, carboxy-3-azabicyclo[3.1.0]hexanylpyrimidinyl, ethoxycarbonyl-3-azabicyclo[3.1.0]hexanylpyrimidinyl, carboxy-3-azabicyclo[4.1.0]-heptanylpyrimidinyl, carboxy-3-azabicyclo[3.2.1]octanylpyrimidinyl, methoxycarbonyl-3-azabicyclo[3.2.1]octanylpyrimidinyl, oxo-3,6-diazabicyclo[3.2.2]nonanylpyrimidinyl, oxo-2-oxa-6-azaspiro[3.4]octanylpyridinyl, difluoro-5-azaspiro[2.4]heptanylpyrimidinyl, carboxy-2-azaspiro[3.3]heptanylpyrimidinyl and 7-oxa-2-azaspiro[3.5]nonanylpyrimidinyl.

Definitive values of $R^{11}$ include bromo, tert-butoxycarbonyl-1,2,3,6-tetrahydropyridinyl, methylpyrazolyl, cyanopyridinyl, methoxypyridinyl, oxopyridinyl, piperazinylpyridinyl, morpholinylpyridinyl, carboxypiperidinylpyrimidinyl, piperazinylpyrimidinyl, methylsulphonylpiperazinylpyrimidinyl, oxopiperazinylpyrimidinyl, oxodiazepanylpyrimidinyl and 2-oxa-6-azaspiro[3.3]heptanylpyrimidinyl. Additional values include aminosulphonylphenyl, methylsulphonylpiperidinyl, acetylpiperidinyl, tert-butoxycarbonylpiperidinyl, dihydropyranyl, dihydrothiopyranyl, methylsulphonyl-1,2,3,6-tetrahydropyridinyl, acetyl-1,2,3,6-tetrahydropyridinyl, methylsulphonyl-8-azabicyclo[3.2.1]octenyl, tert-butoxycarbonyl-8-azabicyclo[3.2.1]octenyl, oxoindolyl, hydroxyisopropylpyrimidinyl, tetrahydrofuranylaminopyrimidinyl, carboxycyclohexylpyrimidinyl, morpholinylthiazolyl, carboxypiperidinylpyridinyl, (carboxy)(methyl)-piperidinylpyridinyl, (methyl)(oxopiperazinyl)pyridinyl, methoxypyrrolidinylpyrimidinyl, carboxypyrrolidinylpyrimidinyl, difluoropiperidinylpyrimidinyl, (carboxy)(methyl)-piperidinylpyrimidinyl, (carboxy)(hydroxy)piperidinylpyrimidinyl, (ethoxycarbonyl)-(methyl) piperidinylpyrimidinyl, carboxymethylpiperazinylpyrimidinyl, carboxyethylpiperazinylpyrimidinyl, tetrazolylmethylpiperazinylpyrimidinyl, amino carbonylmethyl-piperazinylpyrimidinyl, dimethylmorpholinylpyrimidinyl, carboxy-3-azabicyclo[3.1.0]-hexanylpyrimidinyl, ethoxycarbonyl-3-azabicyclo[3.1.0]hexanylpyrimidinyl, carboxy-3-azabicyclo[4.1.0]heptanylpyrimidinyl, oxo-3,6-diazabicyclo[3.2.2]nonanylpyrimidinyl and carboxy-2-azaspiro[3.3]heptanylpyrimidinyl.

Illustrative values of $R^{11}$ include methoxypyridinyl, oxopyridinyl, piperazinylpyrimidinyl, oxopiperazinylpyrimidinyl and oxodiazepanylpyrimidinyl.

Typically, $R^{15}$ and $R^{16}$ may independently represent hydrogen, fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical values of $R^{15}$ include hydrogen, halogen, $C_{1-6}$ alkyl, trifluoromethyl, $C_{1-6}$ alkoxy, difluoromethoxy and trifluoromethoxy.

Illustrative values of $R^{15}$ include halogen and difluoromethoxy.

In a first embodiment, $R^{15}$ represents hydrogen. In a second embodiment, $R^{15}$ represents halogen. In a first aspect of that embodiment, $R^{15}$ represents fluoro. In a second aspect of that embodiment, $R^{15}$ represents chloro. In a third embodiment, $R^{15}$ represents $C_{1-6}$ alkyl. In one aspect of that embodiment, $R^{15}$ represents methyl. In a fourth embodiment, $R^{15}$ represents trifluoromethyl. In a fifth embodiment, $R^{15}$ represents $C_{1-6}$ alkoxy. In one aspect of that embodiment, $R^{15}$ represents methoxy. In a sixth embodiment, $R^{15}$ represents difluoromethoxy. In a seventh embodiment, $R^{15}$ represents trifluoromethoxy.

Selected values of $R^{15}$ include hydrogen, fluoro, chloro, methyl, trifluoromethyl, methoxy, difluoromethoxy and trifluoromethoxy.

Suitable values of $R^{15}$ include chloro and difluoromethoxy.

Typical values of $R^{15}$ include hydrogen, halogen, $C_{1-6}$ alkyl, trifluoromethyl, difluoromethoxy and amino.

Illustrative values of $R^{16}$ include hydrogen and halogen.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro. In a third embodiment, $R^{16}$ represents $C_{1-6}$ alkyl. In one aspect of that embodiment, $R^{16}$ represents methyl. In a fourth embodiment, $R^{16}$ represents trifluoromethyl. In a fifth embodiment, $R^{16}$ represents difluoromethoxy. In a seventh embodiment, $R^{16}$ represents amino.

Selected values of $R^{16}$ include hydrogen, fluoro, chloro, methyl, trifluoromethyl, difluoromethoxy and amino.

Suitable values of $R^{16}$ include hydrogen and chloro.

In a particular embodiment, $R^{16}$ is attached at the para-position of the phenyl ring relative to the integer $R^{15}$.

A particular sub-group of the compounds of formula (IIA) above is represented by the compounds of formula (IIB) and N-oxides thereof, and pharmaceutically acceptable salts and solvates thereof, and glucuronide derivatives thereof, and co-crystals thereof:

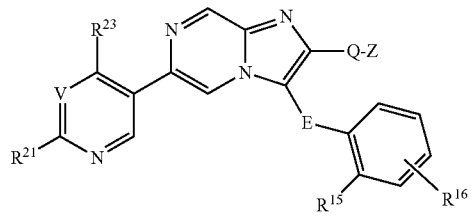

(IIB)

wherein

V represents C—$R^{22}$ or N;

$R^{21}$ represents hydrogen, halogen, halo($C_{1-6}$)alkyl, cyano, $C_{1-6}$ alkyl, trifluoromethyl, $C_{2-6}$ alkenyl, $C_{2-6}$ alkynyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, amino, amino($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{3-7}$)heterocycloalkylamino, $C_{2-6}$ alkylcarbonylamino, ($C_{2-6}$)alkylcarbonylamino($C_{1-6}$)alkyl, $C_{2-6}$ alkoxycarbonylamino, $C_{1-6}$ alkylsulphonylamino, ($C_{1-6}$)alkylsulphonylamino($C_{1-6}$)alkyl, formyl, $C_{2-6}$ alkylcarbonyl, carboxy, $C_{2-6}$ alkoxycarbonyl, aminocarbonyl, $C_{1-6}$ alkylamino carbonyl, di($C_{1-6}$)alkylaminocarbonyl, aminosulphonyl, $C_{1-6}$ alkylaminosulphonyl or di($C_{1-6}$)alkylaminosulphonyl; or $R^{21}$ represents ($C_{3-7}$)cycloalkyl, ($C_{4-7}$)cycloalkenyl, ($C_{3-7}$)heterocycloalkyl, ($C_{3-7}$)heterocycloalkenyl, ($C_{4-9}$)heterobicycloalkyl or ($C_{4-9}$)spiroheterocycloalkyl, any of which groups may be optionally substituted by one or more substituents;

$R^{22}$ represents hydrogen, halogen, cyano or $C_{1-6}$ alkyl;

$R^{23}$ represents hydrogen or $C_{1-6}$ alkyl; and

E, Q, Z, $R^{15}$ and $R^{16}$ are as defined above.

In one embodiment, V represents C—$R^{22}$. In another embodiment, V represents N.

Generally, $R^{21}$ represents hydrogen, halogen, cyano, $C_{1-6}$ alkyl, trifluoromethyl, $C_{2-6}$ alkenyl, $C_{2-6}$ alkynyl, hydroxy, $C_{1-6}$ alkoxy, difluoromethoxy, trifluoromethoxy, trifluoroethoxy, $C_{1-6}$ alkylthio, $C_{1-6}$ alkylsulphonyl, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl; or $R^{21}$ represents ($C_{4-7}$)cycloalkenyl, ($C_{3-7}$)heterocycloalkyl, ($C_{3-7}$)heterocycloalkenyl, ($C_{4-9}$)heterobicycloalkyl or ($C_{4-9}$)spiroheterocycloalkyl, any of which groups may be optionally substituted by one or more substituents.

Ideally, $R^{21}$ represents hydroxy($C_{1-6}$)alkyl, $C_{1-6}$ alkoxy or ($C_{3-7}$)heterocycloalkylamino; or $R^{21}$ represents ($C_{3-7}$)cycloalkyl, ($C_{3-7}$)heterocycloalkyl, ($C_{4-9}$)heterobicycloalkyl or ($C_{4-9}$)spiroheterocycloalkyl, any of which groups may be optionally substituted by one or more substituents.

Typically, $R^{21}$ represents hydrogen, halogen, cyano, $C_{1-6}$ alkyl, trifluoromethyl, $C_{2-6}$ alkenyl, hydroxy, $C_{1-6}$ alkoxy, trifluoroethoxy, amino, di($C_{1-6}$)alkylamino, ($C_{1-6}$)-alkoxy ($C_{1-6}$)alkylamino, N—[($C_{1-6}$)alkyl]-N-[hydroxy($C_{1-6}$)alkyl] amino, $C_{1-6}$ alkylsulphonylamino or carboxy; or $R^{21}$ represents ($C_{3-7}$)heterocycloalkyl, ($C_{4-9}$)heterobicycloalkyl or ($C_{4-9}$)spiroheterocycloalkyl, any of which groups may be optionally substituted by one or more substituents. Additionally, $R^{21}$ may represent hydroxy($C_{1-6}$)alkyl or ($C_{3-7}$)-heterocycloalkylamino; or $R^{21}$ may represent optionally substituted ($C_{3-7}$)cycloalkyl.

Suitably, $R^{21}$ represents hydroxy or $C_{1-6}$ alkoxy; or $R^{21}$ represents ($C_{3-7}$)heterocycloalkyl or ($C_{4-9}$)heterobicycloalkyl, either of which groups may be optionally substituted by one or more substituents. Additionally, $R^{21}$ may represent hydroxy($C_{1-6}$)alkyl or ($C_{3-7}$)heterocycloalkylamino; or $R^{21}$ may represent ($C_{3-7}$)cycloalkyl or ($C_{4-9}$) spiroheterocycloalkyl, either of which groups may be optionally substituted by one or more substituents.

Where $R^{21}$ represents an optionally substituted ($C_{3-7}$) cycloalkyl group, typical values include cyclopropyl, cyclobutyl, cyclopentyl, cyclohexyl and cycloheptyl, any of which groups may be optionally substituted by one or more substituents.

Where $R^{21}$ represents an optionally substituted ($C_{4-7}$) cycloalkenyl group, typical values include cyclobutenyl, cyclopentenyl, cyclohexenyl and cycloheptenyl, any of which groups may be optionally substituted by one or more substituents.

Where $R^{21}$ represents an optionally substituted ($C_{3-7}$) heterocycloalkyl group, typical values include pyrrolidinyl, piperidinyl, piperazinyl, morpholinyl, thiomorpholinyl, diazepanyl and thiadiazepanyl, any of which groups may be optionally substituted by one or more substituents. Additional values include oxetanyl, azetidinyl, tetrahydrofuranyl, isothiazolidinyl, imidazolidinyl and tetrahydropyranyl, any of which groups may be optionally substituted by one or more substituents.

Where $R^{21}$ represents an optionally substituted ($C_{3-7}$) heterocycloalkenyl group, a typical value is optionally substituted 1,2,3,6-tetrahydropyridinyl. Additional values include dihydropyranyl and dihydrothiopyranyl, either of which groups may be optionally substituted by one or more substituents.

Where $R^{21}$ represents an optionally substituted ($C_{4-9}$) heterobicycloalkyl group, typical values include 3-azabicyclo[3.1.0]hexanyl, 2-oxa-5-azabicyclo[2.2.1]heptanyl, quinuclidinyl, 2-oxa-5-azabicyclo[2.2.2]octanyl, 8-azabicyclo [3.2.1]octanyl, 3,8-diazabicyclo[3.2.1]octanyl and 3,9-diazabicyclo[4.2.1]nonanyl, any of which groups may be optionally substituted by one or more substituents. Additional values include 3-azabicyclo[4.1.0]heptanyl, 3-azabicyclo[3.2.1]octanyl and 3,6-diazabicyclo[3.2.2]octanyl, any of which groups may be optionally substituted by one or more substituents.

Where $R^{21}$ represents an optionally substituted ($C_{4-9}$) spiroheterocycloalkyl group, typical values include 2-oxa-6-azaspiro[3.3]heptanyl, 2-oxa-6-azaspiro[3.4]octanyl, 2-oxa-6-azaspiro[3.5]nonanyl and 2-oxa-7-azaspiro[3.5] nonanyl, any of which groups may be optionally substituted by one or more substituents. Additional values include 5-azaspiro-[2.4]heptanyl, 2-azaspiro[3.3]heptanyl and 7-oxa-2-azaspiro[3.5]nonanyl, any of which groups may be optionally substituted by one or more substituents.

Examples of optional substituents which may be present on $R^{21}$ include one, two or three substituents independently selected from halogen, cyano, cyano($C_{1-6}$)alkyl, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkyl-sulphonyl ($C_{1-6}$)alkyl, oxo, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl, aminocarbonyl, $C_{1-6}$ alkylaminocarbonyl, di($C_{1-6}$)alkylaminocarbonyl, $C_{1-6}$ alkylsulphonylaminocarbonyl, aminosulphonyl, $C_{1-6}$ alkylaminosulphonyl and di($C_{1-6}$)alkylaminosulphonyl. Additional examples include tetrazolyl($C_{1-6}$)alkyl and aminocarbonyl($C_{1-6}$)alkyl.

Suitable examples of optional substituents on $R^{21}$ include one, two or three substituents independently selected from fluoro, chloro, bromo, cyano, cyanomethyl, methyl, ethyl, trifluoromethyl, trifluoroethyl, ethenyl, hydroxy, methoxy, ethoxy, difluoro-methoxy, trifluoromethoxy, trifluoroethoxy, methylthio, methylsulphonyl, methyl-sulphonylmethyl, oxo, amino, methylamino, dimethylamino, acetylamino, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, tert-butoxycarbonyl, methoxycarbonylmethyl, ethoxycarbonylmethyl, tetrazolyl, aminocarbonyl, methylaminocarbonyl, dimethylaminocarbonyl, methylsulphonylaminocarbonyl, aminosulphonyl, methylaminosulphonyl and dimethylaminosulphonyl. Additional examples include tetrazolylmethyl and aminocarbonylmethyl.

Definitive examples of optional substituents which may be present on $R^{21}$ include one, two or three substituents independently selected from halogen, $C_{1-6}$ alkyl, hydroxy, $C_{1-6}$ alkoxy, $C_{1-6}$ alkylsulphonyl, oxo, carboxy, carboxy($C_{1-6}$)alkyl and $C_{2-6}$ alkoxycarbonyl. Additional examples include tetrazolyl($C_{1-6}$)alkyl and aminocarbonyl($C_{1-6}$)alkyl.

Selected examples of optional substituents on $R^{21}$ include one, two or three substituents independently selected from cyano($C_{1-6}$)alkyl, trifluoroethyl, hydroxy, $C_{1-6}$ alkylsulphonyl, ($C_{1-6}$)alkylsulphonyl($C_{1-6}$)alkyl, oxo, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl and $C_{1-6}$ alkylsulphonylamino carbonyl.

Selected examples of particular substituents on $R^{21}$ include one, two or three substituents independently selected from fluoro, methyl, hydroxy, methoxy, methylsulphonyl, oxo, carboxy, carboxymethyl, carboxyethyl and ethoxycarbonyl. Additional examples include tetrazolylmethyl and aminocarbonylmethyl.

Examples of particular substituents on $R^{21}$ include one, two or three substituents independently selected from cyanoethyl, trifluoroethyl, hydroxy, methylsulphonyl, methylsulphonylethyl, oxo, acetyl, carboxy, carboxymethyl, carboxyethyl, tert-butoxycarbonyl, ethoxycarbonylmethyl, ethoxycarbonylethyl, tetrazolyl and methylsulphonylaminocarbonyl.

Suitably, $R^{21}$ may be substituted by oxo.

Typically, $R^{21}$ represents hydrogen, fluoro, cyano, methyl, trifluoromethyl, ethenyl, hydroxy, methoxy, isopropoxy, trifluoroethoxy, amino, dimethylamino, methoxyethylamino, N-(hydroxyethyl)-N-(methyl)amino, carboxy, pyrrolidinyl, hydroxypyrrolidinyl, piperidinyl, acetylpiperidinyl, carboxypiperidinyl, piperazinyl, cyanoethylpiperazinyl, trifluoroethylpiperazinyl, methylsulphonylpiperazinyl, methylsulphonylethylpiperazinyl, oxopiperazinyl, acetylpiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, morpholinyl, thiomorpholinyl, oxothiomorpholinyl, dioxothiomorpholinyl, oxodiazepanyl, dioxothiadiazepanyl, 2-oxa-5-azabicyclo[2.2.1]heptanyl, 2-oxa-6-azaspiro[3.3]heptanyl, 2-oxa-6-azaspiro[3.4]octanyl, 2-oxa-6-azaspiro[3.5]-nonanyl or 2-oxa-7-azaspiro[3.5]nonanyl. Additionally, $R^{21}$ may represent hydroxyisopropyl, tetrahydrofuranylamino, carboxycyclohexyl, methoxypyrrolidinyl, carboxypyrrolidinyl, difluoropiperidinyl, (carboxy)(methyl)piperidinyl, (carboxy)(hydroxy)-piperidinyl, (ethoxycarbonyl)(methyl)piperidinyl, tetrazolylmethylpiperazinyl, aminocarbonylmethylpiperazinyl, dimethylmorpholinyl, carboxy-3-azabicyclo[3.1.0]hexanyl, ethoxycarbonyl-3-azabicyclo[3.1.0]hexanyl, carboxy-3-azabicyclo[4.1.0]heptanyl, oxo-3,6-diazabicyclo[3.2.2]nonanyl or carboxy-2-azaspiro[3.3]heptanyl.

Selected values of $R^{21}$ include cyano, methoxy, carboxypiperidinyl, piperazinyl, methylsulphonylpiperazinyl, oxopiperazinyl, carboxymethylpiperazinyl, carboxyethylpiperazinyl, morpholinyl, oxodiazepanyl and 2-oxa-6-azaspiro[3.3]heptanyl. Additional values include hydroxyisopropyl, tetrahydrofuranylamino, carboxycyclohexyl, methoxypyrrolidinyl, carboxypyrrolidinyl, difluoropiperidinyl, (carboxy)(methyl)piperidinyl, (carboxy)(hydroxy)piperidinyl, (ethoxycarbonyl)(methyl)piperidinyl, tetrazolylmethylpiperazinyl, aminocarbonylmethylpiperazinyl, dimethylmorpholinyl, carboxy-3-azabicyclo[3.1.0]hexanyl, ethoxycarbonyl-3-azabicyclo[3.1.0]hexanyl, carboxy-3-azabicyclo[4.1.0]heptanyl, oxo-3,6-diazabicyclo[3.2.2]nonanyl and carboxy-2-azaspiro[3.3]heptanyl.

Illustrative values of $R^{21}$ include hydroxy, methoxy, piperazinyl, oxopiperazinyl and oxodiazepanyl.

In a particular embodiment, $R^{21}$ represents hydroxy($C_{1-6}$)alkyl. In one aspect of that embodiment, $R^{21}$ represents hydroxyisopropyl, especially 2-hydroxyprop-2-yl.

Generally, $R^{22}$ represents hydrogen or $C_{1-6}$ alkyl.

Suitably, $R^{22}$ represents hydrogen, chloro, cyano or methyl.

Appositely, $R^{22}$ represents hydrogen or cyano.

Typically, $R^{22}$ represents hydrogen or methyl.

In one embodiment, $R^{22}$ represents hydrogen. In another embodiment, $R^{22}$ represents $C_{1-6}$ alkyl, especially methyl. In a further embodiment, $R^{22}$ represents cyano. In an additional embodiment, $R^{22}$ represents halogen, especially chloro.

Typically, $R^{23}$ represents hydrogen or methyl.

In one embodiment, $R^{23}$ represents hydrogen. In another embodiment, $R^{23}$ represents $C_{1-6}$ alkyl, especially methyl.

Particular sub-groups of the compounds of formula (IIB) above are represented by the compounds of formula (IIC), (IID) and (IIE) and N-oxides thereof, and pharmaceutically acceptable salts and solvates thereof, and glucuronide derivatives thereof, and co-crystals thereof:

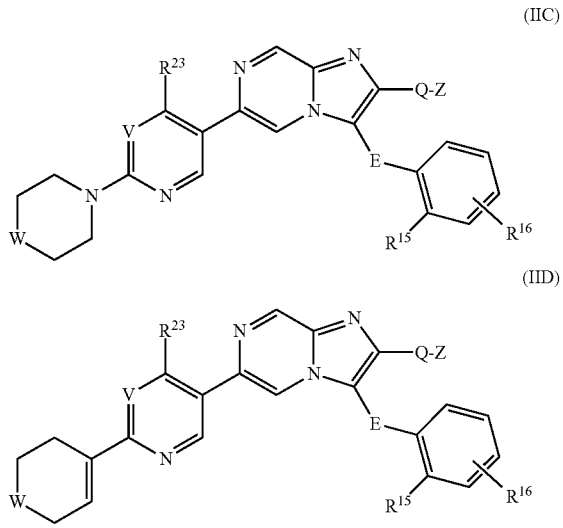

(IIE)

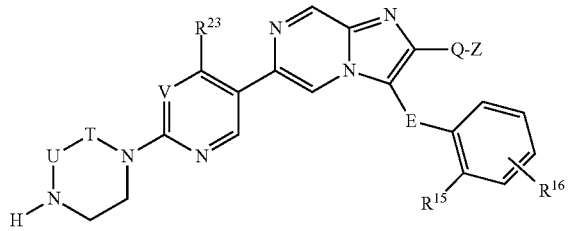

wherein
T represents —$CH_2$— or —$CH_2CH_2$—;
U represents C(O) or S(O)$_2$;
W represents O, S, S(O), S(O)$_2$, N($R^{31}$) or C($R^{32}$)($R^{33}$);
$R^{31}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$) alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl($C_{1-6}$)alkyl, aminocarbonyl, aminocarbonyl($C_{1-6}$)alkyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl;
$R^{32}$ represents halogen, $C_{1-6}$ alkoxy, carboxy, carboxy ($C_{1-6}$)alkyl, $C_{2-6}$ alkoxycarbonyl, $C_{2-6}$ alkoxycarbonyl($C_{1-6}$) alkyl, tetrazolyl or aminocarbonyl;
$R^{33}$ represents hydrogen, halogen, $C_{1-6}$ alkyl, hydroxy or amino; and
V, E, Q, Z, $R^{15}$, $R^{16}$ and $R^{23}$ are as defined above.

In a first embodiment, T represents —$CH_2$—. In a second embodiment, T represents —$CH_2CH_2$—.

In a first embodiment, U represents C(O). In a second embodiment, U represents S(O)$_2$.

Generally, W represents O, S, S(O), S(O)$_2$, N($R^{31}$), CF$_2$, CH(CO$_2$H) or CH(tetrazolyl).

Appositely, W represents O, N($R^{31}$) or C($R^{32}$)($R^{33}$).

Suitably, W represents O, S, S(O), S(O)$_2$, N($R^{31}$) or CH(CO$_2$H).

Typically, W represents O, S(O)$_2$, N($R^{31}$) or CH(CO$_2$H).

In a first embodiment, W represents O. In a second embodiment, W represents S. In a third embodiment, W represents S(O). In a fourth embodiment, W represents S(O)$_2$. In a fifth embodiment, W represents N($R^{31}$). In a sixth embodiment, W represents C($R^{32}$)($R^{33}$). In a first aspect of the sixth embodiment, W represents CF$_2$. In a second aspect of the sixth embodiment, W represents CH(CO$_2$H). In third aspect of the sixth embodiment, W represents CH(tetrazolyl).

Generally, $R^{31}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)-alkyl, aminocarbonyl, $C_{1-6}$ alkylaminocarbonyl, di($C_{1-6}$)alkylamino carbonyl, aminosulphonyl, $C_{1-6}$ alkylaminosulphonyl or di($C_{1-6}$)alkylaminosulphonyl.

Suitably, $R^{31}$ represents hydrogen, cyano($C_{1-6}$)alkyl, trifluoroethyl, $C_{1-6}$ alkylsulphonyl, ($C_{1-6}$)alkylsulphonyl($C_{1-6}$) alkyl, $C_{2-6}$ alkylcarbonyl, carboxy($C_{1-6}$)alkyl, $C_{2-6}$ alkoxycarbonyl or $C_{2-6}$ alkoxycarbonyl($C_{1-6}$)alkyl. Additionally, $R^{31}$ may represent tetrazolyl($C_{1-6}$)alkyl or aminocarbonyl ($C_{1-6}$)alkyl.

Definitively, $R^{31}$ represents hydrogen, $C_{1-6}$ alkylsulphonyl or carboxy($C_{1-6}$)alkyl. Additionally, $R^{31}$ may represent tetrazolyl($C_{1-6}$)alkyl or aminocarbonyl($C_{1-6}$)alkyl.

Typical values of $R^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, aminocarbonyl, methylaminocarbonyl, dimethylaminocarbonyl, aminosulphonyl, methylaminosulphonyl and dimethylaminosulphonyl. Additional values include tetrazolylmethyl and aminocarbonylmethyl.

Selected values of $R^{31}$ include hydrogen, cyanoethyl, trifluoroethyl, methylsulphonyl, methylsulphonylethyl, acetyl, carboxymethyl, carboxyethyl, tert-butoxycarbonyl, ethoxycarbonylmethyl and ethoxycarbonylethyl. Additional values include tetrazolylmethyl and aminocarbonylmethyl.

Definitive values of $R^{31}$ include hydrogen, methylsulphonyl, carboxymethyl and carboxyethyl. Additional values include tetrazolylmethyl and aminocarbonylmethyl.

A particular value of $R^{31}$ is hydrogen.

Suitably, $R^{32}$ represents halogen, $C_{1-6}$ alkoxy, carboxy, carboxy($C_{1-6}$)alkyl, $C_{2-6}$ alkoxycarbonyl, $C_{2-6}$ alkoxycarbonyl($C_{1-6}$)alkyl or tetrazolyl.

Typically, $R^{32}$ represents halogen, carboxy or $C_{2-6}$ alkoxycarbonyl.

Typical values of $R^{32}$ include fluoro, methoxy, carboxy, carboxymethyl, carboxyethyl, methoxycarbonyl, ethoxycarbonyl, methoxycarbonylmethyl, methoxycarbonylethyl, ethoxycarbonylmethyl, ethoxycarbonylethyl, tetrazolyl and aminocarbonyl.

Particular values of $R^{32}$ include fluoro, carboxy and ethoxycarbonyl.

In a selected embodiment, $R^{32}$ represents carboxy.

Suitably, $R^{33}$ represents hydrogen, halogen, $C_{1-6}$ alkyl or hydroxy.

In a first embodiment, $R^{33}$ represents hydrogen. In a second embodiment, $R^{33}$ represents halogen. In one aspect of that embodiment, $R^{33}$ represents fluoro. In a third embodiment, $R^{33}$ represents $C_{1-6}$ alkyl. In one aspect of that embodiment, $R^{33}$ represents methyl. In a fourth embodiment, $R^{33}$ represents hydroxy. In a fifth embodiment, $R^{33}$ represents amino.

Another sub-group of the compounds of formula (IIB) above is represented by the compounds of formula (IIF) and N-oxides thereof, and pharmaceutically acceptable salts and solvates thereof, and glucuronide derivatives thereof, and co-crystals thereof:

(IIF)

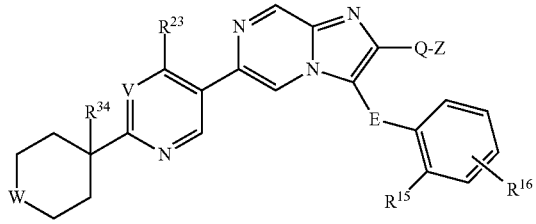

wherein
$R^{34}$ represents hydrogen, halogen, halo($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, amino, $C_{1-6}$ alkylamino, di($C_{1-6}$)alkylamino, ($C_{2-6}$)alkylcarbonylamino, ($C_{2-6}$)alkylcarbonylamino($C_{1-6}$)alkyl, ($C_{1-6}$)alkylsulphonylamino, or ($C_{1-6}$) alkylsulphonylamino($C_{1-6}$)alkyl; and
E, Q, Z, V, W, $R^{15}$, $R^{16}$ and $R^{23}$ are as defined above.

In a first embodiment, $R^{34}$ represents hydrogen. In a second embodiment, $R^{34}$ represents halogen. In one aspect of that embodiment, $R^{34}$ represents fluoro. In a third embodiment, $R^{34}$ represents halo($C_{1-6}$)alkyl. In one aspect of that embodiment, $R^{34}$ represents fluoromethyl. In a fourth embodiment, $R^{34}$ represents hydroxy. In a fifth embodiment, $R^{34}$ represents $C_{1-6}$ alkoxy, especially methoxy. In a sixth embodiment, $R^{34}$ represents $C_{1-6}$ alkylthio, especially methylthio. In a seventh embodiment, $R^{34}$ represents $C_{1-6}$ alkylsulphinyl, especially methylsulphinyl. In an eighth embodiment, $R^{34}$ represents $C_{1-6}$ alkylsulphonyl, especially methylsulphonyl. In a ninth embodiment, $R^{34}$ represents amino. In a tenth embodiment, $R^{34}$ represents $C_{1-6}$ alkylamino, especially methylamino. In an eleventh embodiment, $R^{34}$ represents di($C_{1-6}$)alkylamino, especially dimethylamino. In a twelfth embodiment, $R^{34}$ represents ($C_{2-6}$)alkylcarbonylamino, especially acetylamino. In a thirteenth embodiment, $R^{34}$ represents ($C_{2-6}$)alkylcarbonylamino($C_{1-6}$)alkyl, especially acetylaminomethyl. In a fourteenth embodiment, $R^{34}$ represents ($C_{1-6}$)alkylsulphonylamino, especially methylsulphonylamino. In a fifteenth embodiment, $R^{34}$ represents ($C_{1-6}$)alkylsulphonylamino($C_{1-6}$)alkyl, especially methylsulphonylaminomethyl.

Typically, $R^{34}$ represents hydrogen, halogen, halo($C_{1-6}$)alkyl, hydroxy or ($C_{2-6}$)alkylcarbonylamino($C_{1-6}$)alkyl.

Selected values of $R^{34}$ include hydrogen, fluoro, fluoromethyl, hydroxy, methoxy, methylthio, methylsulphinyl, methylsulphonyl, amino, methylamino, dimethylamino and acetylaminomethyl.

Particular values of $R^{34}$ include hydrogen, fluoro, fluoromethyl, hydroxy and acetylaminomethyl.

Suitably, $R^{34}$ represents hydrogen or hydroxy.

A further sub-group of the compounds of formula (IIB) above is represented by the compounds of formula (IIG) and N-oxides thereof, and pharmaceutically acceptable salts and solvates thereof, and glucuronide derivatives thereof, and co-crystals thereof:

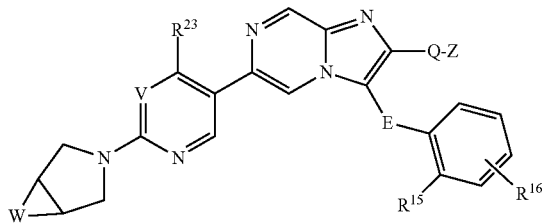

(IIG)

wherein

E, Q, Z, V, W, $R^{15}$, $R^{16}$ and $R^{23}$ are as defined above.

Specific novel compounds in accordance with the present invention include each of the compounds whose preparation is described in the accompanying Examples, and pharmaceutically acceptable salts and solvates thereof The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

The compounds of formula (I) above may be prepared by a process which comprises reacting a compound of formula (III) with a compound of formula (IV):

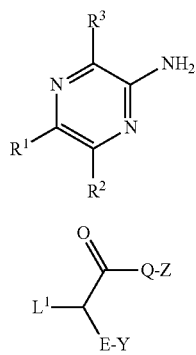

(III)

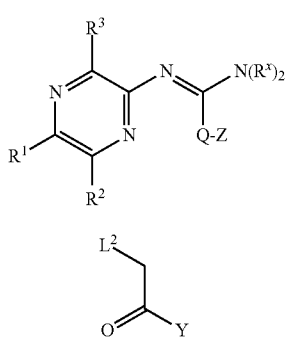

(IV)

wherein E, Q, Y, Z, $R^1$, $R^2$ and $R^3$ are as defined above, and $L^1$ represents a suitable leaving group.

The leaving group $L^1$ is typically a halogen atom, e.g. bromo.

The reaction is conveniently effected at an elevated temperature in a suitable solvent, e.g. a $C_{1-4}$ alkanol such as ethanol, or a cyclic ether such as 1,4-dioxane.

The compounds of formula (I) above wherein E represents —C(O)— may be prepared by a process which comprises reacting a compound of formula (V) with a compound of formula (VI):

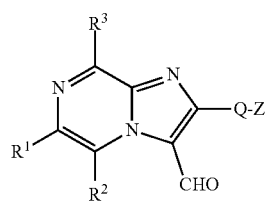

(V)

(VI)

wherein Q, Y, Z, $R^1$, $R^2$ and $R^3$ are as defined above, $R^x$ represents a $C_{1-4}$ alkyl group, e.g. methyl, and $L^2$ represents a suitable leaving group.

The leaving group $L^2$ is typically a halogen atom, e.g. bromo.

The reaction is conveniently effected at ambient or elevated temperature in a suitable solvent, e.g. a dipolar aprotic solvent such as N,N-dimethylformamide, a hydrocarbon solvent such as toluene, or a $C_{1-4}$ alkanol such as ethanol.

The intermediates of formula (V) above may be prepared by reacting a compound of formula (III) as defined above with a compound of formula (VII):

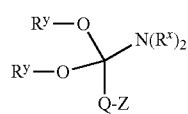

(VII)

wherein Q, Z and $R^x$ are as defined above, and $R^y$ represents a $C_{1-4}$ alkyl group, e.g. methyl.

The reaction is conveniently effected at an elevated temperature in a suitable solvent, e.g. a hydrocarbon solvent such as toluene, or a $C_{1-4}$ alkanol such as methanol.

The compounds of formula (I) above wherein E represents —CH(OH)— may be prepared by a process which comprises reacting a compound of formula Y-MgHal with a compound of formula (VIII):

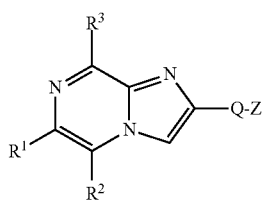

(VIII)

wherein Q, Y, Z, $R^1$, $R^2$ and $R^3$ are as defined above, and Hal represents a halogen atom.

The halogen atom Hal is typically bromo.

The reaction is conveniently effected at ambient temperature in a suitable solvent, e.g. a cyclic ether such as tetrahydrofuran.

The intermediates of formula (VIII) above may be prepared by treating a compound of formula (IX):

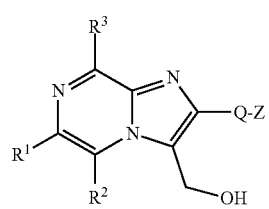

(IX)

wherein Q, Z, $R^1$, $R^2$ and $R^3$ are as defined above; with (chloromethylene)dimethyl-iminium chloride (Vilsmeier reagent).

The reaction is conveniently effected at an elevated temperature in a suitable solvent, e.g. a dipolar aprotic solvent such as N,N-dimethylformamide.

The compounds of formula (I) above wherein E represents —$CH_2$— and Y represents optionally substituted aryl or heteroaryl may be prepared by a process which comprises reacting a compound of formula $Y^1$—H with a compound of formula (X):

(X)

wherein Q, Z, $R^1$, $R^2$ and $R^3$ are as defined above, and $Y^1$ represents aryl or heteroaryl, either of which groups may be optionally substituted by one or more substituents; in the presence of a sulfonic acid derivative.

The sulfonic acid derivative of use in the foregoing reaction is suitably an organic sulfonic acid derivative such as methanesulfonic acid. The reaction is conveniently effected at an elevated temperature in a suitable solvent, e.g. water.

The intermediates of formula (X) above may be prepared by treating a compound of formula (IX) as defined above with formaldehyde. The reaction is conveniently effected at an elevated temperature in a suitable solvent, e.g. water.

The intermediates of formula (IX) above may be prepared by reacting a compound of formula (III) as defined above with a compound of formula (XI):

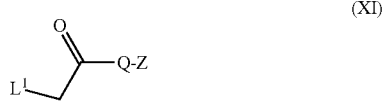

(XI)

wherein Q, Z and $L^1$ are as defined above; under conditions analogous to those described above for the reaction between compounds (III) and (IV).

The compounds of formula (I) above wherein-Q-Z represents —$CH_2OH$ may be prepared by a process which comprises treating a compound of formula (XII):

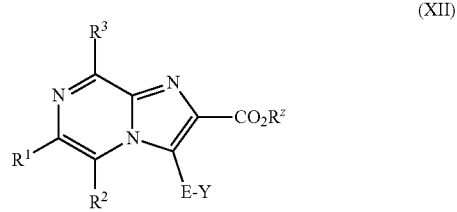

(XII)

wherein E, Y, $R^1$, $R^2$ and $R^3$ are as defined above, and $R^z$ represents a $C_{1-4}$ alkyl group, e.g. methyl; with a reducing agent.

The reducing agent of use in the foregoing reaction is suitably an alkali metal borohydride such as lithium borohydride. The reaction is conveniently effected at ambient temperature in a suitable solvent, e.g. a cyclic ether such as tetrahydrofuran, or a $C_{1-4}$ alkanol such as methanol, or a mixture thereof.

Alternatively, the reducing agent of use in the foregoing reaction may suitably be diisobutylaluminium hydride. The reaction is conveniently effected at a temperature in the region of 0° C. in a suitable solvent, e.g. a cyclic ether such as tetrahydrofuran.

The intermediates of formula (XII) above may be prepared by reacting a compound of formula (III) as defined above with a compound of formula (XIII):

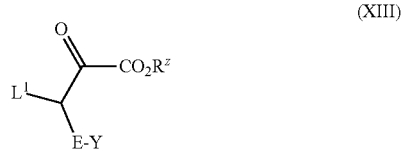

(XIII)

wherein E, Y, $R^z$ and $L^1$ are as defined above; under conditions analogous to those described above for the reaction between compounds (III) and (IV).

The compounds of formula (I) above wherein E represents —N(H)— may be prepared by a process which comprises reacting a compound of formula (III) as defined above with an isocyanide derivative of formula Y—NC and an aldehyde derivative of formula OHC-Q-Z; in the presence of a transition metal catalyst.

The transition metal catalyst of use in the foregoing reaction is suitably a zirconium derivative, e.g. a zirconium halide such as zirconium (IV) chloride. The reaction is conveniently effected at an elevated temperature in a suitable solvent, e.g. a $C_{1-4}$ alkanol such as n-butanol.

Where they are not commercially available, the starting materials of formula (III), (IV), (VI), (VII), (XI) and (XIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein E represents —C(O)— may be converted into the corresponding compound wherein E represents —CH(OH)— by treatment with a reducing agent such as sodium borohydride.

A compound of formula (I) wherein E represents —CH(OH)— may be converted into the corresponding compound wherein E represents —$CH_2$— by heating with elemental iodine and phosphinic acid in acetic acid; or by treating with triethylsilane and an acid, e.g. an organic acid such as trifluoroacetic acid, or a Lewis acid such as boron trifluoride diethyl etherate; or by a two-step procedure which comprises: (i) treatment with thionyl bromide; and (ii) treatment of the product thereby obtained with a transition metal catalyst, e.g. (2,2'-bipyridine)dichlororuthenium(II) hydrate, in the presence of diethyl 1,4-dihydro-2,6-dimethyl-3,5-pyridinedicarboxylate (Hantzsch ester) and a base, e.g. an organic base such as N,N-diisopropylethylamine.

A compound of formula (I) which contains a hydroxy group may be alkylated by treatment with the appropriate alkyl halide in the presence of a base, e.g. sodium hydride, or silver oxide. A compound of formula (I) wherein-Q-Z represents —$CH_2OH$ may be arylated in a two-step procedure which comprises: (i) treatment with thionyl chloride; and (ii) treatment of the chloro derivative thereby obtained with the appropriate aryl or heteroaryl hydroxide. A compound of formula (I) wherein-Q-Z represents —$CH_2OH$ may be converted into the corresponding compound of formula (I) wherein-Q-Z represents —$CH_2$—S—Z via a two-step procedure which comprises: (i) treatment with thionyl chloride; and (ii) treatment of the chloro derivative thereby obtained with a compound of formula Z—SH, typically in the presence of a base, e.g. an inorganic base such as potassium carbonate. A compound of formula (I) which contains hydroxy may be converted into the corresponding fluoro-substituted compound by treatment with diethylaminosulfur trifluoride (DAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) which contains an N—H moiety may be alkylated by treatment with the appropriate alkyl halide, typically at an elevated temperature in an organic solvent such as acetonitrile. Alternatively, the reaction may be effected at ambient temperature in an organic solvent such as N,N-dimethylformamide, in the presence of a base, e.g. an inorganic base such as cesium carbonate or potassium carbonate. Alternatively, a compound of formula (I) which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound of formula (I) which contains an N—H moiety may be converted into the corresponding compound wherein the nitrogen atom is substituted by $C_{2-6}$ alkylcarbonyl, e.g. acetyl, by treatment with the appropriate acyl anhydride, e.g. acetic anhydride, typically at ambient temperature in the presence of a base, e.g. an organic base such as triethylamine.

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl halide, e.g. a $C_{1-6}$ alkylsulphonyl chloride such as methanesulphonyl chloride, or with the appropriate $C_{1-6}$ alkylsulphonic anhydride, e.g. methanesulphonic anhydride, typically at ambient temperature in the presence of a base, e.g. an organic base such as triethylamine.

A compound of formula (I) containing the moiety —S— may be converted into the corresponding compound containing the moiety —S(O)— by treatment with 3-chloroperoxybenzoic acid. Likewise, a compound of formula (I) containing the moiety —S(O)— may be converted into the corresponding compound containing the moiety —S(O)$_2$— by treatment with 3-chloroperoxybenzoic acid.

A compound of formula (I) containing an aromatic nitrogen atom may be converted into the corresponding N-oxide derivative by treatment with 3-chloroperoxybenzoic acid.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(O), or bis[3-(diphenylphosphanyl)cyclopenta-2,4-dien-1-yl]iron-dichloropalladium-dichloromethane complex, and a base, e.g. an inorganic base such as sodium carbonate or potassium carbonate, or potassium phosphate.

A compound of formula (I) wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato)diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis-(diphenylphosphino)ferrocene]dichloropalladium (II), or bis[3-(diphenylphosphanyl)-cyclopenta-2,4-dien-1-yl]iron-dichloropalladium-dichloromethane complex. Step (ii) is conveniently effected in the presence of a transition metal catalyst such as tetrakis-(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(O), and a reagent such as tri(ortho-tolyl)phosphine.

A compound of formula (I) wherein $R^1$ represents 6-methoxypyridin-3-yl may be converted into the corresponding compound wherein $R^1$ represents 2-oxo-1,2-dihydropyridin-5-yl by treatment with pyridine hydrochloride; or by heating with a mineral acid such as hydrochloric acid. By utilising similar methodology, a compound of formula (I) wherein $R^1$ represents 6-methoxy-4-methylpyridin-3-yl may be converted into the corresponding compound wherein $R^1$ represents 4-methyl-2-oxo-1,2-dihydropyridin-5-yl; and a compound of formula (I) wherein $R^1$ represents 6-methoxy-5-methylpyridin-3-yl may be converted into the corresponding compound wherein $R^1$ represents 3-methyl-2-oxo-1,2-dihydropyridin-5-yl.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

More generally, a compound of formula (I) containing a carbon-carbon double bond may be converted into the corresponding compound containing a carbon-carbon single bond by catalytic hydrogenation, typically by treatment with gaseous hydrogen in the presence of a hydrogenation catalyst such as palladium on charcoal.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid. Alternatively, the transformation may be effected by treatment with a base, typically an inorganic base such as an alkali metal hydroxide, e.g. sodium hydroxide or lithium hydroxide; or an organic base such as sodium methoxide or sodium ethoxide.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound of formula (I) wherein $R^1$ represents a substituent containing at least one nitrogen atom, which substituent is linked to the remainder of the molecule via a nitrogen atom, may be prepared by reacting a compound of formula (I) wherein $R^1$ represents halogen, e.g. bromo, with the appropriate compound of formula $R^1$—H [e.g. 1-(pyridin-3-yl)piperazine]. The reaction is conveniently effected with the assistance of a transition metal catalyst, e.g. tris(dibenzylideneacetone)dipalladium(O), in the presence of an amination ligand such as 2-dicyclohexylphosphino-2',4', 6'-triisopropylbiphenyl (XPhos) and a base, e.g. an inorganic base such as sodium tert-butoxide.

A compound of formula (IIB) wherein $R^{21}$ represents ethenyl may be prepared by reacting a compound of formula (IIB) wherein $R^{21}$ represents halogen, e.g. chloro, with potassium vinyl trifluoroborate. The reaction is typically effected in the presence of a transition metal catalyst, e.g. [1,1'-bis(diphenylphosphino)ferrocene]dichloropalladium (II), and a base, e.g. an organic base such as triethylamine.

A compound of formula (IIB) wherein $R^{21}$ represents a substituent containing at least one nitrogen atom, which substituent is linked to the remainder of the molecule via a nitrogen atom, may be prepared by reacting a compound of formula (IIB) wherein $R^{21}$ represents halogen, e.g. chloro, with the appropriate compound of formula $R^{21}$—H [e.g. 2-methoxyethylamine, pyrrolidin-3-ol, piperazine, 1-(methylsulfonyl)piperazine, piperazin-2-one, morpholine, thiomorpholine, thiomorpholine 1,1-dioxide, 1,4-diazepan-5-one, 2-oxa-5-azabicyclo[2.2.1]heptane or an appropriately substituted azaspiroalkane], optionally in the presence of a base, e.g. an organic base such as triethylamine or 1-methyl-2-pyrrolidinone.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The following Examples illustrate the preparation of compounds according to the invention.

The compounds in accordance with this invention potently inhibit TNFα-induced NF-κB activation in the following assay.

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable transfectant expressing SEAP (secreted alkaline phosphatase) under the control of the IFNβ minimal promoter fused to five NF-κB binding sites. Secretion of SEAP by these cells is stimulated in a dose-dependent manner by TNFα (0.5 ng/mL). Compounds were diluted from 10 mM DMSO stocks (final assay concentration 0.3%) to generate a 10-point 3-fold serial dilution curve (30,000 nM to 2 nM final concentration). They were mixed with cells and stimulating ligand in a 384-well microtitre plate and incubated for 18 h. SEAP activity was determined in the supernatant using the colorimetric substrate QUANTI-Blue™ (InvivoGen). Percentage inhibitions for compound dilutions were calculated between a DMSO control and maximum inhibition (by excess control compound) and an $IC_{50}$ calculated using XLfit™ (4 parameter logistic model) in ActivityBase.

When tested in the above assay, the compounds of the accompanying Examples were all found to exhibit $IC_{50}$ values of 50 μM or better.

EXAMPLES

Abbreviations

DCM: dichloromethane
EtOAc: ethyl acetate
DMF: N,N-dimethylformamide
MeOH: methanol
DMSO: dimethylsulfoxide
TFA: trifluoroacetic acid
THF: tetrahydrofuran
DIPEA: N,N-diisopropylethylamine
MeCN: acetonitrile
EtOH: ethanol
$SiO_2$: silica
h: hour
r.t.: room temperature
RT: retention time
br: broad
M: mass
FCC: flash column chromatography
HPLC: High Performance Liquid Chromatography
LCMS: Liquid Chromatography Mass Spectrometry
ES+: Electrospray Positive Ionisation
Pd(PPh$_3$)$_4$: tetrakis(triphenylphosphine)palladium(O)
Pd(dppf)Cl$_2$: [1,1'-bis(diphenylphosphino)ferrocene]dichloropalladium(II)

Hantzsch ester: diethyl 1,4-dihydro-2,6-dimethyl-3,5-pyridinedicarboxylate

Nomenclature

Compounds were named with the aid of ACD/Name Batch (Network) version 11.01, and/or Accelrys Draw 4.0.

Analytical Conditions

All NMR spectra were obtained either at 250 MHz or at 500 MHz.
Analytical HPLC
Method A
Column: Waters Atlantis dC18 (2.1×100 mm, 3 µm column)
Flow rate: 0.6 mL/minute
Solvent A: 0.1% formic acid/water
Solvent B: 0.1% formic acid/acetonitrile
Injection volume: 3 µL
Column temperature: 40° C.
UV detection wavelength: 215 nm
Eluent: 0.00-5.00 minutes, constant gradient from 95% solvent A+5% solvent B to 100% solvent B; 5.00-5.40 minutes, 100% solvent B; 5.40-5.42 minutes, constant gradient from 100% solvent B to 95% solvent A+5% solvent B; 5.42-7.00 minutes, 95% solvent A+5% solvent B.
Method B
Column: Waters Atlantis dC18 (2.1×50 mm, 3 µm column)
Flow rate: 1.0 mL/minute
Solvent A: 0.1% formic acid/water
Solvent B: 0.1% formic acid/acetonitrile
Injection volume: 3 µL
UV detection wavelength: 215 nm
Eluent: 0.00-2.50 minutes, constant gradient from 95% solvent A+5% solvent B to 100% solvent B; 2.50-2.70 minutes, 100% solvent B; 2.71-3.00 minutes, 95% solvent A+5% solvent B.
Method C
Column: Waters Atlantis dC18 (2.1×30 mm, 3 µm column)
Flow rate: 1.0 mL/minute
Solvent A: 0.1% formic acid/water
Solvent B: 0.1% formic acid/acetonitrile
Injection volume: 3 µL
UV detection wavelength: 215 nm
Eluent: 0.00-1.50 minutes, constant gradient from 95% solvent A+5% solvent B to 100% solvent B; 1.50-1.60 minutes, 100% solvent B; 1.60-1.61 minutes, constant gradient from 100% solvent B to 95% solvent A+5% solvent B; 1.61-2.00 minutes, 95% solvent A+5% solvent B.
MS detection using Waters LCT or LCT Premier, or ZQ or ZMD.
UV detection using Waters 2996 photodiode array or Waters 2787 UV or Waters 2788 UV.
Method D (uPLC)
Column: Phenomenex, Kinetex-XB C18 (2.1 mm×100 mm, 1.7 µm column)
Flow rate: 0.6 mL/minute
Solvent A: 0.1% formic acid/water
Solvent B: 0.1% formic acid/acetonitrile
Injection volume: 3 µL
Column temperature: 40° C.
UV detection wavelength: 215 nm
Eluent: 0.00-5.30 minutes, constant gradient from 95% solvent A+5% solvent B to 100% solvent B; 5.30-5.80 minutes, 100% solvent B; 5.80-5.82 minutes, constant gradient from 100% solvent B to 95% solvent A+5% solvent B.
MS detection using Waters LCT or LCT Premier, or ZQ or ZMD.
UV detection using Waters 2996 photodiode array or Waters 2787 UV or Waters 2788 UV.
Method E (high pH)
Column: Phenomenex, Gemini C18 (2.0 mm×100 mm, 3 µm column)
Flow rate: 0.5 mL/minute
Solvent A: 2 nM ammonium hydrogencarbonate in water
Solvent B: acetonitrile
Injection volume: 3 µL
Column temperature: 50° C.
UV detection wavelength: 215 nm
Eluent: 0.00-5.50 minutes, constant gradient from 95% solvent A+5% solvent B to 100% solvent B; 5.50-5.90 minutes, 100% solvent B.
MS detection using Waters LCT or LCT Premier, or ZQ or ZMD.
UV detection using Waters 2996 photodiode array or Waters 2787 UV or Waters 2788 UV.

Preparative HPLC
Preparative Method A

| Flow rate: | 40 mL/minute | | |
|---|---|---|---|
| Mobile Phase A: | water with 0.1% formic acid | | |
| Mobile Phase B: | acetonitrile with 0.1% formic acid | | |
| Column: | Waters Sunfire, C18, 30 mm × 100 mm | | |
| Particle Size: | 10 µm | | |
| Runtime: | 25.5 minutes | | |
| Inlet method: | LC7_40ml_7030_tubes.w60 | | |
| | Time (min) | % A | % B |
| Method Gradient: | 0.00 | 75 | 25 |
| | 2.00 | 75 | 25 |
| | 2.50 | 70 | 30 |
| | 18.50 | 0 | 100 |
| | 21.50 | 0 | 100 |
| | 22.50 | 99 | 1 |
| | 23.00 | 99 | 1 |
| ACD Flow: | 2 mL/minute (acetonitrile with 0.1% formic acid) throughout run. | | |
| Primary wavelength (collection): | 215 nm | | |
| Equipment: | Gilson 215 Liquid Handler with 819 valve, Gilson 307 pump (at Column Dilution), Waters 2487 Detector (prep cell), Waters FC II (waste collection), Knauer degasser, Waters 600 pump/controller (No. 3 pump heads). | | |
| Software: | Masslynx v4.0 sp4 | | |

Preparative Method B

| Flow rate: | 40 mL/minute | | |
|---|---|---|---|
| Mobile Phase A: | water with 0.1% formic acid | | |
| Mobile Phase B: | acetonitrile with 0.1% formic acid | | |
| Column: | Waters Sunfire, C18, 30 mm × 100 mm | | |
| Particle Size: | 10 µm | | |
| Runtime: | 25.5 minutes | | |
| Inlet method: | LC7_40ml_9010_tubes.w60 | | |
| | Time (min) | % A | % B |
| Method Gradient: | 0.00 | 95 | 5 |
| | 2.00 | 95 | 5 |
| | 2.50 | 90 | 10 |
| | 18.50 | 0 | 100 |
| | 21.50 | 0 | 100 |
| | 22.50 | 95 | 5 |
| | 23.00 | 95 | 5 |

-continued

| | |
|---|---|
| ACD Flow: | 2 mL/minute (acetonitrile with 0.1% formic acid) throughout run. |
| Primary wavelength (collection): | 215 nm |
| Equipment: | Gilson 215 Liquid Handler with 819 valve, Gilson 307 pump (at Column Dilution), Waters 2487 Detector (prep cell), Waters FC II (waste collection), Knauer degasser, Waters 600 pump/controller (No. 3 pump heads). |
| Software: | Masslynx v4.0 sp4 |

Preparative Method C

| | | | |
|---|---|---|---|
| Flow rate: | 20 mL/minute | | |
| Mobile Phase A: | water | | |
| Mobile Phase B: | acetonitrile | | |
| Column: | Waters Sunfire, C18, 30 mm × 100 mm | | |
| Particle Size: | 5 μm | | |
| Runtime: | 19 minutes | | |
| | Time (min) | % A | % B |
| Method Gradient: | 0.00 | 95 | 5 |
| | 2.00 | 95 | 5 |
| | 2.50 | 90 | 10 |
| | 14.50 | 0 | 100 |
| | 16.50 | 0 | 100 |
| | 17.00 | 95 | 5 |
| | 19.00 | 95 | 5 |
| Primary wavelength (collection): | 215 nm | | |
| Secondary wavelength: | 254 nm | | |
| Equipment: | Gilson 215 Liquid Handler, Gilson 321 Pumps, Gilson 151 UV/Vis Detector. | | |
| Software: | Gilson Unipoint V5.11 | | |

Preparative Method D (High pH)

| | | | |
|---|---|---|---|
| Flow rate: | 40 mL/minute | | |
| Mobile Phase A: | acetonitrile + 0.2% ammonium hydroxide | | |
| Mobile Phase B: | acetonitrile + 0.2% ammonium hydroxide | | |
| Column: | Waters Sunfire, C18, 30 mm × 100 mm | | |
| Particle Size: | 5 μm | | |
| Runtime: | 15.5 minutes | | |
| | Time (min) | % A | % B |
| Method Gradient (isocratic): | 0.00 | 95 | 5 |
| | 2.00 | 85 | 15 |
| | 12.00 | 70 | 30 |
| | 12.50 | 5 | 95 |
| | 15.00 | 5 | 95 |
| | 15.50 | 95 | 5 |
| Primary wavelength (collection): | 215 nm | | |
| Secondary wavelength: | 254 nm | | |

Intermediate 1

1-[2-(Difluoromethoxy)phenyl]ethan-1-one

Potassium hydroxide (105 g, 1872 mmol) was suspended in a mixture of acetonitrile (200 mL) and water (200 mL) and cooled to approximately −20° C. 1-(2-Hydroxyphenyl)ethanone (11.28 mL, 93.7 mmol) was added dropwise, followed by diethyl [bromo(difluoro)methyl]phosphonate (33.27 mL, 187.3 mmol) over 15 minutes. The mixture was then allowed to warm to room temperature over 1 hour. The mixture was extracted with ethyl acetate (3×200 mL), then the combined organic layers were washed with brine (50 mL), dried over magnesium sulfate and concentrated under vacuum. The mixture was purified by flash chromatography to afford the title compound (16.0 g, 92%) as a colourless oil. Method B HPLC-MS: MH+ m/z 187, RT 1.77 minutes.

Intermediate 2

2-Bromo-1-[2-(difluoromethoxy)phenyl]ethan-1-one

A solution of bromine (1.25 mL, 24.44 mmol) in glacial acetic acid (20 mL) was added dropwise over 60 minutes to a stirring solution of Intermediate 1 (4.6 g, 24.4 mmol) in glacial acetic acid (20 mL) in the dark. When the addition was complete the reaction was diluted with DCM (200 mL) and washed with water (200 mL). The aqueous layer was then extracted with DCM (50 mL). To the combined organic layers was added saturated aqueous sodium carbonate solution (100 mL), and further solid sodium carbonate was added portionwise with vigorous stirring until the mixture was neutralised. The organic phase was separated and the aqueous layer was extracted with DCM (2×50 mL). The combined organic layers were washed with brine (50 mL), dried over sodium sulphate, filtered and concentrated under vacuum to afford the title compound (6.48 g, 82%) as a light yellow oil. $\delta_H$ (500 MHz, CDCl$_3$) 7.83 (m, 1H), 7.58 (td, J 8.3, 1.7 Hz, 1H), 7.34 (m, 1H), 7.20 (d, J 8.3 Hz, 1H), 6.64 (t, J 72.9 Hz, 1H), 4.53 (s, 2H). Method C HPLC-MS: MH+ m/z 265/267, RT 1.32 minutes.

Intermediate 3

(E)-N'-(5-Bromopyrazin-2-yl)-N,N-dimethylethenimidamide

2 Amino-5-bromopyrazine (10 g, 57.5 mmol) was suspended in toluene (250 mL). 1,1-Dimethoxy-N,N-dimethylethylamine (12.6 mL, 86.2 mmol) was added and the reaction mixture was stirred at 80° C. for 16 h. The reaction mixture was concentrated under vacuum and diluted with ethyl acetate (60 mL). The resulting material was washed with saturated aqueous sodium bicarbonate solution (40 mL), water (3×40 mL) and brine (40 mL), dried over sodium sulfate, filtered and concentrated under vacuum, to afford a brown oil. Purification by flash chromatography, eluting with heptane:EtOAc 1:0 to 2:8, afforded the title compound (11.61 g, 83%) as an off-white solid. $\delta_H$ (250 MHz, CDCl$_3$) 8.29 (d, J 1.4 Hz, 1H), 7.90 (s, 1H), 3.11 (s, 6H), 2.06 (s, 3H). Method A HPLC-MS: MH+ m/z 243/245, eluting in the solvent front.

Intermediate 4

6-Bromo-3-{[2-(difluoromethoxy)phenyl]carbonyl}-2-methylimidazo[1,2-a]pyrazine

Intermediate 3 (17.9 g, 70.1 mmol) and Intermediate 2 (11.5 g, 41.2 mmol) were taken up in anhydrous DMF (100 mL) and stirred at room temperature for 60 minutes, then stirred at 60-70° C. for a total of 2 h. The reaction mixture was allowed to cool to room temperature before being partitioned between ethyl acetate (350 mL) and water (100 mL). The organic phase was then washed with 5% w/v aqueous citric acid (4×60 mL), saturated aqueous sodium bicarbonate solution (40 mL) and brine (40 mL), then dried over sodium sulfate and concentrated under vacuum to afford a brown solid. This material was rinsed with 5% EtOAc in heptane (40 mL), then heptane (3×20 mL), and dried under vacuum to afford a light brown solid. This material was triturated twice with ethyl acetate/heptane to afford the title compound (15.75 g, 53%) as a light brown solid. δ$_H$ (500 MHz, CDCl$_3$) 9.74 (d, J 1.3 Hz, 1H), 8.99 (d, J 1.2 Hz, 1H), 7.60 (ddd, J 8.3, 7.2, 2.1 Hz, 1H), 7.43 (m, 2H), 7.35 (d, J 8.2 Hz, 1H), 6.50 (t, J 73.1 Hz, 1H), 2.13 (s, 3H). Method A HPLC-MS: MH+ m/z 382/384, RT 1.33 minutes.

Intermediate 5

(6-Bromo-2-methylimidazo[1,2-a]pyrazin-3-yl)[2-(difluoromethoxy)phenyl]methanol

Intermediate 4 (2.64 g, 6.9 mmol) was dissolved in 2:1 THF/MeOH (15 mL) and cooled to 0° C. Sodium borohydride (261 mg, 6.9 mmol) was then added, and the reaction mixture was stirred under nitrogen for 30 minutes. The reaction mixture was quenched by the addition of water (20 mL), then filtered. The resulting brown precipitate was washed with water (2×5 mL), then cold MeOH (3×3 mL). The resulting material was dried under high vacuum to afford the title compound (2.65 g, 84%) as an off-white solid. δ$_H$ (250 MHz, CDCl$_3$) 8.79 (d, J 1.2 Hz, 1H), 8.43 (d, J 1.3 Hz, 1H), 7.61 (d, J 7.4 Hz, 1H), 7.37 (ddd, J 16.4, 8.2, 6.7 Hz, 2H), 7.11 (d, J 8.0 Hz, 1H), 6.52 (m, 2H), 3.27 (s, 1H), 2.45 (s, 3H). Method A HPLC-MS: MH+ m/z 384/386, RT 1.15 minutes.

Intermediate 6

6-Bromo-3-[2-(difluoromethoxy)benzyl]-2-methyl-imidazo[1,2-a]pyrazine

Intermediate 5 (4.1 g, 10.7 mmol) was suspended in DCM (50 mL) and cooled to 0° C. under nitrogen. Thionyl bromide (1.08 mL, 13.9 mmol) was added dropwise, and the reaction mixture was allowed to warm to room temperature and was stirred for 1 h. The reaction mixture was concentrated under vacuum to afford a brown foam, which was then dissolved in anhydrous DMF (30 mL). DIPEA (5.8 mL, 33.1 mmol) was added, followed by (2,2'-bipyridine)dichlororuthenium(II) hydrate (200 mg, 0.267 mmol) and Hantzsch ester (2.97 g, 11.7 mmol). The reaction mixture was degassed by bubbling through nitrogen for approximately 5 minutes. The reaction was then sealed, placed approximately 8-10 cm from an 11 watt fluorescent lamp, and stirred for approximately 1 h. The reaction mixture was partitioned between ethyl acetate (100 mL) and water (100 mL). The layers were separated and the aqueous layer was extracted with ethyl acetate (2×30 mL). The combined organic layers were washed with brine (20 mL), dried over sodium sulfate, filtered and concentrated under vacuum to afford a yellow solid. The material obtained was purified by flash chromatography on silica, eluting with a heptane:ethyl acetate gradient from 1:0 to 9:1 to 7:3 to 4:6, to afford the title compound (2.4 g) as an off-white solid. Further product was obtained by combining mixed fractions, and concentrating under vacuum. The mixture obtained was suspended in ethyl acetate (5 mL) then sonicated. A fine precipitate formed. The mother liquor was separated and the precipitate was washed with ethyl acetate (2×2 mL). The precipitate was then dried under vacuum to afford a light brown solid (485 mg). Combined yield=2.9 g (74%). δ$_H$ (500 MHz, CDCl$_3$) 8.80 (s, 1H), 7.93 (s, 1H), 7.30 (m, 1H), 7.14 (m, 2H), 6.89 (d, J 7.2 Hz, 1H), 6.62 (t, J 73.4 Hz, 1H), 4.27 (s, 2H), 2.54 (s, 3H). Method A HPLC-MS: MH+m/z 368/370, RT 1.31 minutes.

Intermediate 7

2-Bromo-1-(2,5-dichlorophenyl)ethanone 2,5-Dichloroacetophenone (20.9 g, 0.11 mol) was dissolved in diethyl ether (300 mL) and the reaction mixture was cooled to 0° C. Bromine (5.66 mL, 0.11 mol) was added slowly dropwise and the reaction mixture was allowed to warm to room temperature over 20 minutes. The reaction mixture was treated with saturated aqueous NaHCO$_3$ solution (250 mL). The organic layer was separated, dried over MgSO$_4$ and concentrated in vacuo, yielding the title compound (20.0 g, 68%) as a yellow oil. δ$_H$ (d$_6$-DMSO) 7.94 (dd, J 2.2, 0.3 Hz, 1H), 7.61 (m, 2H), 4.88 (s, 2H).

Intermediate 8

(6-Bromo-2-methylimidazo[1,2-a]pyrazin-3-yl)(2,5-dichlorophenyl)methanone

Intermediate 3 (5.02 g, 20.65 mmol) was dissolved in ethanol (10 mL) and Intermediate 7 (7.17 g, 26.85 mmol) was added. The reaction mixture was heated at 80° C. overnight. The reaction mixture was concentrated in vacuo, and the residue was redissolved in EtOAc (100 mL) and partitioned with saturated aqueous NaHCO$_3$ solution (100 mL). The organic layer was extracted, dried over MgSO$_4$ and concentrated in vacuo. The residue was triturated with methanol, yielding the title compound (1.0 g, 12%) as a brown solid. LCMS (ES+) 386.0 (M+H)+.

Intermediate 9

5-[3-(2,5-Dichlorobenzoyl)-2-methylimidazo[1,2-a]pyrazin-6-yl]-1H-pyridin-2-one

Intermediate 8 (1.00 g, 2.68 mmol) was dissolved in a mixture of 1,4-dioxane (4 mL) and water (1 mL), and was added to a microwave vial. [1,1'-Bis(di-tert-butyl-phosphino)ferrocene]dichloropalladium(II) (84 mg, 0.13 mmol), 5-(4,4,5,5-tetramethyl-1,3,2-dioxaborolan-2-yl)-1H-pyridin-2-one (592 mg, 2.68 mmol) and 2M aqueous sodium carbonate solution (1 mL) were added. The reaction mixture was heated under microwave irradiation at 100° C. for 1 h. The reaction mixture was quenched with water (5 mL) and partitioned with DCM (10 mL). The organic layer was extracted, dried over MgSO$_4$ and concentrated in vacuo. The residue was purified by column chromatography (SiO$_2$, 0-100% EtOAc/hexane), yielding the title compound (125 mg, 12%) as a yellow solid. δ$_H$ (d$_6$-DMSO) 11.98 (s, 1H), 9.67 (d, J 1.4 Hz, 1H), 9.31 (d, J 1.4 Hz, 1H), 8.12 (d, J 2.6 Hz, 1H), 8.07 (dd, J 9.6, 2.7 Hz, 1H), 7.75 (m, 3H), 6.52 (d, J 9.6 Hz, 1H) 2.00 (s, 3H). LCMS (ES+) 400.0 (M+H)+.

Intermediate 10

5-{3-[(2,5-Dichlorophenyl)(hydroxy)methyl]-2-methylimidazo[1,2-a]pyrazin-6-yl}-1H-pyridin-2-one Intermediate 9 (120 mg, 0.30 mmol) was dissolved in ethanol (2 mL) and sodium borohydride (11 mg, 0.30 mmol) was added. The reaction mixture was stirred at room temperature for 20 minutes, then quenched with saturated aqueous NH$_4$Cl solution (5 mL). The precipitate was filtered off, washed with diethyl ether and dried under suction, yielding the title compound (144 mg, 95%) as a cream solid. δ$_H$ (d₆-DMSO) 12.15 (s, 1H), 9.09 (s, 1H), 8.96 (s, 1H), 8.23 (d, J 9.0 Hz, 1H), 8.15 (s, 1H), 8.01 (s, 1H), 7.48 (s, 1H), 7.48-7.45 (m, 1H), 6.74 (s, 1H), 6.55 (s, 1H), 6.49 (d, J 9.3 Hz, 1H) 1.88 (s, 3H). LCMS (ES+) 401.0 (M+H)$^+$.

Intermediate 11

5-(6-Methoxypyridin-3-yl)pyrazin-2-amine

2-Amino-5-bromopyrazine (5.00 g, 28.7 mmol), [1,1'-bis(diphenylphosphino)-ferrocene]palladium(II) dichloride dichloromethane adduct (0.48 g, 0.58 mmol) and 6-methoxypyridin-3-ylboronic acid (5.27 g, 34.5 mmol) were dissolved in 1,4-dioxane (100 mL) under a nitrogen atmosphere and 2M aqueous potassium carbonate solution (16 mL, 32 mmol) was added. The reaction mixture was heated at 90° C. for 4 h, then cooled to room temperature and partitioned between water (200 mL) and EtOAc (300 mL). The organic layer was separated, dried over MgSO₄ and concentrated in vacuo. The brown residue was triturated with acetonitrile (50 mL), yielding the title compound (3.52 g, 61%) as a brown solid. $\delta_H$ (d₆-DMSO) 8.69 (d, J 2.1 Hz, 1H), 8.48 (d, J 1.4 Hz, 1H), 8.19 (dd, J 8.7, 2.5 Hz, 1H), 7.96 (d, J 1.4 Hz, 1H), 6.87 (d, J 8.7 Hz, 1H), 6.54 (s, 2H), 3.89 (s, 3H). LCMS (ES+) 203.0 (M+H)$^+$.

Intermediate 12

N'-[5-(6-Methoxypyridin-3-yl)pyrazin-2-yl]-N,N-dimethylacetamidine

Intermediate 11 (1.0 g, 4.9 mmol) was suspended in methanol (5 mL) and N,N-dimethylacetamide dimethyl acetal (3.7 g, 4.1 mL, 25 mmol) was added. The reaction mixture was heated at 80° C. overnight. The reaction mixture was concentrated in vacuo, then the residue was dissolved in EtOAc (20 mL) and partitioned with saturated aqueous NaHCO₃ solution (50 mL). The organic layer was extracted, dried over MgSO₄ and concentrated in vacuo. The residue was purified by column chromatography (SiO₂, 0-100% EtOAc/hexane), yielding the title compound (0.91 g, 68%) as a yellow solid. $\delta_H$ (d₆-DMSO) 8.82 (m, 2H), 8.31 (dd, J 8.7, 2.5 Hz, 1H), 8.08 (s, 1H), 6.92 (d, J 8.7 Hz, 1H), 3.91 (s, 3H), 3.08 (s, 6H), 2.07 (s, 3H). LCMS (ES$^+$) 272.0 (M+H)$^+$.

Intermediate 13

[2-(Difluoromethoxy)phenyl][6-(6-methoxypyridin-3-yl)-2-methylimidazo[1,2-a]pyrazin-3-yl]methanone Intermediate 12 (0.91 g, 3.38 mmol) and Intermediate 2 (0.895 g, 3.38 mmol) were dissolved in ethanol (5 mL) and heated to reflux for 18 h. The reaction mixture was concentrated in vacuo and the residue was partitioned between saturated aqueous NaHCO₃ solution (20 mL) and EtOAc (50 mL). The organic layer was separated, dried over MgSO₄ and concentrated in vacuo. The residue was purified by column chromatography (SiO₂, 0-100% EtOAc/hexane), yielding the title compound (0.18 g, 13%) as an orange oil. $\delta_H$ (CDCl₃) 9.92 (d, J 1.4 Hz, 1H), 9.26 (d, J 1.4 Hz, 1H), 8.87 (d, J 2.3 Hz, 1H), 8.25 (dd, J 8.7, 2.5 Hz, 1H), 7.61 (m, 1H), 7.48 (m, 1H), 7.41 (m, 2H), 6.92 (m, 1H), 6.35 (s, 1H), 4.05 (s, 3H), 2.15 (s, 3H). LCMS (ES$^+$) 411.0 (M+H)$^+$.

Intermediate 14 tert-Butyl 4-(5-{3-[2-(difluoromethoxy)benzyl]-2-methylimidazo[1,2-a]pyrazin-6-yl}pyrimidin-2-yl)piperazine-1-carboxylate Intermediate 6 (100 mg, 0.27 mmol) and tert-butyl 4-[5-(4,4,5,5-tetramethyl-1,3,2-dioxaborolan-2-yl)pyrimidin-2-yl]piperazine-1-carboxylate (88 mg, 0.225 mmol) were dissolved in 1,4-dioxane (4 mL) and 2M aqueous potassium carbonate solution (475 µL) was added. The reaction mixture was degassed with nitrogen for 5 minutes, then bis[3-(diphenylphosphanyl)cyclopenta-2,4-dien-1-yl]iron; dichloromethane; dichloropalladium (11.1 mg, 0.01 mmol) was added. The reaction was heated at 90° C. for 8.5 h in a sealed tube under nitrogen. The mixture was diluted with EtOAc (20 mL) and washed with water (15 mL). The aqueous phase was diluted with water (15 mL) and extracted with EtOAc (20 mL). The combined organic layers were washed with brine (10 mL), dried over magnesium sulfate and concentrated under vacuum. The crude product was purified by column chromatography, eluting with heptanes:ethyl acetate 1:0 to 1:1, to yield the title compound (81 mg, 50%). $\delta_H$ (250 MHz, CDCl₃) 9.07 (s, 1H), 8.76 (s, 2H), 7.95 (d, J 1.4 Hz, 1H), 7.31 (d, J 7.4 Hz, 1H), 7.13 (m, 2H), 6.94 (m, 1H), 6.64 (t, J 29 Hz, 1H), 4.33 (s, 2H), 3.87 (m, 4H), 3.51 (m, 4H), 2.58 (s, 3H), 1.49 (s, 9H). Method A HPLC-MS: MH+ m/z 552, RT 5.01 minutes.

Intermediate 15

[2-(3-Oxopiperazin-1-yl)pyrimidin-5-yl]boronic acid (2-Chloropyrimidin-5-yl)boronic acid (1.0 g, 6.32 mmol) and piperazin-2-one (1.6 g, 16.0 mmol) were suspended in 1,4-dioxane (10 mL) and the mixture was heated at 100° C. under microwave irradiation for 45 minutes. The supernatant liquid was decanted from the suspension and the residue was triturated with methanol and diethyl ether. The resultant solids were filtered off and dried under vacuum to afford the title compound (706 mg, 30%) as a pale pink solid. LCMS: MH+223.

Intermediate 16

[2-(5-Oxo-1,4-diazepan-1-yl)pyrimidin-5-yl]boronic acid (2-Chloropyrimidin-5-yl)boronic acid (200 mg, 1.26 mmol) and 1,4-diazepan-5-one (288 mg, 2.53 mmol) were suspended in 1,4-dioxane (3 mL) and the mixture was heated at 100° C. under microwave irradiation for 45 minutes. The resulting slurry was concentrated under vacuum and triturated with MeOH to afford the title compound as a cream precipitate, which was used without further purification. LCMS: MH+237.

Intermediate 17 tert-Butyl 4-(4,4,5,5-tetramethyl-1,3,2-dioxaborolan-2-yl)-1,2,3,6-tetrahydropyridine-1-carboxylate tert-Butyl 4-[(trifluoromethane)sulfonyloxy]-1,2,3,6-tetrahydropyridine-1-carboxylate (500 mg, 1.51 mmol), 4,4,5,5-tetramethyl-2-(4,4,5,5-tetramethyl-1,3,2-dioxaborolan-2-yl)-1,3,2-dioxaborolane (460 mg, 1.81 mmol), 1,1'-bis(diphenyl-phosphanyl)ferrocene (25 mg, 0.05 mmol) and potassium acetate (444 mg, 4.53 mmol) were dissolved in 1,4-dioxane (10 mL) and degassed for 5 minutes. Bis[3-(diphenyl-phosphanyl)cyclopenta-2,4-dien-1-yl]iron dichloropalladium dichloromethane complex (37 mg, 0.05 mmol) was added and the mixture was heated at 80° C. for 3 h. The mixture was filtered through celite and concentrated under reduced pressure. The residue was purified by FCC (eluting with EtOAc in heptanes) to afford the title compound (332 mg, 71%) as a white solid. $\delta_H$ (500 MHz, CDCl$_3$) 6.46 (s, 1H), 3.95 (q, J 2.8 Hz, 2H), 3.43 (t, J 5.6 Hz, 2H), 2.22 (dq, J 5.5, 2.8 Hz, 2H), 1.46 (s, 9H), 1.26 (s, 12H).

Intermediate 18

2-Chloro-5-(3-{[2-(difluoromethoxy)phenyl]methyl}-2-methylimidazo[1,2-a]pyrazin-6-yl)pyridine Intermediate 6 (200 mg, 0.54 mmol), (6-chloropyridin-3-yl)boronic acid (90 mg, 0.57 mmol) and 2M aqueous potassium carbonate solution (0.95 mL) were combined in 1,4-dioxane (8 mL) and bis[3-(diphenylphosphanyl)cyclopenta-2,4-dien-1-yl]iron dichloropalladium dichloromethane complex (22 mg, 0.03 mmol) was added. The mixture was heated at 90° C. for 8.5 h. The mixture was partitioned between EtOAc (20 mL) and water (15 mL) and the phases were separated. The aqueous phase was diluted with water (~15 mL) and extracted with EtOAc (20 mL). The combined organic phases were washed with brine (10 mL) and dried over magnesium sulfate, then concentrated under vacuum. The residue was purified by FCC, eluting with 0-100% EtOAc in heptanes, to afford the title compound (92.6 mg, 38%) as an off-white solid. The crude material was used without further purification. Method C HPLC-MS: MH+ m/z 401, RT 1.30 minutes.

Intermediate 19 tert-Butyl 3-(4,4,5,5-tetramethyl-1,3,2-dioxaborolan-2-yl)-8-azabicyclo[3.2.1]oct-2-ene-8-carboxylate tert-Butyl 3-[(trifluoromethane)sulfonyloxy]-8-azabicyclo[3.2.1]oct-2-ene-8-carboxylate (100 mg, 0.28 mmol), 4,4,5,5-tetramethyl-2-(4,4,5,5-tetramethyl-1,3,2-dioxaborolan-2-yl)-1,3,2-dioxaborolane (85 mg, 0.36 mmol), 1,1'-bis(diphenyl-phosphanyl)ferrocene (5 mg, 0.01 mmol) and potassium acetate (82 mg, 0.84 mmol) were dissolved in 1,4-dioxane (2 mL) and degassed for 5 minutes. Bis[3-(diphenyl-phosphanyl)cyclopenta-2,4-dien-1-yl]iron dichloropalladium dichloromethane complex (7 mg, 0.01 mmol) was added and the mixture was heated at 80° C. for a total of 3 h. The reaction mixture was cooled and filtered over celite. The solid was washed with EtOAc (2×10 mL) and the combined filtrate was concentrated under vacuum. The crude product was purified using FCC, eluting with a gradient of 0-50% EtOAc in heptanes, to afford the title compound (86.8 mg, 89%) as a colourless oil. $\delta_H$ (500 MHz, CDCl$_3$) 6.76 (s, 1H), 4.33 (d, J 29.8 Hz, 2H), 2.79 (d, J 17.5 Hz, 1H), 2.12 (dd, J 13.3, 7.3 Hz, 1H), 1.92 (m, 2H), 1.65 (m, 2H), 1.46 (d, J 7.1 Hz, 9H), 1.26 (d, J 6.3 Hz, 12H).

Intermediate 20

Methyl 2-{4-[5-(3-{[2-(difluoromethoxy)phenyl]methyl}-2-methylimidazo[1,2-a]-pyrazin-6-yl)pyrimidin-2-yl]piperazin-1-yl}acetate The hydrochloride salt of Example 4 (200 mg, 0.41 mmol) was dissolved in DMF (4 mL) and caesium carbonate (401 mg, 1.23 mmol) was added. The resulting mixture was stirred under nitrogen for 5 minutes, then methyl bromoacetate (35 μL, 0.37 mmol) was added and the reaction mixture was stirred under nitrogen for 2.5 h. The reaction mixture was diluted with water (10 mL) and extracted with EtOAc (20 mL). The organic layer was washed with brine (2×10 mL), dried over sodium sulfate and concentrated to dryness. The residue was triturated with DCM to yield the title compound (118 mg, 55%). $\delta_H$ (500 MHz, CD$_3$OD) 8.92 (s, 1H), 8.84 (s, 2H), 8.52 (s, 1H), 7.37-7.30 (m, 1H), 7.26-7.16 (m, 3H), 6.93 (t, J 73.9 Hz, 1H), 4.47 (s, 2H), 3.97-3.91 (m, 4H), 3.75 (s, 3H), 3.34 (s, 2H), 2.71-2.65 (m, 4H), 2.47 (s, 3H).

Intermediate 21 tert-Butyl 4-[5-(3-{[2-(difluoromethoxy)phenyl](hydroxy)methyl}-2-methylimidazo[1,2-a]pyrazin-6-yl)pyridin-2-yl]piperazine-1-carboxylate tert-Butyl 4-[5-(4,4,5,5-tetramethyl-1,3,2-dioxaborolan-2-yl)pyridin-2-yl]-piperazine-1-carboxylate (101 mg, 0.26 mmol) and Intermediate 5 (100 mg, 0.26 mmol) were added to degassed 1,4-dioxane (1.5 mL) in a sealed tube. Degassed 1M aqueous sodium carbonate solution (0.781 mL, 0.781 mmol) was added, followed by bis(triphenylphosphine)palladium(II) dichloride (9 mg, 0.013 mmol), and the reaction mixture was heated under nitrogen at 100° C. for 8 h. The reaction mixture was diluted with EtOAc (15 mL) and the organic layer was washed with saturated aqueous sodium bicarbonate solution (6 mL) followed by brine (6 mL), then dried over sodium sulfate and concentrated. The residue was purified by FCC, eluting with a gradient of 0-2.5% (7M NH$_3$ in MeOH) in DCM, to afford the title compound (117 mg, 77%) as a light brown glass. $\delta_H$ (500 MHz, CDCl$_3$) 8.80 (m, 1H), 8.39 (d, J 2.3 Hz, 1H), 8.35 (m, 1H), 7.91 (m, 2H), 7.33 (m, 2H), 7.04 (m, 1H), 6.63 (d, J 8.9 Hz, 1H), 6.38 (m, 2H), 5.50 (s, 1H), 3.53 (m, 8H), 2.28 (s, 3H), 1.47 (s, 9H).

Intermediate 22

1-[5-(Dihydroxyboranyl)pyrimidin-2-yl]piperidine-4-carboxylic acid (2-Chloropyrimidin-5-yl)boronic acid (1 g, 6.32 mmol) was dissolved in EtOH (15 mL) and piperidine-4-carboxylic acid (816 mg, 6.32 mmol) was added, followed by triethylamine (881 μL, 6.32 mmol). The reaction mixture was heated at 80° C. for a total of 4 h. The reaction mixture was concentrated to dryness and 10 mL of water was added. The resulting suspension was cooled to 0° C. for 30 minutes, then filtered, and the solid was washed with minimal water. Only a trace amount of precipitate was isolated so this was recombined with the filtrate and concentrated to dryness to afford the title compound. The crude product was used without purification. Method C HPLC-MS: MH+ m/z 252, RT 0.70 minutes.

Intermediate 23

{2-[(1R,5S,6r)-6-(Ethoxcarbonyl)-3-azabicyclo[3.1.0]hexan-3-yl]pyrimidin-5-yl}-boronic acid (2-Chloropyrimidin-5-yl)boronic acid (250 mg, 1.58 mmol), ethyl (1R,5S,6r)-3-azabicyclo[3.1.0]hexane-6-carboxylate hydrochloride (303 mg, 1.58 mmol) and triethylamine (0.22 mL, 1.58 mmol) were dissolved in ethanol (8 mL) and stirred at 80° C. overnight. The reaction mixture was cooled and concentrated under vacuum. Water (30 mL) was added, and the solid was filtered and dried, to afford the title compound (253 mg, 58%) as a pale brown solid. Method B HPLC-MS: MH+ m/z 278, RT 1.35 minutes.

Intermediate 24

{2-[4-(Ethoxycarbonyl)piperidin-1-yl]pyrimidin-5-yl}boronic acid (2-Chloropyrimidin-5-yl)boronic acid (2 g, 12.63 mmol) and ethyl piperidine-4-carboxylate (1.94 mL, 12.63 mmol) were dissolved in 1,4-dioxane (20 mL) and heated at 60° C. under microwave irradiation for 1 h. The reaction mixture was concentrated to dryness and partitioned between EtOAc and water. The organic layer was separated, washed with brine, dried over sodium sulfate and concentrated to dryness, to afford the title compound (1.79 g, 51%) as a yellow gum. Method C HPLC-MS: MH+ m/z 280, RT 0.94 minutes.

Intermediate 25

Ethyl (1R,5S,6r)-3-[5-(3-{[2-(difluoromethoxy)phenyl]methyl}-2-methylimidazo[1,2-a]-pyrazin-6-yl)pyrimidin-2-yl]-3-azabicyclo[3.1.0]hexane-6-carboxylate Intermediate 6 (120 mg, 0.32 mmol), Intermediate 23 (117 mg, 0.42 mmol) and 2M aqueous potassium carbonate solution (0.51 mL) were stirred in 1,4-dioxane (5 mL). The mixture was thoroughly degassed before the addition of bis[3-(diphenylphosphanyl)-cyclopenta-2,4-dien-1-yl]iron dichloropalladium dichloromethane complex (13 mg, 0.01 mmol). The mixture was heated at 100° C. for 15 h. The reaction mixture was cooled to r.t. and EtOAc (10 mL) was added. The solution was washed with water (2×10 mL) and brine (10 mL), dried over sodium sulfate, then concentrated under vacuum. The residue was purified by FCC, eluting with a gradient of 0-7% MeOH in DCM, to afford the title compound (122 mg, 72%) as a pale orange oil. $\delta_H$ (500 MHz, CDCl$_3$) 9.04 (s, 1H), 8.74 (d, J 5.7 Hz, 2H), 7.91 (s, 1H), 7.31-7.26 (m, 1H), 7.17 (d, J 8.0 Hz, 1H), 7.12 (t, J 7.5 Hz, 1H), 6.93 (d, J 7.6 Hz, 1H), 6.63 (t, J 73.5 Hz, 1H), 4.32 (s, 2H), 4.14 (q, J 7.1 Hz, 2H), 4.03 (d, J 11.5 Hz, 2H), 3.70-3.64 (m, 2H), 2.57 (s, 3H), 2.29-2.22 (m, 2H), 1.59-1.52 (m, 1H), 1.26 (t, J 7.3 Hz, 3H). Method D HPLC-MS: MH+ m/z 520, RT 3.32 minutes.

Intermediate 26

{2-[4-(Ethoxycarbonyl)-4-methylpiperidin-1-yl]pyrimidin-5-yl}boronic acid (2-Chloropyrimidin-5-yl)boronic acid (321 mg, 2.03 mmol) and ethyl 4-methylpiperidine-4-carboxylate (347 mg, 2.03 mmol) were stirred in 1,4-dioxane (6 mL) and the mixture was degassed with nitrogen for 5 minutes. The tube was sealed and heated under microwave irradiation for 30 minutes at 65° C. Further (2-chloropyrimidin-5-yl)boronic acid (36 mg, 0.23 mmol) was added and the mixture was heated under microwave irradiation for 30 minutes at 65° C. The mixture was concentrated to afford the title compound, which was used without further purification. Method C HPLC-MS: MH+ m/z 294, RT 1.09 minutes.

Intermediate 27

{2-[4-Hydroxy-4-(methoxycarbonyl)piperidin-1-yl]pyrimidin-5-yl}boronic acid (2-Chloropyrimidin-5-yl)boronic acid (0.25 g, 1.579 mmol) and methyl 4-hydroxypiperidine-4-carboxylate (0.528 g, 3.315 mmol) were dissolved in DMSO (5 mL) and heated at 70° C. under microwave irradiation for 50 minutes. The mixture was diluted with EtOAc (45 mL) and washed with saturated aqueous ammonium chloride solution (3×6 mL), water (6 mL) and brine (10 mL), then dried over sodium sulfate and concentrated, to afford the title compound (230 mg, 48%) as a brown gum. Method C HPLC-MS: MH+ m/z 282, RT 0.70 minutes.

Intermediate 28

1-{6-Bromo-2-methylimidazo[1,2-a]pyrazin-3-yl}-1-[2-(difluoromethoxy)phenyl]ethanol Intermediate 4 (924 mg, 2.42 mmol) was dissolved in THF (10 mL) and cooled to 0° C. under nitrogen. Methylmagnesium bromide in THF/toluene (3.11 mL of a 1.4M solution) was added at 0° C. under nitrogen and the reaction mixture was stirred for 1 h at 0° C. under nitrogen. Further methylmagnesium bromide in THF/toluene (1.55 mL of a 1.4M solution) was added at 0° C. under nitrogen and the reaction mixture was stirred at 0° C. under nitrogen for 10 minutes. The reaction mixture was carefully quenched by addition of saturated aqueous ammonium chloride solution (15 mL) at 0° C., and extracted into EtOAc (25 mL). The organic layer was separated, washed with brine (15 mL), dried over sodium sulfate and concentrated to dryness. The residue was triturated with DCM (5 mL) to afford an off-white solid. The filtrate was purified by FCC, eluting with 20-100% EtOAc in heptanes, to afford the title compound (360 mg, 37%) as a yellow gum. $\delta_H$ (500 MHz, CD$_3$OD) 8.65 (s, 1H), 8.35 (d, J 1.3 Hz, 1H), 8.17-8.11 (m, 1H), 7.44-7.37 (m, 2H), 7.10-7.04 (m, 1H), 6.71-6.37 (m, 1H), 2.66 (s, 3H), 2.13 (s, 3H). Method C HPLC-MS: MH+ m/z 398/400, RT 1.19 minutes.

Intermediate 29

Ethyl 1-[5-(3-{1-[2-(difluoromethoxy)phenyl]-1-hydroxyethyl}-2-methylimidazo[1,2-a]-pyrazin-6-yl)pyrimidin-2-yl]piperidine-4-carboxylate Intermediate 28 (180 mg, 0.45 mmol), Intermediate 24 (189.24 mg, 0.68 mmol) and 2M aqueous potassium carbonate solution (0.9 mL) were suspended in 1,4-dioxane (10 mL). The mixture was purged with nitrogen for 5 minutes, then bis[3-(diphenyl-phosphanyl)cyclopenta-2,4-dien-1-yl]iron dichloropalladium dichloromethane complex (18 mg, 0.02 mmol) was added and the mixture was heated at 100° C. for 4 h. The mixture was cooled to r.t., filtered through celite and concentrated under reduced pressure. The residue was purified by preparative HPLC to afford the title compound (85 mg, 34%) as a pale yellow solid. $\delta_H$ (500 MHz, DMSO-d$_6$) 8.94 (d, J 1.1 Hz, 1H), 8.55 (s, 2H), 8.27 (d, J 1.1 Hz, 1H), 8.22 (dd, J 7.8, 1.6 Hz, 1H), 7.51-7.25 (m, 2H), 7.15-6.70 (m, 2H), 6.47 (s, 1H), 4.55 (d, J 13.4 Hz, 2H), 4.08 (q, J 7.1 Hz, 2H), 3.26-2.98 (m, 2H), 2.70-2.62 (m, 1H), 2.61 (s, 3H), 2.07 (s, 3H), 1.90 (d, J 10.2 Hz, 2H), 1.50 (q, J 11.1 Hz, 2H), 1.19 (t, J 7.1 Hz, 3H). Method B HPLC-MS: MH+ m/z 553, RT 1.95 minutes.

Intermediate 30

Ethyl 1-[5-(3-{1-[2-(difluoromethoxy)phenyl]ethenyl}-2-methylimidazo[1,2-a]pyrazin-6-yl)pyrimidin-2-yl]piperidine-4-carboxylate Intermediate 29 (80 mg, 0.14 mmol) and 4-methylbenzenesulfonic acid monohydrate (6 mg, 0.03 mmol) were dissolved in toluene (3 mL) and the mixture was heated at 80° C. for 4 h, then at 120° C. for 2 h. The mixture was concentrated under reduced pressure and purified by preparative HPLC to afford the title compound (25 mg, 32%) as an off-white solid. $\delta_H$ (500 MHz, CDCl$_3$) 9.03 (d, J 14.9 Hz, 1H), 8.59 (s, 2H), 7.73 (s, 1H), 7.49-7.37 (m, 2H), 7.36-7.30 (m, 1H), 7.14 (d, J 8.3 Hz, 1H), 6.18 (t, J 73.4 Hz, 1H), 5.99 (s, 1H), 5.76 (s, 1H), 4.69 (dt, J 13.5, 3.5 Hz, 2H), 4.15 (q, J 7.1 Hz, 2H), 3.17-3.00 (m, 2H), 2.58 (tt, J 11.0, 3.9 Hz, 1H), 2.46 (s, 3H), 1.99 (dd, J 13.5, 3.3 Hz, 2H), 1.71 (qd, J 11.4, 4.1 Hz, 2H), 1.26 (t, J 7.1 Hz, 3H). Method B HPLC-MS: MH+ m/z 535, RT 2.35 minutes.

Intermediate 31

Ethyl 1-[5-(3-{1-[2-(difluoromethoxy)phenyl]ethyl}-2-methylimidazo[1,2-a]pyrazin-6-yl)pyrimidin-2-yl]piperidine-4-carboxylate Intermediate 30 (25 mg, 0.05 mmol) was dissolved in ethanol (50 mL), then palladium on carbon (10% w/w, 5 mg) was added. The suspension was degassed using vacuum/nitrogen and the mixture was stirred under hydrogen at r.t. for 14 h. The reaction mixture was then degassed using vacuum/nitrogen and filtered through celite, washing with MeOH (15 mL). The solvent was removed under reduced pressure to afford the title compound (25 mg) as a pale yellow sticky solid. LCMS showed that the conversion had not gone to completion, and the crude product was used without purification. Method B HPLC-MS: MH+ m/z 537, RT 2.25 minutes.

Intermediate 32

6-Bromo-3-{[2-(difluoromethoxy)phenyl](methoxy)methyl}-2-methylimidazo[1,2-a]-pyrazine Intermediate 5 (1.44 g, 3.75 mmol) was stirred in anhydrous DCM (50 mL) under nitrogen and the mixture was cooled with an ice bath. Thionyl bromide (0.38 mL, 4.87 mmol) was added slowly, then the mixture was allowed to warm to r.t. and stirred for 1 h. The mixture was then cooled with an ice bath and anhydrous MeOH (15.43 mL, 0.38 mol) was added slowly. The mixture was stirred for 30 minutes. The mixture was reduced to dryness under vacuum and the flask was flushed with nitrogen. Anhydrous DCM (50 mL) was added, the mixture was cooled and thionyl bromide (0.1 mL, 1.3 mmol) was added. The mixture was stirred at r.t. for 1 h before being quenched with MeOH and concentrated under vacuum to afford the title compound (1.06 g, 71%). Method C HPLC-MS: MH+ m/z 398/400, RT 1.35 minutes.

Intermediate 33

(2-{7-Oxo-3,6-diazabicyclo[3.2.2]nonan-3-yl}pyrimidin-5-yl)boronic acid triethyl-azanium chloride (2-Chloropyrimidin-5-yl)boronic acid (1.13 g, 7.14 mmol) and (1S,5R)-3,6-diazabicyclo[3.2.2]nonan-7-one (1.00 g, 7.13 mmol) were mixed together in ethanol (15 mL) and triethylamine (1.00 mL, 7.10 mmol) was added. The mixture was heated to 80° C. for 3 days. The mixture was concentrated in vacuo to afford the title compound (2.70 g, UV purity 94.7%) as an off-white solid, which was used in subsequent coupling reactions without any further purification. $\delta_H$ (300 MHz, DMSO-d$_6$) 10.54-9.53 (br s, 2H), 8.08 (s, 2H), 4.88-4.74 (m, 2H), 3.65-3.53 (m, 1H), 3.48-3.39 (m, 1H), 3.24-3.11 (m, 2H), 3.03 (q, J 7.3 Hz, 6H), 2.59-2.52 (m, 1H), 1.78-1.53 (m, 4H), 1.19 (t, J 7.3 Hz, 9H).

Intermediate 34 tert-Butyl 4-[5-(3-{[2-(difluoromethoxy)phenyl]methyl}-2-methylimidazo[1,2-a]pyrazin-6-yl)pyridin-2-yl]piperazine-1-carboxylate Intermediate 6 (100 mg, 0.27 mmol) and tert-butyl 4-[5-(4,4,5,5-tetramethyl-1,3,2-dioxaborolan-2-yl)pyridin-2-yl]piperazine-1-carboxylate (159 mg, 0.41 mmol) were combined in 1,4-dioxane (7 mL) and the mixture was degassed before the addition of 2M aqueous potassium carbonate solution (0.473 mL) and bis[3-(diphenylphosphanyl)-cyclopenta-2,4-dien-1-yl]iron dichloropalladium dichloromethane complex (11 mg, 0.014 mmol). The mixture was heated at 90° C. for 4 h in a sealed tube, then left to stand at r.t. for 4 days. The mixture was heated at 90° C. for 2 h, then at 100° C. for a total of 8 h. The mixture was partitioned between EtOAc (20 mL) and water (15 mL). The aqueous layer was diluted with water (~15 mL) and extracted with EtOAc (20 mL). The combined organic layers were washed with brine (10 mL), dried over magnesium sulfate and concentrated under vacuum. The residue was purified by FCC, eluting with 0-100% EtOAc in heptanes. The residue was then twice purified by FCC, eluting with mixtures of MeOH in DCM, to afford the title compound (35 mg, 22%) as a white solid. Method B HPLC-MS: MH+ m/z 551, RT 2.10 minutes.

Intermediate 35

4-(3-{[2-(Difluoromethoxy)phenyl]methyl}-2-methylimidazo[1,2-a]pyrazin-6-yl)-piperidine hydrochloride Example 9 (700 mg, 1.48 mmol) was suspended in 4M HCl in 1,4-dioxane (3.7 mL) and the mixture was stirred at r.t. for 2 h. The mixture was concentrated under reduced pressure and dried under vacuum, to afford the title compound (595 mg, 98%) as a sticky beige solid. Method B HPLC-MS: MH+ m/z 373, RT 1.21 minutes.

Intermediate 36

3-{[2-(Difluoromethoxy)phenyl]methyl}-6-(6-fluoro-4-methylpyridin-3-yl)-2-methyl-imidazo[1,2-a]pyrazine Intermediate 6 (600 mg, 1.63 mmol) and (6-fluoro-4-methylpyridin-3-yl)boronic acid (375 mg, 2.42 mmol) were dissolved in a mixture of 1,4-dioxane (3 mL) and 2M aqueous potassium carbonate solution (2.5 mL). The mixture was flushed with nitrogen, then bis[3-(diphenylphosphanyl)cyclopenta-2,4-dien-1-yl]iron dichloropalladium dichloromethane complex (100 mg, 0.12 mmol) was added and the mixture was heated at 90° C. for 15 h. The mixture was diluted with EtOAc (20 mL), then washed with water (2×10 mL) and brine (10 mL). The organic layer was dried over sodium sulfate and concentrated under vacuum. The resulting dark brown solid was purified by FCC, eluting with 70-100% EtOAc in heptanes followed by 0-10% MeOH in DCM, to afford the title compound (422 mg, 65%) as a light pink solid. $\delta_H$ (500 MHz, CD$_3$OD) 8.95 (d, J 1.2 Hz, 1H), 8.33 (d, J 1.2 Hz, 1H), 8.13 (s, 1H), 7.35-7.28 (m, 1H), 7.23-7.14 (m, 3H), 7.06 (s, 1H), 6.86 (t, J 74.0 Hz, 1H), 4.44 (s, 2H), 2.48 (s, 3H), 2.36 (s, 3H). Method D HPLC-MS: MH+ m/z 399, RT 3.29 minutes.

Intermediate 37

5-(3-{[2-(Difluoromethoxy)phenyl]methyl}-2-methylimidazo[1,2-a]pyrazin-6-yl)-2-fluoropyridine A mixture of Intermediate 6 (50 mg, 0.14 mmol), (6-fluoropyridin-3-yl)boronic acid (29 mg, 0.2 mmol) and 2M aqueous sodium carbonate solution (0.10 mL) in acetonitrile (1.0 mL) was purged with nitrogen for 5 minutes. Bis[3-(diphenyl-phosphanyl)cyclopenta-2,4-dien-1-yl]iron dichloropalladium dichloromethane complex (3 mg, 2.5 mol %) was added, then the reaction mixture was heated at 150° C. under microwave irradiation for 30 minutes. The reaction mixture was partitioned between EtOAc (5 mL) and water (3 mL). The aqueous layer was separated and extracted with EtOAc (5 mL). The combined organic extracts were washed with brine (5 mL), dried over sodium sulfate and evaporated. The residue was purified by FCC, eluting with 20-100% EtOAc in heptanes, to afford the title compound (41 mg, 79%) as a yellow solid. $\delta_H$ (500 MHz, CD$_3$OD) 8.97 (d, J 1.2 Hz, 1H), 8.76 (d, J 2.4 Hz, 1H), 8.70 (d, J 1.4 Hz, 1H), 8.53-8.44 (m, 1H), 7.37-7.28 (m, 1H), 7.26-7.15 (m, 4H), 7.07-6.69 (m, 1H), 4.48 (s, 2H), 2.46 (s, 3H). Method B HPLC-MS: MH+ m/z 385, RT 1.94 minutes.

Intermediate 38

Ethyl 1-[5-(3-{[2-(difluoromethoxy)phenyl]methyl}-2-methylimidazo[1,2-a]pyrazin-6-yl)pyridin-2-yl]piperidine-4-carboxylate A mixture of Intermediate 37 (38 mg, 0.1 mmol) and ethyl piperidine-4-carboxylate (30.5 μL, 0.2 mmol) in pyridine (0.5 mL) was heated at 180° C. under microwave irradiation for a total of 3 h. The reaction mixture was evaporated and the residue was purified by FCC, eluting with 50-100% EtOAc in heptanes, to afford the title compound (38 mg, 74%) as an off-white solid. $\delta_H$ (500 MHz, CD$_3$OD) 8.90 (d, J 1.4 Hz, 1H), 8.60 (d, J 2.2 Hz, 1H), 8.41 (d, J 1.4 Hz, 1H), 8.04 (dd, J 9.0, 2.5 Hz, 1H), 7.38-7.27 (m, 1H), 7.19 (td, J 8.0, 6.2 Hz, 3H), 7.11-6.67 (m, 2H), 4.45 (s, 2H), 4.28 (dt, J 13.4, 3.6 Hz, 2H), 4.15 (q, J 7.1 Hz, 2H), 3.12-3.01 (m, 2H), 2.64 (tt, J 11.0, 3.9 Hz, 1H), 2.47 (s, 3H), 2.05-1.95 (m, 2H), 1.72 (qd, J 11.3, 4.0 Hz, 2H), 1.27 (t, J 7.1 Hz, 3H). Method B HPLC-MS: MH+ m/z 522, RT 1.87 minutes.

Intermediate 39

Ethyl 1-[5-(3-{[2-(difluoromethoxy)phenyl]methyl}-2-methylimidazo[1,2-a]pyrazin-6-yl)pyridin-2-yl]-4-methylpiperidine-4-carboxylate A mixture of Intermediate 37 (200 mg, 0.52 mmol) and ethyl 4-methylpiperidine-4-carboxylate hydrochloride (216 mg, 1.04 mmol) in pyridine (0.5 mL) was heated at 180° C. under microwave irradiation for 4 h. The reaction mixture was concentrated and the residue was purified by FCC, eluting with 20-100% EtOAc in heptanes, to afford the title compound (131 mg, 47%) as an off-white solid. $\delta_H$ (500 MHz, CD$_3$OD) 8.88 (d, J 1.4 Hz, 1H), 8.57 (d, J 2.3 Hz, 1H), 8.37 (d, J 1.4 Hz, 1H), 8.01 (dd, J 9.0, 2.5 Hz, 1H), 7.31 (ddd, J 8.6, 6.8, 2.3 Hz, 1H), 7.26-7.11 (m, 3H), 7.08-6.71 (m, 2H), 4.43 (s, 2H), 4.19 (q, J 7.1 Hz, 2H), 4.01 (dt, J 13.7, 4.2 Hz, 2H), 3.18 (ddd, J 13.6, 10.7, 2.9 Hz, 2H), 2.46 (s, 3H), 2.17 (d, J 13.6 Hz, 2H), 1.51 (ddd, J 14.1, 10.7, 4.0 Hz, 2H), 1.27 (t, J 7.1 Hz, 3H), 1.23 (s, 3H). Method B HPLC-MS: MH+ m/z 536, RT 1.96 minutes.

Intermediate 40

(2,5-Dichlorophenyl)[2-methyl-6-(1-methylpyrazol-4-yl)imidazo[1,2-a]pyrazin-3-yl]-methanone To Intermediate 8 (1 g, 2.68 mmol) in 1,4-dioxane (4 mL) and water (1 mL) were added 1-methyl-4-(4,4,5,5-tetramethyl-1,3,2-dioxaborolan-2-yl)pyrazole (556 mg, 2.68 mmol), dichloro[1,1'-bis(di-tert-butylphosphino)]ferrocenepalladium(II) (84 mg, 0.13 mmol) and aqueous sodium carbonate solution (2M, 1 mL) and the reaction mixture was heated under microwave irradiation at 100° C. for 1 h. The cooled reaction mixture was partitioned between water and DCM, then the organic layer was dried over magnesium sulfate and concentrated in vacuo. The crude residue was purified by column chromatography (SiO$_2$, EtOAc:DCM, 0 to 100%) to afford the title compound (254 mg, 25%) as a cream solid. $\delta_H$ (400 MHz, DMSO-d$_6$) 9.63 (d, J 1.5 Hz, 1H), 9.29 (d, J 1.4 Hz, 1H), 8.41 (s, 1H), 8.03 (d, J 0.5 Hz, 1H), 7.80-7.79 (m, 1H), 7.73 (d, J 1.1 Hz, 2H), 3.93 (s, 3H), 1.99 (s, 3H). HPLC-MS: MH+ m/z 386.0, RT 2.22 minutes.

Intermediate 41

(2,5-Dichlorophenyl)[2-methyl-6-(1-methylpyrazol-4-yl)imidazo[1,2-a]pyrazin-3-yl]-methanol To Intermediate 40 (254 mg, 0.66 mmol) in ethanol (5 mL) and DCM (2 mL) was added sodium borohydride (25 mg, 0.66 mmol). The reaction mixture was stirred at r.t. for 15 minutes. Saturated aqueous ammonium chloride solution and DCM were added to the reaction mixture. The organic layer was separated by passing through a phase separator, then concentrated, to afford the title compound (183 mg, 71%) as a white solid which was used without further purification. The material could be further purified by preparative HPLC. $\delta_H$ (400 MHz, DMSO-d$_6$) 8.93 (d, J 1.2 Hz, 1H), 8.85 (d, J 1.2 Hz, 1H), 8.24 (s, 1H), 8.05 (s, 1H), 7.99 (s, 1H), 7.48 (d, J 1.3 Hz, 2H), 6.61 (d, J 3.5 Hz, 1H), 6.48 (s, 1H), 3.90 (s, 3H), 1.97 (s, 3H). HPLC-MS: MH+ m/z 388.6, RT 1.99 minutes.

Intermediate 42

Ethyl 3-azabicyclo[4.1.0]heptane-6-carboxylate hydrochloride

A 4M solution of HCl in 1,4-dioxane (2.07 mL, 8 mmol) was added to a solution of 3-(tert-butyl) 6-ethyl 3-azabicyclo[4.1.0]heptane-3,6-dicarboxylate (1 g, 4 mmol) in ethanol (10 mL) at r.t. The mixture was stirred at r.t. for 2.5 h. An additional aliquot of ethanol (10 mL) and a 4M solution of HCl in 1,4-dioxane (4.14 mL, 16 mmol) were added, and the mixture was heated at 50° C. for 1.5 h. The reaction mixture was cooled and evaporated under vacuum. A second reaction batch was prepared whereby a 4M solution of HCl in dioxane (10.4 mL, 4 mmol) was added to a solution of 3-(tert-butyl) 6-ethyl 3-azabicyclo[4.1.0]heptane-3,6-dicarboxylate (1 g, 4 mmol) in ethanol (40 mL) and the reaction mixture was warmed to 75° C., then stirred at this temperature overnight. The reaction mixture was cooled to r.t., then concentrated under vacuum in combination with the first batch, to afford the title compound (3.1 g) as a pale yellow solid. $\delta_H$ (250 MHz, DMSO-$d_6$) 9.07 (d, J 37.9 Hz, 2H), 4.05 (q, J 7.1 Hz, 2H), 3.08 (d, J 13.1 Hz, 1H), 2.83 (s, 2H), 2.61 (dt, J 13.7, 6.5 Hz, 1H), 2.00-1.81 (m, 1H), 1.71 (q, J 7.0 Hz, 1H), 1.36-1.22 (m, 2H), 1.18 (q, J 7.1, 6.4 Hz, 3H).

Intermediate 43

Ethyl 3-[5-(3-{[2-(difluoromethoxy)phenyl]methyl}-2-methylimidazo[1,2-a]pyrazin-6-yl)pyrimidin-2-yl]-3-azabicyclo[4.1.0]heptane-6-carboxylate (2-Chloropyrimidin-5-yl)boronic acid (231 mg, 1.46 mmol) and Intermediate 42 (300 mg, 1.46 mmol) were dissolved in DMF (5 mL) and potassium carbonate (302 mg, 2.19 mmol) was added. The mixture was heated at 80° C. in a sealed tube for 3.5 h. The reaction mixture was cooled down to r.t., then Intermediate 6 (347 mg, 0.94 mmol), a 2M solution of potassium carbonate in water (1.39 mL) and 1,4-dioxane (6 mL) were added. The mixture was degassed with nitrogen, then Pd(dppf)Cl$_2$.DCM (39 mg, 0.048 mmol) was added. The mixture was heated at 80° C. in a sealed tube for 3 h. The reaction mixture was cooled down to r.t. and concentrated under vacuum. The resulting brown residue was partitioned between EtOAc (5 mL) and water (3 mL). The organic phase was washed with water (3×3 mL), then the aqueous washes were combined and extracted with EtOAc (3×3 mL). The organic extracts were combined, dried over sodium sulfate, filtered and evaporated. The resulting crude brown oil was purified by FCC (SiO$_2$, heptanes:EtOAc 7.5:2.5 to 2:8) to afford a solid which was further purified by trituration in diethyl ether, then dissolved in a mixture of DMSO and water. The solid which precipitated out of solution was filtered and washed with diethyl ether, to afford the title compound (55 mg, 11%). Method C HPLC-MS: MH+ m/z 535, RT 1.46 minutes.

Intermediate 44

Ethyl 4-[5-(3-{[2-(difluoromethoxy)phenyl]methyl}-2-methylimidazo[1,2-a]pyrazin-6-yl)pyrimidin-2-yl]cyclohex-3-ene-1-carboxylate A mixture of Intermediate 6 (0.3 g, 0.815 mmol), ethyl 4-[5-(4,4,5,5-tetramethyl-1,3,2-dioxaborolan-2-yl)pyrimidin-2-yl]cyclohex-3-ene-1-carboxylate (0.38 g, 1.0 mmol), and a 2M solution of potassium carbonate in water (1.22 mL, 2.0 mmol), in DMF (5 mL) and 1,4-dioxane (5 mL), was degassed by bubbling nitrogen through the mixture for 30 minutes. Pd(dppf)Cl$_2$ complex with dichloromethane (0.03 g, 0.04 mmol) was added and the mixture was heated at 80° C. in a pressure tube for 4 h. The mixture was cooled and stored in a freezer for 7 days. The reaction mixture was diluted with EtOAc (20 mL), then washed with water (3×10 mL). The aqueous washes were combined and extracted with EtOAc (10 mL). The organic extracts were combined, dried over sodium sulfate, filtered and concentrated under vacuum. The resulting crude residue was purified by FCC (heptane:EtOAc 7.5:2.5 to 2.5:7.5) to afford the title compound (339 mg, 80%) as an off-white solid. $\delta_H$ (500 MHz, CDCl$_3$) 9.14 (d, J 6.9 Hz, 3H), 8.17 (s, 1H), 7.38 (s, 1H), 7.36-7.30 (m, 1H), 7.23-7.13 (m, 2H), 7.01 (d, J 7.5 Hz, 1H), 6.66 (t, J 73.5 Hz, 1H), 4.38 (s, 2H), 4.20 (qd, J 7.1, 1.6 Hz, 2H), 2.92 (d, J 17.0 Hz, 1H), 2.72-2.51 (m, 7H), 2.33-2.22 (m, 1H), 1.94-1.83 (m, 1H), 1.31 (t, J 7.1 Hz, 3H). Method B HPLC-MS: MH+ m/z 520, RT 2.27 minutes.

Intermediate 45

Ethyl 4-[5-(3-{[2-(difluoromethoxy)phenyl]methyl}-2-methylimidazo[1,2-a]pyrazin-6-yl)pyrimidin-2-yl]cyclohexane-1-carboxylate Intermediate 44 (165 mg, 0.32 mmol) was dissolved in ethanol (5 mL), then EtOAc (5 mL) and triethylamine (0.047 mL, 0.349 mmol) were added. Palladium on carbon (10% w/w, 67.6 mg, 0.063 mmol) was added. The reaction mixture was flushed with nitrogen (3 times) and hydrogen (3 times), then stirred successively under hydrogen for 6 h and 50 minutes, under nitrogen for 2 days, under hydrogen for 6 h, under nitrogen overnight, and under hydrogen for 3 h. The reaction mixture was filtered through Kieselguhr and washed through with EtOAc, then the filtrate was concentrated. The resulting yellow gum was purified by column chromatography (SiO$_2$, 0-3% MeOH in DCM), to afford the title compound (158 mg, 98%) as a mixture of cis:trans isomers (65:35) as a yellow/orange gum. Method D HPLC-MS: MH+ m/z 522, RT 3.78 and 3.73 minutes.

Intermediate 46

4-(3-{[2-(Difluoromethoxy)phenyl]methyl}-2-methylimidazo[1,2-a]pyrazin-6-yl)-1,2,3,6-tetrahydropyridine hydrochloride Example 8 (700 mg, 1.49 mmol) was suspended in 4M HCl in 1,4-dioxane (3.72 mL) and stirred at room temperature for 2 h. The mixture was concentrated under reduced pressure and dried under vacuum to afford the title compound (600 mg, 99%) as an off-white solid. Method B HPLC-MS: MH+ m/z 371, RT 1.29 minutes.

Intermediate 47

3-(3-{[2-(Difluoromethoxy)phenyl]methyl}-2-methylimidazo[1,2-a]pyrazin-6-yl)-8-azabicyclo[3.2.1]oct-2-ene hydrochloride Example 13 (270 mg, 0.54 mmol) was dissolved in a 4M solution of hydrogen chloride in 1,4-dioxane (2 mL, 8.15 mmol). The reaction mixture was stirred at room temperature for 3 h. The reaction mixture was concentrated under vacuum to afford the title compound (220 mg, 75%) as a yellow powder. Method B HPLC-MS: MH+ m/z 397, RT 0.89 minutes.

Example 1

5-[3-(2,5-Dichlorobenzyl)-2-methylimidazo[1,2-a]pyrazin-6-yl]-1H-pyridin-2-one

Intermediate 10 (189 mg, 0.47 mmol) was dissolved in acetic acid (2 mL). Iodine (119 mg, 0.47 mmol) and phosphinic acid (0.1 mL) were added. The reaction mixture was heated at 100° C. for 2 h. The reaction mixture was quenched with 2M aqueous NaOH solution (5 mL) and partitioned with DCM. The organic layer was extracted, dried over MgSO₄ and concentrated in vacuo. The residue was purified by preparative HPLC, yielding the title compound (6 mg, 3%) as a white solid. $\delta_H$ (d₆-DMSO) 11.83 (s, 1H), 8.96 (d, J 1.1 Hz, 1H), 8.78 (d, J 1.0 Hz, 1H), 8.14 (dd, J 9.6, 2.7 Hz, 1H), 8.08 (m, 1H), 7.55 (m, 1H), 7.39 (dd, J 8.6, 2.5 Hz, 1H), 7.05 (d, J 2.4 Hz, 1H), 6.48 (d, J 9.5 Hz, 1H), 4.50 (s, 2H), 2.24 (s, 3H). LCMS (ES+) 386.0 (M+H)⁺.

Example 2

[2-(Difluoromethoxy)phenyl][6-(6-methoxypyridin-3-yl)-2-methylimidazo[1,2-a]pyrazin-3-yl]methanol Intermediate 13 (0.18 g, 0.44 mmol) and sodium borohydride (0.016 g, 0.44 mmol) were dissolved in ethanol (5 mL) and stirred at room temperature for 1 h. 2M aqueous NaOH solution (5 mL) was added to the reaction mixture, and the mixture was extracted with DCM (20 mL). The organic layers were separated, dried over MgSO₄, and concentrated in vacuo. The residue was triturated with DCM, and the precipitate was filtered off, washing with DCM/MeOH, and dried in vacuo, yielding the title compound (0.100 g, 55%) as a white solid. $\delta_H$ (d₆-DMSO) 9.01 (d, J 1.3 Hz, 1H), 8.88 (d, J 1.4 Hz, 1H), 8.76 (d, J 2.1 Hz, 1H), 8.28 (dd, J 8.7, 2.5 Hz, 1H), 8.05 (dd, J 5.7, 3.8 Hz, 1H), 7.40 (dd, J 5.9, 3.4 Hz, 2H), 7.13 (dd, J 5.7, 3.6 Hz, 1H), 7.08 (s, 1H), 6.97 (m, 1H), 6.57 (d, J 4.2 Hz, 1H), 6.34 (d, J 4.2 Hz, 1H), 3.93 (s, 3H), 2.22 (s, 3H). LCMS (ES+) 413.0 (M+H)'.

Example 3

5-{3-[2-(Difluoromethoxy)benzyl]-2-methylimidazo[1,2-a]pyrazin-6-yl}-2-methoxy-pyridine Intermediate 6 (100 mg, 0.272 mmol) and 6-methoxypyridin-3-ylboronic acid (62 mg, 0.41 mmol) were dissolved in 1,4-dioxane (7 mL), and a 2M solution of potassium carbonate in water (0.5 mL) was added. The reaction mixture was degassed with nitrogen for 5 minutes, then bis[3-(diphenylphosphanyl)cyclopenta-2,4-dien-1-yl]iron; dichloromethane; dichloropalladium (11 mg, 0.014 mmol) was added. The mixture was heated at 90° C. in a sealed tube for 5 h. The mixture was diluted with EtOAc (20 mL) and water (15 mL), then the organic layer was dried over magnesium sulfate and concentrated under vacuum. The crude product was purified by column chromatography, eluting with EtOAc in heptanes (0-100%), to yield the title compound (44 mg, 40%) as an off-white solid. $\delta_H$ (250 MHz, CDCl₃) 9.04 (d, J 1.3 Hz, 1H), 8.60-8.43 (m, 1H), 8.12-7.92 (m, 2H), 7.29-7.20 (m, 1H), 7.15-7.01 (m, 2H), 6.92-6.84 (m, 1H), 6.77 (dd, J 8.7, 0.7 Hz, 1H), 6.58 (t, J 29.4 Hz, 1H), 4.27 (s, 2H), 3.91 (s, 3H), 2.52 (s, 3H). Method C HPLC-MS: MH+ m/z 397, RT 1.24 minutes.

Example 4

5-{3-[2-(Difluoromethoxy)benzyl]-2-methylimidazo[1,2-a]pyrazin-6-yl}-2-(piperazin-1-yl)pyrimidine Intermediate 14 (93%, 81 mg, 136 µmol) was dissolved in DCM (0.2 mL). TFA (0.2 mL) was added and the reaction mixture was stirred at ambient temperature for 30 minutes. The reaction mixture was concentrated under vacuum. The crude product was loaded onto an SCX-2 cartridge and washed with MeOH. The product was then eluted with 7M ammonia in MeOH and concentrated under vacuum. The crude product was purified by column chromatography, eluting with DCM: (7M ammonia in MeOH) 1:0 to 95:5, to afford the title compound (46 mg, 73%) as a pale pink solid. $\delta_H$ (250 MHz, CDCl₃) 8.93 (s, 1H), 8.67 (s, 2H), 7.84 (d, J 1.3 Hz, 1H), 7.19 (m, 1H), 7.06 (m, 2H), 6.85 (m, 1H), 6.57 (t, J 29 Hz, 1H), 4.25 (s, 2H), 3.81 (m, 4H), 2.89 (m, 4H), 2.49 (s, 3H). Method A HPLC-MS: MH+ m/z 452, RT 2.98 minutes.

Example 5

5-{3-[2-(Difluoromethoxy)benzyl]-2-methylimidazo[1,2-a]pyrazin-6-yl}pyridin-2(1H)-one Example 3 (44 mg, 0.06 mmol) was dissolved in 1,4-dioxane (1 mL) and 6M HCl in water (0.18 mL) was added. The mixture was heated under reflux at 70° C. for 9 h. The mixture was diluted with EtOAc (10 mL) and neutralised with 1M aqueous NaOH solution. Water (10 mL) was added, the organic layer was separated and the aqueous layer was extracted with EtOAc (3×10 mL). The organic layers were combined, dried over magnesium sulfate and concentrated under reduced pressure. The crude product was purified by column chromatography, eluting with 0-10% MeOH in DCM, to afford an off-white solid. This material was suspended in minimal DCM and filtered to yield the title compound (15 mg, 35%) as a white solid. Method A HPLC-MS: MH+ m/z 383, RT 3.37 minutes.

Example 6

4-(5-{3-[2-(Difluoromethoxy)benzyl]-2-methylimidazo[1,2-a]pyrazin-6-yl}pyrimidin-2-yl)piperazin-2-one A solution of Intermediate 6 (256 mg, 0.69 mmol) and Intermediate 15 (386 mg, 1.04 mmol) in 2M aqueous K₂CO₃ solution (1.1 mL) and 1,4-dioxane (7 mL) was degassed under nitrogen. Pd(dppf)Cl₂ complex with DCM (28.4 mg, 0.03 mmol) was added and the mixture was heated at 100° C. for 4 h. The mixture was diluted with water (15 mL) and extracted with 1:1 chloroform/isopropanol (2×20 mL), followed by 1:5 methanol/DCM. The combined organic extracts were dried over sodium sulfate and concentrated under vacuum. The crude product was triturated with methanol (20 mL) and the remaining solids were filtered off, washed with diethyl ether (20 mL) and dried under vacuum, to afford the title compound (186 mg, 57%) as an off-white solid. $\delta_H$ (500 MHz, MeOD) 8.93 (s, 1H), 8.91 (s, 2H), 8.56 (s, 1H), 7.32 (t, J 7.7 Hz, 1H), 7.25-7.15 (m, 3H), 6.91 (t, J 74.0 Hz, 1H), 4.46 (s, 2H), 4.43 (s, 2H), 4.14-4.07 (m, 2H), 3.45 (t, J 5.3 Hz, 2H), 2.46 (s, 3H). HPLC-MS: MH+ m/z 466.

Example 7

1-(5-{3-[2-(Difluoromethoxy)benzyl]-2-methylimidazo[1,2-a]pyrazin-6-yl}pyrimidin-2-yl)-1,4-diazepan-5-one A solution of Intermediate 16 (133 mg, 0.56 mmol) and Intermediate 6 (207 mg, 0.56 mmol) in 1,4-dioxane (4 mL) and DMSO (0.5 mL) was degassed under nitrogen. To this solution was added a nitrogen-degassed 2M aqueous solution of K₂CO₃ (986 µL) followed by Pd(dppf)Cl₂ complex with DCM (23 mg, 0.03 mmol). The reaction mixture was sealed under nitrogen and stirred at 120° C. for 16 h. EtOAc (10 mL) and water (5 mL) were added and the organic phase was separated, then the aqueous layer was further extracted with EtOAc (2×10 mL). The combined organic extracts were washed with water (10 mL) and brine (10 mL), dried over magnesium sulfate and concentrated under vacuum. The crude product was purified by Biotage (SNAP 10 g cartridge), eluting with 0-100% EtOAc in heptanes, followed by 0-10% (7N $NH_3$ in MeOH) in DCM, to afford a brown solid. This material was triturated with MeOH to afford the title compound (47 mg, 18%) as a white precipitate. $\delta_H$ (250 MHz, $CDCl_3$) 9.16 (s, 1H), 8.78 (s, 2H), 8.01 (d, J 1.4 Hz, 1H), 7.30 (m, 1H), 7.15 (m, 2H), 6.96 (d, J 10.5 Hz, 1H), 6.65 (t, J 29 Hz, 1H), 6.04 (s, 1H), 4.34 (s, 2H), 4.12 (m, 4H), 3.39 (d, J 5.5 Hz, 2H), 2.71 (m, 2H), 2.61 (s, 3H). LCMS: MH+480/481.

Example 8 tert-Butyl 4-(3-{[2-(difluoromethoxy)phenyl]methyl}-2-methylimidazo[1,2-d]pyrazin-6-yl)-1,2,3,6-tetrahydropyridine-1-carboxylate A mixture of Intermediate 6 (100 mg, 0.27 mmol), Intermediate 17 (126 mg, 0.41 mmol) and aqueous potassium carbonate solution (2M, 0.54 mL) in 1,4-dioxane (4 mL) was purged with nitrogen for 5 minutes, then bis[3-(diphenylphosphanyl)cyclopenta-2,4-dien-1-yl]iron dichloropalladium dichloromethane complex (11 mg, 0.01 mmol) was added and the mixture was heated at 90° C. for 2 h. The mixture were filtered through celite, concentrated under reduced pressure and purified by preparative HPLC, to afford the title compound (67.4 mg, 53%) as a beige solid. $\delta_H$ (500 MHz, $CDCl_3$) 8.91 (s, 1H), 7.65 (s, 1H), 7.28 (d, J 7.4 Hz, 1H), 7.16 (d, J 8.1 Hz, 1H), 7.10 (t, J 7.5 Hz, 1H), 6.91 (t, J 8.4 Hz, 1H), 6.78-6.43 (m, 2H), 4.27 (s, 2H), 4.16-4.06 (m, 2H), 3.63 (s, 2H), 2.53 (s, 3H), 2.41 (s, 2H), 1.47 (s, 9H). Method D HPLC-MS: MH+ m/z 471, RT 3.52 minutes.

Example 9 tert-Butyl 4-(3-{[2-(difluoromethoxy)phenyl]methyl}-2-methylimidazo[1,2-a]pyrazin-6-yl)piperidine-1-carboxylate Example 8 (900 mg, 1.91 mmol) was dissolved in ethanol (50 mL), then palladium on carbon (10% w/w, 204 mg) was added. The suspension was degassed using vacuum/nitrogen and the reaction mixture was stirred under hydrogen at ambient temperature and pressure for 14 h. The reaction mixture was then degassed using vacuum/nitrogen and filtered through celite, washing with MeOH (15 mL). The solvent was removed under reduced pressure and the residue was purified by FCC, eluting with 10-15% DCM in MeOH, to afford the title compound (571 mg, 63%) as a pale yellow oil. $\delta_H$ (500 MHz, $CDCl_3$) 9.09 (br s, 1H), 7.65 (s, 1H), 7.32 (t, J 7.2 Hz, 1H), 7.15 (t, J 8.8 Hz, 2H), 6.97 (d, J 7.4 Hz, 1H), 6.62 (t, J 73.5 Hz, 1H), 4.28 (s, 4H), 2.83 (s, 2H), 2.60 (s, 3H), 1.92 (d, J 12.3 Hz, 2H), 1.72-1.56 (m, 3H), 1.47 (s, 9H). Method D HPLC-MS: MH+ m/z 474, RT 3.22 minutes.

Example 10

4-(3-{[2-(Difluoromethoxy)phenyl]methyl}-2-methylimidazo[1,2-a]pyrazin-6-yl)-benzene-1-sulfonamide Pd(PPh$_3$)$_4$ (16 mg, 0.01 mmol) was added to a thoroughly degassed mixture of Intermediate 6 (50 mg, 0.14 mmol) and (4-sulfamoylphenyl)boronic acid (41 mg, 0.2 mmol) in 2M aqueous sodium carbonate solution (0.44 mL) and 1,2-dimethoxyethane (2.2 mL). The mixture was heated in a sealed tube at 90° C. under nitrogen for 2 h. Further (4-sulfamoylphenyl)boronic acid (41 mg, 0.2 mmol) and 2M aqueous sodium carbonate solution (0.44 mL) were added and the mixture was heated at 90° C. for a further 2 h. The reaction mixture was cooled, diluted with DCM (10 mL), and washed with saturated aqueous sodium hydrogencarbonate solution (10 mL) followed by brine, then dried over sodium sulfate and concentrated under vacuum. The crude residue was triturated with a minimum of chloroform, to afford the title compound (12 mg, 19%) as a pale yellow solid. $\delta_H$ (500 MHz, DMSO-$d_6$) 9.06-9.00 (m, 2H), 8.28-8.22 (m, 2H), 7.95-7.89 (m, 2H), 7.48-7.10 (m, 7H), 4.48 (s, 2H), 2.34 (s, 3H). Method D HPLC-MS: MH+ m/z 445, RT 2.59 minutes.

Example 11

4-[5-(3-{[2-(Difluoromethoxy)phenyl]methyl}-2-methylimidazo[1,2-a]pyrazin-6-yl)-pyridin-2-yl]morpholine Intermediate 18 (90% pure, 92.6 mg, 0.21 mmol) and morpholine (60 mg, 0.69 mmol) were stirred in 1-methyl-2-pyrrolidinone (2 mL) in a microwave tube. The reaction mixture was heated to 200° C. under microwave irradiation for a total of 2.5 h. The mixture was loaded onto an SCX cartridge, which was washed with MeOH followed by 7M ammonia in MeOH. The ammonia fractions were concentrated under vacuum and purified by FCC, eluting with 0-10% (7M ammonia in MeOH) in DCM. The crude material was further purified by FCC, eluting with 50-100% EtOAc in heptanes, to afford the title compound (29.6 mg, 30%) as an off-white solid. $\delta_H$ (250 MHz, $CDCl_3$) 9.02 (d, J 1.4 Hz, 1H), 8.57 (d, J 2.0 Hz, 1H), 8.06 (dd, J 8.9, 2.5 Hz, 1H), 7.98 (d, J 1.4 Hz, 1H), 7.32-7.24 (m, 1H), 7.20-7.06 (m, 2H), 6.95-6.34 (m, 3H), 4.32 (s, 2H), 3.86-3.81 (m, 4H), 3.61-3.55 (m, 4H), 2.56 (s, 3H). Method A HPLC-MS: MH+ m/z 452, RT 3.43 minutes.

Example 12

5-(3-{[2-(Difluoromethoxy)phenyl]methyl}-2-methylimidazo[1,2-a]pyrazin-6-yl)-2-[4-(methanesulfonyl)piperazin-1-yl]pyrimidine A mixture of (2-chloropyrimidin-5-yl)boronic acid (100 mg, 0.63 mmol) and 1-(methylsulfonyl)piperazine (311 mg, 1.89 mmol) was heated under microwave irradiation at 100° C. for 1 h. Intermediate 6 (153 mg, 0.42 mmol), 2M aqueous sodium carbonate solution (1.52 mL) and 1,2-dimethoxyethane (4 mL) were added. The mixture was thoroughly degassed with nitrogen, then Pd(PPh$_3$)$_4$ (73 mg, 0.06 mmol) was added. The mixture was heated at 90° C. in a sealed tube under a nitrogen atmosphere for 2 h, then cooled and diluted with DCM (20 mL) and saturated aqueous sodium bicarbonate solution (10 mL). The organic phase was washed with brine, dried over sodium sulfate and concentrated under vacuum. The crude product was triturated with 1:9 DMSO/acetonitrile (20 mL) and filtered. The solid residue was washed with acetonitrile (10 mL) to afford the title compound (76 mg, 21%) as a white solid. $\delta_H$ (250 MHz, $CDCl_3$) 9.06 (d, J 1.2 Hz, 1H), 8.76 (s, 2H), 7.99 (d, J 1.4 Hz, 1H), 7.35-7.25 (m, 1H), 7.20-7.07 (m, 2H), 6.99-6.32 (m, 2H), 4.32 (s, 2H), 4.09-3.95 (m, 4H), 3.35-3.22 (m, 4H), 2.79 (s, 3H), 2.57 (s, 3H). Method D HPLC-MS: MH+ m/z 530, RT 2.91 minutes.

Example 13 tert-Butyl 3-(3-{[2-(difluoromethoxy)phenyl]methyl}-2-methylimidazo[1,2-a]pyrazin-6-yl)-8-azabicyclo[3.2.1]oct-2-ene-8-carboxylate Intermediate 6 (50 mg, 0.136 mmol), Intermediate 19 (68 mg, 0.20 mmol) and 2M aqueous sodium carbonate solution (0.43 mL) were combined in 1,2-dimethoxyethane (2.2 mL) and degassed thoroughly under nitrogen. Pd(PPh$_3$)$_4$ (16 mg, 0.01 mol) was added and the mixture was heated at 90° C. in a sealed tube for 2 h. The reaction mixture was cooled to r.t., then diluted with DCM (10 mL). The mixture was washed using saturated aqueous sodium bicarbonate solution (2×5 mL) and brine (10 mL). The organic phase was dried over sodium sulfate and concentrated under vacuum. The crude residue was purified by FCC, eluting with a gradient of 0-100% EtOAc in heptanes. The material was further purified by preparative HPLC, to afford the title compound (14.4 mg, 21%) as a white solid. $\delta_H$ (500 MHz, CDCl$_3$) 8.94 (s, 1H), 7.61 (s, 1H), 7.28 (dd, J 13.0, 5.5 Hz, 1H), 7.16 (d, J 8.1 Hz, 1H), 7.11 (t, J 7.5 Hz, 1H), 6.91 (d, J 7.6 Hz, 1H), 6.63 (t, J 73.5 Hz, 1H), 4.55 (s, 2H), 4.27 (s, 2H), 3.00 (s, 1H), 2.54 (s, 3H), 2.15 (d, J 48.4 Hz, 2H), 2.08-1.92 (m, 3H), 1.66-1.61 (m, 1H), 1.42 (s, 9H). Method A HPLC-MS: MH+ m/z 497, RT 4.64 minutes.

Example 14

2-{4-[5-(3-{[2-(Difluoromethoxy)phenyl]methyl}-2-methylimidazo[1,2-a]pyrazin-6-yl)-pyrimidin-2-yl]piperazin-1-yl}acetic acid, formate salt Intermediate 20 (118 mg, 0.23 mmol) was suspended in THF (2 mL) and 4M aqueous sodium hydroxide solution (59 µL) was added. The reaction mixture was stirred for 1 h. MeOH (1 mL) was added and the mixture was heated gently with a heat gun until a solution was obtained. The resulting mixture was stirred for 45 minutes. Further 4M aqueous sodium hydroxide solution (30 µL) was added, and the reaction mixture was heated at 50° C. for 1 h. Further 4M aqueous sodium hydroxide solution (30 µL) was added, and the reaction mixture was heated at 50° C. for 30 minutes, then maintained at r.t. overnight. The reaction mixture was neutralised with 4M HCl to pH ~6 and was concentrated to dryness. The residue was dissolved in MeOH and loaded onto a SAX column. The column was flushed with MeOH, then a 1:9 mixture of 1M aqueous HCl/MeOH. All fractions contained product and impurities, so all of the material was recombined and concentrated to dryness. The residue was purified by preparative HPLC to yield the title compound (23.4 mg, 19%). $\delta_H$ (500 MHz, DMSO-d$_6$) 8.98 (s, 1H), 8.96 (s, 2H), 8.79 (s, 1H), 7.42-7.06 (m, 5H), 4.42 (s, 2H), 3.88-3.81 (m, 4H), 3.26 (s, 2H), 2.72-2.63 (m, 4H), 2.33 (s, 3H). Method D HPLC-MS: MH+ m/z 509, RT 1.91 minutes.

Example 15

2-{4-[5-(3-{[2-(Difluoromethoxy)phenyl]methyl}-2-methylimidazo[1,2-a]pyrazin-6-yl)-pyrimidin-2-yl]piperazin-1-yl}acetamide The hydrochloride salt of Example 4 (126 mg, 0.26 mmol) was dissolved in DMF (3 mL), then caesium carbonate (252 mg, 0.77 mmol) and 2-bromoacetamide (37 mg, 0.27 mmol) were added, and the reaction mixture was stirred for a total of 20 h. The reaction mixture was concentrated to dryness and triturated with water (3 mL), to afford the title compound (111.6 mg, 85%) as an off-white solid. $\delta_H$ (500 MHz, DMSO-d$_6$) 8.98 (s, 1H), 8.95 (s, 2H), 8.79 (s, 1H), 7.42-7.12 (m, 7H), 4.42 (s, 2H), 3.90-3.80 (m, 4H), 2.92 (s, 2H), 2.55-2.50 (m, 4H), 2.33 (s, 3H). Method D HPLC-MS: MH+ m/z 508, RT 1.68 minutes.

Example 16

[2-(Difluoromethoxy)phenyl]{2-methyl-6-[6-(piperazin-1-yl)pyridin-3-yl]imidazo[1,2-a]-pyrazin-3-yl}methanol Intermediate 21 (117 mg, 0.207 mmol) was dissolved in a mixture of DCM (5 mL) and trifluoroacetic acid (1 mL) and stirred at r.t. overnight. The reaction mixture was concentrated under vacuum, redissolved in DCM (20 mL), washed with saturated aqueous sodium bicarbonate solution (2×10 mL) followed by brine (10 mL), then dried over sodium sulfate and concentrated under vacuum. The residue was purified by FCC, eluting with a gradient of 0-2.5% (7M NH$_3$ in MeOH) in DCM. The resulting material was further purified by preparative HPLC. The product fractions were combined and extracted with DCM (4×10 mL). The organic layer was washed with brine (10 mL), dried over sodium sulfate and concentrated under vacuum, to afford the title compound (50 mg, 52%) as a white solid. $\delta_H$ (250 MHz, CDCl$_3$) 8.85 (d, J 1.1 Hz, 1H), 8.66 (dd, J 4.1, 1.9 Hz, 2H), 8.15 (m, 1H), 8.05 (dd, J 8.9, 2.4 Hz, 1H), 7.40 (m, 2H), 7.16 (d, J 8.6 Hz, 1H), 6.80 (m, 3H), 3.54 (m, 4H), 2.87 (m, 4H), 2.34 (s, 3H). Method D HPLC-MS: MH+ m/z 467, RT 1.43 minutes.

Example 17

5-(3-{[2-(Difluoromethoxy)phenyl]methyl}-2-methylimidazo[1,2-a]pyrazin-6-yl)-N-(oxolan-3-yl)pyrimidin-2-amine (2-Chloropyrimidin-5-yl)boronic acid (50 mg, 0.32 mmol) was dissolved in 1,4-dioxane (1 mL) and tetrahydrofuran-3-amine hydrochloride (117 mg, 0.95 mmol) was added, followed by sodium carbonate (117.13 mg, 1.11 mmol). The reaction mixture was heated at 100° C. under microwave irradiation for 1 h. The reaction mixture was transferred to a pressure tube and diluted with 1,2-dimethoxyethane (2 mL). Intermediate 6 (58 mg, 0.16 mmol) was added, followed by 2M aqueous sodium carbonate solution (0.76 mL), and the reaction mixture was degassed with nitrogen for 5 minutes. Pd(PPh$_3$)$_4$ (36 mg, 0.03 mmol) was added, and the mixture was heated at 90° C. for 2 h. The reaction mixture was diluted with EtOAc (15 mL), washed with water (10 mL) and brine (10 mL), then dried over sodium sulfate and concentrated to dryness. The residue was purified by preparative HPLC, to afford the title compound (22 mg, 15%) as a white solid. $\delta_H$ (500 MHz, CD$_3$OD) 8.91 (s, 1H), 8.80 (d, J 4.1 Hz, 2H), 8.50 (s, 1H), 7.32 (t, J 7.7 Hz, 1H), 7.24-7.14 (m, 3H), 6.91 (t, J 73.9 Hz, 1H), 4.60-4.52 (m, 1H), 4.45 (s, 2H), 4.03-3.94 (m, 2H), 3.90-3.82 (m, 1H), 3.72 (dd, J 9.1, 3.7 Hz, 1H), 2.45 (s, 3H), 2.35-2.27 (m, 1H), 1.98 (m, J 4.9 Hz, 1H). Method D HPLC-MS: MH+ m/z 453, RT 2.51 minutes.

Example 18

5-(3-{[2-(Difluoromethoxy)phenyl]methyl}-2-methylimidazo[1,2-a]pyrazin-6-yl)-2-(4,4-difluoropiperidin-1-yl)pyrimidine (2-Chloropyrimidin-5-yl)boronic acid (200 mg, 1.26 mmol) and 4,4-difluoro-piperidine hydrochloride (239 mg, 1.52 mmol) were suspended in 1,4-dioxane (3 mL) and heated for 1 h at 100° C. under microwave irradiation. The mixture was filtered and concentrated under vacuum. Intermediate 6 (200 mg, 0.54 mmol) and 1,4-dioxane (4 mL) were added, and the mixture was degassed for 5 minutes. Degassed 2M aqueous potassium carbonate solution (0.81 mL) and bis[3-(diphenylphosphanyl)cyclopenta-2,4-dien-1-yl]iron dichloropalladium dichloromethane complex (31 mg, 0.04 mmol) were added and the mixture was heated at 100° C. for 16 h. The mixture was partitioned between EtOAc (30 mL) and water (20 mL) and the aqueous phase was extracted with further EtOAc (20 mL). The organic layers were combined and washed with brine, dried over magnesium sulfate and concentrated under vacuum. The residue was purified by FCC, eluting with a gradient of 0-5% ammonia/MeOH in DCM. The material was then triturated in hot MeOH, and the solids were filtered, to afford the title compound (124 mg, 47%) as a pale peach solid. $\delta_H$ (250 MHz, CDCl$_3$) 9.16 (s, 1H), 8.78 (s, 2H), 8.00 (s, 1H), 7.30 (d, J 8.4 Hz, 1H), 7.16 (dd, J 12.3, 7.4 Hz, 2H), 7.01-6.34 (m, 2H), 4.34 (s, 2H), 4.10-3.99 (m, 4H), 2.62 (s, 3H), 2.03 (tt, J 13.6, 5.8 Hz, 4H). Method A HPLC-MS: MH+ m/z 487, RT 4.55 minutes.

Example 19

6-[5-(3-{[2-(Difluoromethoxy)phenyl]methyl}-2-methylimidazo[1,2-a]pyrazin-6-yl)-pyrimidin-2-yl]-2-oxa-6-azaspiro[3.3]heptane (2-Chloropyrimidin-5-yl)boronic acid (150 mg, 0.95 mmol) and 2-oxa-6-azaspiro-[3.3]heptane oxalate (239 mg, 1.26 mmol) were suspended in 1,4-dioxane (6 mL) and triethylamine (0.18 mL, 1.26 mmol) was added. The mixture was heated at 100° C. under microwave irradiation for 1 h. The mixture was diluted with MeOH (20 mL), then concentrated. To the resulting orange oil were added Intermediate 6 (228 mg, 0.62 mmol), 2M aqueous potassium carbonate solution (1.4 mL) and 1,4-dioxane (5 mL). The mixture was thoroughly degassed before the addition of bis[3-(diphenylphosphanyl)-cyclopenta-2,4-dien-1-yl]iron dichloropalladium dichloromethane complex (36 mg, 0.04 mmol), then the mixture was heated at 100° C. for 15 h. EtOAc (10 mL) was added, then the mixture was washed with water (2×10 mL) and brine (10 mL). The organic layer was dried over sodium sulfate and concentrated under vacuum. The crude residue was purified by FCC, eluting with a gradient of 0-7% MeOH in DCM. The resulting material was further purified by preparative HPLC, to afford the title compound (21.2 mg, 5%) as a white solid. $\delta_H$ (500 MHz, CDCl$_3$) 9.04 (d, J 4.5 Hz, 1H), 8.74 (s, 2H), 7.93 (s, 1H), 7.28 (t, J 7.9 Hz, 1H), 7.17 (d, J 8.2 Hz, 1H), 7.12 (t, J 7.5 Hz, 1H), 6.94 (d, J 7.6 Hz, 1H), 6.63 (t, J 73.5 Hz, 1H), 4.87 (s, 4H), 4.35 (s, 4H), 4.32 (s, 2H), 2.57 (s, 3H). Method A HPLC-MS: MH+ m/z 465, RT 3.59 minutes.

Example 20

4-[5-(3-{[2-(Difluoromethoxy)phenyl]methyl}-2-methylimidazo[1,2-a]pyrazin-6-yl)-pyrimidin-2-yl]-2,6-dimethylmorpholine (2-Chloropyrimidin-5-yl)boronic acid (50 mg, 0.32 mmol) was dissolved in 1,4-dioxane (1 mL) and 2,6-dimethylmorpholine (117 µL, 0.95 mmol) was added. The reaction mixture was heated at 100° C. under microwave irradiation for 1 h. The reaction mixture was transferred to a pressure tube and diluted with 1,2-dimethoxyethane (2 mL). Intermediate 6 (77 mg, 0.21 mmol) was added, followed by 2M aqueous sodium carbonate solution (0.76 mL), and the reaction was degassed with nitrogen for 5 minutes. Pd(PPh$_3$)$_4$ (36 mg, 0.03 mmol) was added and the mixture was heated at 90° C. for 100 minutes. The reaction mixture was diluted with EtOAc (15 mL) and washed with water (10 mL), followed by brine (10 mL), then dried over sodium sulfate and concentrated to dryness. The residue was purified by preparative HPLC to afford the title compound (17.6 mg, 12%) as a white solid. $\delta_H$ (500 MHz, CD$_3$OD) 8.90 (d, J 1.3 Hz, 1H), 8.83 (s, 2H), 8.50 (d, J 1.3 Hz, 1H), 7.36-7.28 (m, 1H), 7.24-7.14 (m, 3H), 6.91 (t, J 74.0 Hz, 1H), 4.64 (d, J 11.8 Hz, 2H), 4.45 (s, 2H), 3.71-3.58 (m, 2H), 2.62 (dd, J 13.3, 10.6 Hz, 2H), 2.45 (s, 3H), 1.24 (d, J 6.1 Hz, 6H). Method D HPLC-MS: MH+ m/z 481, RT 3.42 minutes.

Example 21

1-[5-(3-{[2-(Difluoromethoxy)phenyl]methyl}-2-methylimidazo[1,2-a]pyrazin-6-yl)-pyrimidin-2-yl] piperidine-4-carboxylic acid Intermediate 6 (120 mg, 0.326 mmol) and Intermediate 22 (164 mg, 0.424 mmol) were charged to a sealed tube with 1,4-dioxane (1 mL) and 1,2-dimethoxyethane (1 mL), and the mixture was degassed. Aqueous sodium carbonate solution (2M, 0.815 mL, 1.63 mmol) and Pd(PPh$_3$)$_4$ (19 mg, 0.016 mmol) were added, and the mixture was stirred at 90° C. under nitrogen for 3 h. Further Intermediate 22 (164 mg, 0.424 mmol) and 2M aqueous sodium carbonate solution (0.815 mL, 1.63 mmol) were added, the mixture was degassed, and Pd(PPh$_3$)$_4$ (19 mg, 0.016 mmol) was added. The mixture was then stirred at 90° C. under nitrogen for 4 h. The mixture was diluted with water (10 mL) and DCM (10 mL). The organic phase was separated and the aqueous phase was extracted with DCM (2×5 mL), then the combined organic layers were discarded. The aqueous layer was adjusted to pH 1 by the addition of 0.5N HCl (10 mL). The resultant white suspension was filtered, and the filter pad was washed with water (2×4 mL) and MeOH (4 mL). The resulting solid was suspended in MeOH (20 mL) and heated to reflux, then allowed to cool to r.t. before being filtered, to afford the title compound (50 mg, 31%) as a white solid. $\delta_H$ (500 MHz, CD$_3$OD) 8.90 (s, 1H), 8.81 (s, 2H), 8.48 (s, 1H), 7.35-7.28 (m, 1H), 7.23-7.14 (m, 3H), 6.89 (t, J 74.0 Hz, 1H), 4.68 (d, J 13.5 Hz, 2H), 4.44 (s, 2H), 3.19-3.09 (m, 2H), 2.63 (tt, J 10.9, 3.9 Hz, 1H), 2.44 (s, 3H), 2.04-1.93 (m, 2H), 1.71-1.56 (m, 2H). Method D HPLC-MS: MH+ m/z 495, RT 2.73 minutes.

Example 22

(1R,5S,6r)-3-(5-{3-[2-(Difluoromethoxy)benzyl]-2-methylimidazo[1,2-a]pyrazin-6-yl}-pyrimidin-2-yl)-3-azabicyclo[3.1.0]hexane-6-carboxylic acid Intermediate 25 (100 mg, 0.19 mmol) was dissolved in THF (2 mL), then 2M aqueous NaOH solution (0.29 mL)

was added and the mixture was stirred at 50° C. overnight. Further 2M aqueous NaOH solution (0.5 mL) was added and the mixture was heated at 80° C. for 6 h and then overnight. The reaction mixture was concentrated and adjusted to pH 5 using 1M aqueous HCl solution. The aqueous layer was extracted with 1:1 isopropanol/chloroform (2×10 mL), then the organic layer was washed with brine (10 mL), dried over sodium sulfate and concentrated. The resultant solids were suspended in MeCN/MeOH/DMSO and filtered, to afford the title compound (7.7 mg, 8%) as a white solid. $\delta_H$ (500 MHz, DMSO-$d_6$) 12.27 (s, 1H), 8.97 (d, J 1.0 Hz, 1H), 8.92 (s, 2H), 8.76 (s, 1H), 7.41-7.11 (t, J 75.6 Hz, 1H), 7.34-7.28 (m, 1H), 7.17 (dd, J 18.5, 7.6 Hz, 3H), 4.41 (s, 2H), 3.91 (d, J 11.6 Hz, 2H), 3.60 (d, J 10.9 Hz, 2H), 2.33 (s, 3H), 2.18 (d, J 15.4 Hz, 2H), 1.40 (t, J 3.0 Hz, 1H). Method D HPLC-MS: MH+ m/z 493, RT 2.52 minutes.

Example 23

Ethyl 1-[5-(3-{[2-(difluoromethoxy)phenyl]methyl}-2-methylimidazo[1,2-a]pyrazin-6-yl)pyrimidin-2-yl]-4-methylpiperidine-4-carboxylate Intermediate 6 (150 mg, 0.41 mmol) and Intermediate 26 (80% pure, 164.21 mg, 0.45 mmol) were dissolved in 1,4-dioxane (2 mL) and 2M aqueous potassium carbonate solution (713 µL, 1.426 mmol) was added. The reaction mixture was degassed with nitrogen for 5 minutes, then bis[3-(diphenylphosphanyl)cyclopenta-2,4-dien-1-yl]iron dichloropalladium dichloromethane complex (17 mg, 0.02 mmol) was added. The reaction mixture was heated at 90° C. for 18 h in a sealed tube under nitrogen. Further Intermediate 26 (50 mg), 2M aqueous potassium carbonate solution (240 µL) and bis[3-(diphenylphosphanyl)cyclopenta-2,4-dien-1-yl]iron dichloropalladium dichloromethane complex (5 mg) were added and the mixture was heated for a further 2 h. Further Intermediate 26 (50 mg), 2M aqueous potassium carbonate solution (240 µL) and bis[3-(diphenylphosphanyl)cyclopenta-2,4-dien-1-yl]iron dichloropalladium dichloromethane complex (5 mg) were added and the mixture was heated for a further 3 h. The mixture was diluted with water (5 mL) and extracted with EtOAc (3×10 mL). The organic layer was washed with brine (10 mL), dried over magnesium sulfate and concentrated under vacuum. The residue was purified by FCC, eluting with 0-100% EtOAc in heptanes followed by 0-30% MeOH in DCM, to afford the title compound (170 mg, 78%). $\delta_H$ (250 MHz, CDCl$_3$) 9.15 (s, 1H), 8.75 (s, 2H), 7.96 (d, J 1.3 Hz, 1H), 7.33 (d, J 8.7 Hz, 1H), 7.16 (dd, J 13.4, 7.2 Hz, 2H), 6.99-6.35 (m, 2H), 4.42 (d, J 13.9 Hz, 2H), 4.33 (s, 2H), 4.20 (q, J 7.1 Hz, 2H), 3.39-3.27 (m, 2H), 2.61 (s, 3H), 2.20 (d, J 13.6 Hz, 2H), 1.52-1.40 (m, 2H), 1.32-1.25 (m, 6H). Method D HPLC-MS: MH+ m/z 537, RT 3.91 minutes.

Example 24

1-[5-(3-{[2-(Difluoromethoxy)phenyl]methyl}-2-methylimidazo[1,2-a]pyrazin-6-yl)-pyrimidin-2-yl]-4-methylpiperidine-4-carboxylic acid Example 23 (160 mg, 0.30 mmol) was stirred in THF (7 mL), 2M aqueous NaOH solution (1.49 mL) was added and the mixture was heated at 80° C. for 3 h. Lithium hydroxide monohydrate (25 mg, 0.60 mmol) was added and the mixture was heated for a further 1.5 h. The temperature was then increased to 110° C. and the mixture was stirred for 19 h. Further lithium hydroxide monohydrate (25 mg, 0.60 mmol) was added and the mixture was heated at 110° C. for 6.5 h. The reaction mixture was concentrated, dissolved in water (10 mL) and acidified by dropwise addition of 6M HCl until a white precipitate formed at pH 1. The precipitate was filtered and dried, to afford the title compound (112.3 mg, 73%) as a white solid. $\delta_H$ (250 MHz, DMSO-$d_6$) 9.08 (s, 1H), 8.95 (s, 2H), 8.87 (s, 1H), 7.59-6.95 (m, 5H), 4.45 (s, 2H), 4.29 (d, J 13.1 Hz, 2H), 3.33 (t, J 10.8 Hz, 2H), 2.35 (s, 3H), 2.01 (d, J 13.7 Hz, 2H), 1.40 (t, J 9.6 Hz, 2H), 1.18 (s, 3H). Method D HPLC-MS: MH+ m/z 509, RT 2.99 minutes.

Example 25

5-(3-{[2-(Difluoromethoxy)phenyl]methyl}-2-methylimidazo[1,2-a]pyrazin-6-yl)-2-(3-methoxypyrrolidin-1-yl)pyrimidine (2-Chloropyrimidin-5-yl)boronic acid (100 mg, 0.632 mmol) and 3-methoxy-pyrrolidine (64 mg, 0.63 mmol) were suspended in 1,4-dioxane (3 mL), triethylamine (0.09 mL, 0.632 mmol) was added and the mixture was heated at 60° C. under microwave irradiation for 45 minutes. The reaction mixture was concentrated under vacuum, dissolved in DCM (20 mL) and washed with water (2×10 mL). The aqueous layer was concentrated under vacuum. To the resulting off-white solid were added Intermediate 6 (173 mg, 0.47 mmol), 2M aqueous potassium carbonate solution (1.09 mL) and 1,4-dioxane (5 mL). The mixture was thoroughly degassed before the addition of bis[3-(diphenylphosphanyl)cyclopenta-2,4-dien-1-yl]iron dichloropalladium dichloromethane complex (27 mg, 0.034 mmol). The mixture was heated at 100° C. overnight. Pd(PPh$_3$)$_4$ (0.034 mmol) was added and the mixture was heated at 100° C. overnight. EtOAc (10 mL) was added and the mixture was washed with water (2×10 mL) and brine (10 mL). The organic fraction was dried over sodium sulfate and concentrated under vacuum. The crude residue was purified by FCC, eluting with 0-7% MeOH in DCM. The material was then further purified by preparative HPLC to afford the title compound (7.3 mg, 2%) as a yellow solid. $\delta_H$ (500 MHz, CDCl$_3$) 9.06 (s, 1H), 8.76 (s, 2H), 7.91 (s, 1H), 7.29 (t, J 7.8 Hz, 1H), 7.17 (d, J 8.1 Hz, 1H), 7.12 (t, J 7.5 Hz, 1H), 6.93 (d, J 7.7 Hz, 1H), 6.81-6.45 (m, 1H), 4.32 (s, 2H), 4.16-4.05 (m, 1H), 3.85-3.74 (m, 2H), 3.74-3.62 (m, 2H), 3.38 (s, 3H), 2.58 (s, 3H), 2.25-2.16 (m, 1H), 2.10 (m, 1H). Method D HPLC-MS: MH+ m/z 466, RT 2.77 minutes.

Example 26

2-[5-(3-{[2-(Difluoromethoxy)phenyl]methyl}-2-methylimidazo[1,2-a]pyrazin-6-yl)-pyrimidin-2-yl]-2-azaspiro[3.3]heptane-6-carboxylic acid (2-Chloropyrimidin-5-yl)boronic acid (100 mg, 0.63 mmol) and 2-azaspiro[3.3]-heptane-6-carboxylic acid hydrochloride (113 mg, 0.64 mmol) were dissolved in DMF (2 mL), then potassium carbonate (131 mg, 0.95 mmol) was added. The mixture was heated at 80° C. in a sealed tube for 2 h. To the mixture were added Intermediate 6 (150 mg, 0.41 mmol), 2M aqueous potassium carbonate solution (0.6 mL) and 1,4-dioxane (3 mL). The mixture was degassed with nitrogen, then bis[3-(diphenylphosphanyl)cyclopenta-2,4-dien-1-yl]iron dichloropalladium dichloromethane complex (17 mg, 0.02 mmol) was added. The mixture was heated at 80° C. in a sealed tube for 4 h. The mixture was diluted with DCM (20 mL) and extracted with water (10 mL), followed by 2M aqueous potassium carbonate solution (10 mL). The combined aqueous layers were acidified to pH 4 by the addition of 6M hydrochloric acid. The mixture was left to stand for 10 minutes and the resultant precipitate was collected by filtration. The solids were washed with water (5 mL) and DCM (5 mL), and dried under vacuum, to afford the title compound (50.9 mg, 25%) as a pale pink solid. $\delta_H$ (500 MHz, CD$_3$OD) 8.92 (s, 1H), 8.83 (s, 2H), 8.54 (s, 1H), 7.32 (t, J 7.0 Hz, 1H), 7.23-7.15 (m, 3H), 6.90 (t, J 73.9 Hz, 1H), 4.61 (s, 1H), 4.46 (s, 2H), 4.20 (s, 2H), 4.13 (s, 2H), 3.06-3.01 (m, 1H), 2.56-2.47 (m, 4H), 2.45 (s, 3H). Method D HPLC-MS: MH+ m/z 507, RT 2.51 minutes.

Example 27

1-[5-(3-{[2-(Difluoromethoxy)phenyl]methyl}-2-methylimidazo[1,2-a]pyrazin-6-yl)-pyrimidin-2-yl]-4-hydroxypiperidine-4-carboxylic acid Intermediate 6 (120 mg, 0.326 mmol) and Intermediate 27 (164 mg, 0.424 mmol) were charged to a sealed tube with 1,4-dioxane (1 mL) and 1,2-dimethoxyethane (1 mL) and degassed. Aqueous sodium carbonate solution (2M, 0.815 mL, 1.63 mmol) was added, followed by Pd(PPh$_3$)$_4$ (19 mg, 0.016 mmol). The mixture was stirred at 90° C. for 3 h. Further Intermediate 27 (164 mg, 0.424 mmol) was added and the mixture was degassed, then further Pd(PPh$_3$)$_4$ (19 mg, 0.016 mmol) was added and the reaction mixture was stirred at 90° C. under nitrogen for 3 h. The mixture was diluted with water (10 mL) and washed with DCM (2×5 mL), then the aqueous layer was acidified to pH 1-2 by the addition of 1M aqueous HCl. The aqueous layer was extracted with DCM (3×10 mL). A brown residue, that dissolved in neither layer, was collected and purified by preparative HPLC, to afford the title compound (25 mg, 20%) as a white solid. $\delta_H$ (500 MHz, CD$_3$OD) 8.94 (s, 1H), 8.84 (s, 2H), 8.52 (s, 1H), 7.38-7.30 (m, 1H), 7.27-7.17 (m, 3H), 6.93 (t, J 74.0 Hz, 1H), 4.57 (d, J 13.3 Hz, 2H), 4.47 (s, 2H), 3.54-3.41 (m, 2H), 3.37 (s, 3H), 2.10-1.99 (m, 2H), 1.77 (d, J 13.2 Hz, 2H). Method D HPLC-MS: MH+ m/z 511, RT 2.41 minutes.

Example 28

(3S)-1-[5-(3-{[2-(Difluoromethoxy)phenyl]methyl}-2-methylimidazo[1,2-a]pyrazin-6-yl)pyrimidin-2-yl]piperidine-3-carboxylic acid (2-Chloropyrimidin-5-yl)boronic acid (65 mg, 0.41 mmol), (3S)-piperidine-3-carboxylic acid (56 mg, 0.431 mmol) and potassium carbonate (57 mg, 0.41 mmol) were charged to a sealed tube with DMF (2 mL) under nitrogen. The reaction mixture was stirred at 80° C. for 60 minutes. To the mixture were added Intermediate 6 (100 mg, 0.271 mmol), 1,4-dioxane (2 mL) and 2M aqueous sodium carbonate solution (0.16 mL, 1.231 mmol). The mixture was degassed, bis[3-(diphenylphosphanyl)cyclopenta-2,4-dien-1-yl]iron dichloropalladium dichloromethane complex (17 mg, 0.021 mmol) was added and the mixture was stirred at 80° C. under nitrogen for 6 h. The mixture was partitioned between DCM (20 mL) and water (10 mL), and the aqueous fraction was washed with DCM (10 mL). The aqueous layer was acidified to pH 1, then extracted with DCM (3×15 mL). The combined extracts were washed with brine (10 mL), dried over sodium sulfate and concentrated. The residue was purified by preparative HPLC to afford the title compound (30 mg, 15%) as a light brown solid. $\delta_H$ (500 MHz, DMSO-d$_6$) 8.98 (s, 1H), 8.94 (s, 2H), 8.78 (s, 1H), 7.44-7.10 (m, 5H), 4.78-4.70 (m, 1H), 4.52 (d, J 13.0 Hz, 1H), 4.42 (s, 2H), 3.18-3.10 (m, 1H), 3.05 (t, J 11.0 Hz, 1H), 2.44-2.35 (m, 1H), 2.34 (s, 3H), 2.01 (d, J 9.4 Hz, 1H), 1.79-1.59 (m, 2H), 1.44 (q, J 11.9 Hz, 1H). Method D HPLC-MS: MH+ m/z 495, RT 2.84 minutes.

Example 29

5-(3-{[2-(Difluoromethoxy)phenyl]methyl}-2-methylimidazo[1,2-a]pyrazin-6-yl)-2-[4-(1H-1,2,3,4-tetrazol-5-ylmethyl)piperazin-1-yl]pyrimidine formate Example 4 (132 mg, 0.29 mmol) and potassium carbonate (40 mg, 0.29 mmol were stirred in DMF (2 mL) for 10 minutes before the addition of 5-(chloromethyl)-1H-1,2,3,4-tetrazole (35 mg, 0.29 mmol) in two portions, 30 minutes apart. The mixture was stirred for 6 h at r.t., then allowed to stand over the weekend. The mixture was diluted with EtOAc, washed with water followed by brine, dried over magnesium sulfate and concentrated. The residue was purified by FCC, eluting with 10-50% MeOH in DCM. The resulting material was further purified by preparative HPLC to afford the title compound (20.9 mg, 13%). $\delta_H$ (250 MHz, DMSO-d$_6$) 8.97 (d, J 6.2 Hz, 3H), 8.79 (s, 1H), 7.57-6.95 (m, 6H), 4.42 (s, 2H), 3.97 (s, 2H), 3.84 (s, 4H), 2.58 (s, 4H), 2.33 (s, 3H). Method D HPLC-MS: MH+ m/z 534, RT 2.02 minutes.

Example 30

(3R)-1-[5-(3-{[2-(Difluoromethoxy)phenyl]methyl}-2-methylimidazo[1,2-a]pyrazin-6-yl)pyrimidin-2-yl]piperidine-3-carboxylic acid (2-Chloropyrimidin-5-yl)boronic acid (100 mg, 0.63 mmol) and (3R)-piperidine-3-carboxylic acid (82 mg, 0.63 mmol) were suspended in DMF (2 mL) and stirred for 2 h at 80° C. To the mixture were added Intermediate 6 (120 mg, 0.32 mmol), 2M aqueous potassium carbonate solution (0.48 mL) and 1,4-dioxane (3 mL). The mixture was degassed with nitrogen, then bis[3-(diphenylphosphanyl)cyclopenta-2,4-dien-1-yl]iron dichloropalladium dichloromethane complex (13 mg, 0.016 mmol) was added. The mixture was heated at 80° C. in a sealed tube for 15 h. The mixture was diluted with DCM (20 mL) and extracted with water (10 mL), followed by 2M aqueous potassium carbonate solution (10 mL). The combined aqueous layers were acidified to pH 4 by the addition of 6M hydrochloric acid. The mixture was left to stand for 10 minutes and the resultant precipitate was collected by filtration. The solids were washed with water (5 mL) and dried under vacuum, to afford the title compound (50.6 mg, 31%) as a brown solid. $\delta_H$ (500 MHz, DMSO-d$_6$) 12.33 (s, 1H), 8.96 (s, 1H), 8.94 (s, 2H), 8.78 (s, 1H), 7.41-7.12 (t, J 74.2 Hz, 1H), 7.31 (t, J 6.4 Hz, 1H), 7.22-7.13 (m, 3H), 4.72 (d, J 10.6 Hz, 1H), 4.50 (d, J 12.9 Hz, 1H), 4.39 (s, 2H), 3.17 (t, J 11.8 Hz, 1H), 3.07 (t, J 11.0 Hz, 1H), 2.41 (t, J 10.5 Hz, 1H), 2.34 (s, 3H), 2.01 (d, J 9.8 Hz, 1H), 1.68 (dt, J 23.0, 12.2 Hz, 2H), 1.44 (d, J 12.2 Hz, 1H). Method D HPLC-MS: MH+ m/z 495, RT 2.84 minutes.

Example 31

1-[5-(3-{1-[2-(Difluoromethoxy)phenyl]-1-hydroxyethyl}-2-methylimidazo[1,2-c]-pyrazin-6-yl)pyrimidin-2-yl]piperidine-4-carboxylic acid Intermediate 29 (85 mg, 0.15 mmol) was suspended in THF (3 mL), then 2M aqueous NaOH solution (0.77 mL)

was added and the mixture was heated at 80° C. for 7 h. The mixture was concentrated under reduced pressure and acidified with 1N aqueous HCl solution to pH 4-5. The mixture was extracted with 1:1 isopropanol/chloroform (2×25 mL) and the organic layer was washed with water (2×10 mL), then dried over sodium sulfate and concentrated under reduced pressure, to afford the title compound (68 mg, 76%) as a beige solid. $\delta_H$ (500 MHz, CD$_3$OD) 9.47 (s, 1H), 9.14 (s, 2H), 8.95 (s, 1H), 8.86 (dd, J 7.8, 1.6 Hz, 1H), 8.06 (t, J 7.4 Hz, 1H), 8.00 (td, J 7.9, 1.6 Hz, 1H), 7.66 (d, J 8.0 Hz, 1H), 7.11 (t, J 73.9 Hz, 1H), 5.34-5.20 (m, 2H), 3.83-3.67 (m, 2H), 3.31 (s, 3H), 3.25 (tt, J 11.0, 3.9 Hz, 1H), 2.77 (s, 3H), 2.60 (dd, J 13.4, 3.2 Hz, 2H), 2.25 (q, J 10.9 Hz, 2H), 1.90 (s, 1H). Method D HPLC-MS: MH+ m/z 524, RT 2.50 minutes.

Example 32

1-[5-(3-{1-[2-(Difluoromethoxy)phenyl]ethyl}-2-methylimidazo[1,2-a]pyrazin-6-yl)-pyrimidin-2-yl] piperidine-4-carboxylic acid formate Intermediate 31 (47% pure, 25 mg, 0.02 mmol) was suspended in THF (5 mL), then 2M aqueous NaOH solution (0.11 mL) was added and mixture was heated at 80° C. for 2 h. The mixture was concentrated under reduced pressure and acidified with 1N aqueous HCl solution to pH 3-4. The mixture was extracted with 1:1 isopropanol/chloroform (2×25 mL), concentrated under reduced pressure and purified by preparative HPLC, to afford the title compound (5.2 mg, 47%) as an off-white solid. $\delta_H$ (500 MHz, CD$_3$OD) 8.96-8.86 (m, 1H), 8.82 (s, 2H), 8.52 (s, 1H), 8.49 (s, 1H), 7.74-7.60 (m, 1H), 7.42-7.27 (m, 2H), 7.16 (d, J 7.7 Hz, 1H), 6.73 (t, J 74.0 Hz, 1H), 5.08 (q, J 7.3 Hz, 1H), 4.73 (d, J 13.4 Hz, 2H), 3.21-3.12 (m, 2H), 2.66-2.56 (m, 1H), 2.38 (s, 3H), 2.06-1.98 (m, 2H), 1.84 (d, J 7.4 Hz, 3H), 1.74-1.62 (m, 2H). Method D HPLC-MS: MH+ m/z 509, RT 2.83 minutes.

Example 33

1-[5-(3-{[2-(Difluoromethoxy)phenyl](methoxy) methyl}-2-methylimidazo[1,2-a]-pyrazin-6-yl)py-rimidin-2-yl]piperidine-4-carboxylic acid Intermediate 32 (63 mg, 0.158 mmol) and Intermediate 22 (79 mg, 0.208 mmol) were charged to a sealed tube with 1,4-dioxane (1 mL) and 1,2-dimethoxyethane (1 mL) and the mixture was degassed. Degassed 2M aqueous sodium carbonate solution (0.395 mL, 0.791 mmol) and Pd(PPh$_3$)$_4$ (9 mg, 0.01 mmol) were added and the reaction mixture was stirred under nitrogen at 90° C. for 3 h. Further Intermediate 22 (79 mg, 0.208 mmol) was added and the mixture was degassed. Degassed 2M aqueous sodium carbonate solution (0.395 mL, 0.791 mmol) and Pd(PPh$_3$)$_4$ (9 mg, 0.01 mmol) were then added and the reaction mixture was stirred under nitrogen at 90° C. for 3 h. Further Intermediate 22 (79 mg, 0.208 mmol) was added and the mixture was degassed. Degassed 2M aqueous sodium carbonate solution (0.395 mL, 0.791 mmol) and Pd(PPh$_3$)$_4$ (9 mg, 0.01 mmol) were then added and the reaction was stirred under nitrogen at 90° C. for 3 h. The mixture was diluted with DCM (15 mL) and water (10 mL), the organic layer was separated and the aqueous layer was washed with DCM (10 mL). The aqueous layer was adjusted to pH 1-2 by the addition of 0.5M aqueous HCl solution (10 mL), then extracted with DCM (3×10 mL). The combined organic layers were washed with brine (10 mL), dried over sodium sulfate and concentrated under vacuum. The residue was purified by preparative HPLC to afford the title compound (20 mg, 24%) as an off-white solid. $\delta_H$ (500 MHz, CDCl$_3$) 9.05 (d, J 1.1 Hz, 1H), 8.73 (s, 2H), 8.32 (d, J 1.2 Hz, 1H), 7.73 (dd, J 7.2, 2.0 Hz, 1H), 7.41-7.30 (m, 2H), 7.08 (d, J 7.6 Hz, 1H), 6.44 (t, J 73.7 Hz, 1H), 5.99 (s, 1H), 4.71 (d, J 13.5 Hz, 2H), 3.40 (s, 3H), 3.23-3.11 (m, 2H), 2.67 (m, 1H), 2.56 (s, 3H), 2.12-2.01 (m, 2H), 1.85-1.70 (m, 2H). Method D HPLC-MS: MH+ m/z 525, RT 3.00 minutes.

Example 34

1-[5-(3-{[2-(Difluoromethoxy)phenyl](methoxy) methyl}-2-methylimidazo[1,2-a]-pyrazin-6-yl)py-rimidin-2-yl]-1,4-diazepan-5-one A mixture of Intermediate 16 (90% pure, 120 mg, 0.46 mmol) and Intermediate 32 (200 mg, 0.5 mmol) was stirred in 1,4-dioxane (4 mL) and DMSO (0.5 mL) and the mixture was degassed with nitrogen. Aqueous potassium carbonate solution (2M, 800 iut) was added, followed by bis[3-(diphenylphosphanyl)cyclopenta-2,4-dien-1-yl]iron dichloropalladium dichloromethane complex (19 mg, 0.02 mmol), and the reaction mixture was heated at 100° C. for 4 h. EtOAc (10 mL) and water (5 mL) were added and the solution was stirred vigorously for 5 minutes. The aqueous layer was extracted with EtOAc, and the combined organic extracts were washed with water (10 mL) and brine (10 mL). The aqueous phase was further extracted with DCM (3×20 mL). The combined organic layers were dried over magnesium sulfate and concentrated under vacuum. The crude residue was purified by FCC, eluting with 0-6% (7M NH$_3$ in MeOH) in DCM, to afford the title compound (107 mg, 46%) as a cream solid. $\delta_H$ (500 MHz, CDCl$_3$) 9.13 (s, 1H), 8.77 (s, 2H), 8.38 (s, 1H), 7.75 (d, J 7.3 Hz, 1H), 7.37 (dq, J 15.0, 7.3, 6.6 Hz, 2H), 7.09 (d, J 7.7 Hz, 1H), 6.46 (t, J 73.6 Hz, 1H), 6.05 (s, 1H), 6.00 (s, 1H), 4.13 (d, J 5.6 Hz, 4H), 3.42 (s, 3H), 3.38 (t, J 6.5 Hz, 2H), 2.78-2.68 (m, 2H), 2.59 (s, 3H). Method D HPLC-MS: MH+ m/z 510, RT 2.61 minutes.

Example 35

1-[5-(3-{[2-(Difluoromethoxy)phenyl]methyl}-2-methylimidazo[1,2-a]pyrazin-6-yl)-pyrimidin-2-yl] pyrrolidine-3-carboxylic acid A mixture of (2-chloropyrimidin-5-yl)boronic acid (100 mg, 0.63 mmol) and 3-carboxypyrrolidin-1-ium trifluoroacetate (200 mg, 0.87 mmol) was heated under microwave irradiation at 100° C. for 1 h. Intermediate 6 (150 mg, 0.41 mmol), 2M sodium carbonate solution (0.65 mL) and 1,2-dimethoxyethane (4 mL) were added. The mixture was thoroughly degassed, then Pd(PPh$_3$)$_4$ (50 mg, 0.04 mmol) was added. The mixture was heated at 90° C. in a sealed tube under nitrogen for 2 h. The mixture was cooled to r.t., then diluted with DCM (20 mL) and saturated aqueous sodium bicarbonate solution (10 mL). The organic phase was separated, washed with brine, dried over sodium sulfate and concentrated under vacuum. The residue was purified by preparative HPLC to afford the title compound (8.9 mg, 5%) as a tan solid. $\delta_H$ (250 MHz, DMSO-d$_6$) 8.93 (d, J 1.2 Hz, 1H), 8.90 (s, 2H), 8.73 (s, 1H), 7.53-6.93 (m, 5H), 4.38 (s, 2H), 3.73-3.65 (m, 2H), 3.55 (q, J 6.9 Hz, 2H), 3.19-3.12 (m, 1H), 2.29 (s, 3H), 2.21-2.09 (m, 2H). Method D HPLC-MS: MH+ m/z 481, RT 2.44 minutes.

Example 36

2-{4-[5-(3-{[2-(Difluoromethoxy)phenyl]methyl}-2-methylimidazo[1,2-a]pyrazin-6-yl)-pyrimidin-2-yl]piperazin-1-yl}propanoic acid (2-Chloropyrimidin-5-yl)boronic acid (100 mg, 0.63 mmol) and 2-(piperazin-1-yl)propanoic acid (100 mg, 0.63 mmol) were dissolved in DMF (2 mL) and potassium carbonate (131 mg, 0.95 mmol) was added. The mixture was heated at 80° C. in a sealed tube for 6 h. To the mixture were added Intermediate 6 (150 mg, 0.41 mmol), 2M aqueous potassium carbonate solution (0.6 mL) and 1,4-dioxane (3 mL). The mixture was degassed with nitrogen, then bis[3-(diphenylphosphanyl)cyclopenta-2,4-dien-1-yl]-iron dichloropalladium dichloromethane complex (25 mg, 0.03 mmol) was added. The mixture was heated at 80° C. in a sealed tube for 4 h. The mixture was diluted with DCM (20 mL) and extracted with water (10 mL), followed by 2M aqueous potassium carbonate solution (10 mL). The combined aqueous layers were extracted with 1:1 isopropanol/chloroform (20 mL), then the organic layer was separated and concentrated under vacuum. The residue was purified by preparative HPLC to afford the title compound (43.8 mg, 21%). $\delta_H$ (500 MHz, DMSO-$d_6$) 8.97 (d, J 1.1 Hz, 1H), 8.94 (s, 2H), 8.78 (s, 1H), 7.33-7.29 (m, 1H), 7.26 (t, J 15 Hz, 1H), 7.18 (d, J 8.1 Hz, 1H), 7.16 (d, J 6.2 Hz, 2H), 4.41 (s, 2H), 3.79 (dt, J 14.1, 6.9 Hz, 4H), 3.24 (q, J 7.0 Hz, 1H), 2.65 (dt, J 16.1, 4.3 Hz, 4H), 2.32 (s, 3H), 1.19 (d, J 7.0 Hz, 3H). Method A HPLC-MS: MH+ m/z 524, RT 3.15 minutes.

Example 37

4-[5-(3-{[2-(Difluoromethoxy)phenyl](hydroxy)methyl}-2-methylimidazo[1,2-a]pyrazin-6-yl)pyrimidin-2-yl]piperazin-2-one A mixture of (2-chloropyrimidin-5-yl)boronic acid (100 mg, 0.63 mmol) and piperazin-2-one (63 mg, 0.632 mmol) was heated in 1,4-dioxane (2 mL) under microwave irradiation at 100° C. for 1 h. Intermediate 5 (160 mg, 0.417 mmol), 2M aqueous sodium carbonate solution (1.516 mL, 3.03 mmol) and 1,2-dimethoxyethane (1 mL) were added. The mixture was thoroughly degassed, then Pd(PPh$_3$)$_4$ (73 mg, 0.06 mmol) was added. The mixture was heated at 90° C. in a sealed tube under nitrogen for 8 h. The mixture was diluted with EtOAc (20 mL) and saturated aqueous sodium bicarbonate solution (10 mL). The organic phase was separated and washed with brine (10 mL), then dried over sodium sulfate and concentrated under vacuum. The residue was suspended in hot DMSO (2 mL), allowed to cool and filtered. The solids were washed with MeOH (2×2 mL), and the combined filtrates were purified preparative HPLC, to afford the title compound (10 mg, 3%) as a white solid. $\delta_H$ (500 MHz, DMSO-$d_6$) 8.98 (m, 3H), 8.91-8.85 (m, 1H), 8.15 (s, 1H), 8.04 (dd, J 5.7, 3.7 Hz, 1H), 7.38 (dt, J 7.4, 3.7 Hz, 2H), 7.23-6.88 (m, 2H), 6.55 (d, J 4.1 Hz, 1H), 6.34 (d, J 4.2 Hz, 1H), 4.25 (s, 2H), 4.05-3.90 (m, 2H), 3.31 (t, J 6.5 Hz, 2H), 2.19 (s, 3H). Method D HPLC-MS: MH+ m/z 482, RT 2.05 minutes.

Example 38

3-[5-(3-{[2-(Difluoromethoxy)phenyl]methyl}-2-methylimidazo[1,2-d]pyrazin-6-yl)-pyrimidin-2-yl]-3,6-diazabicyclo[3.2.2]nonan-7-one To a solution of Intermediate 33 (0.33 g, 0.815 mmol) were added Intermediate 6 (0.3 g, 0.81 mmol), 2M aqueous potassium carbonate solution (4.07 mL) and 1,4-dioxane (20 mL). The mixture was degassed with nitrogen for 15 minutes, then bis[3-(diphenylphosphanyl)cyclopenta-2,4-dien-1-yl]iron dichloropalladium dichloromethane complex (34 mg, 0.04 mmol) was added. The mixture was heated at 80° C. for 18 h. Upon cooling to r.t., the mixture was evaporated to dryness and the residue was purified by FCC, eluting with a gradient of 0-100% MeOH in DCM. The crude residue was triturated with hot MeOH, then the resulting precipitate was filtered and dried, to afford the title compound (47.3 mg, 10%) as an off-white solid. $\delta_H$ (500 MHz, DMSO-$d_6$) 8.97 (d, J 1.3 Hz, 1H), 8.94 (s, 2H), 8.78 (d, J 1.3 Hz, 1H), 8.10 (d, J 5.7 Hz, 1H), 7.42-7.09 (m, 5H), 4.89-4.81 (m, 2H), 4.41 (s, 2H), 3.68-3.61 (m, 1H), 3.29 (d, J 14.1 Hz, 1H), 3.22-3.16 (m, 1H), 2.61-2.55 (m, 1H), 2.32 (s, 3H), 1.81-1.57 (m, 4H). Method D HPLC-MS: MH+ m/z 506, RT 2.51 minutes.

Example 39

1-[5-(3-{[2-(Difluoromethoxy)phenyl]methyl}-2-methylimidazo[1,2-a]pyrazin-6-yl)-pyridin-2-yl]piperazine Intermediate 34 (35 mg, 0.06 mmol) was stirred in DCM (0.2 mL) and trifluoroacetic acid (0.2 mL) was added. The mixture was stirred at r.t. for 30 minutes, before being purified using a SCX cartridge, to afford the title compound (26.2 mg, 90%) as a pale yellow glassy solid. $\delta_H$ (250 MHz, CDCl$_3$) 8.99 (s, 1H), 8.54 (d, J 2.3 Hz, 1H), 8.03-7.92 (m, 2H), 7.26 (m, 1H), 7.19-7.05 (m, 2H), 6.94-6.33 (m, 3H), 4.31 (s, 2H), 3.62 (s, 4H), 3.03 (s, 4H), 2.54 (s, 3H). Method D HPLC-MS: MH+ m/z 451, RT 1.62 minutes.

Example 40

3-{[2-(Difluoromethoxy)phenyl]methyl}-6-(3,6-dihydro-2H-pyran-4-yl)-2-methyl-imidazo[1,2-a]pyrazine Intermediate 6 (200 mg, 0.54 mmol) and 2-(3,6-dihydro-2H-pyran-4-yl)-4,4,5,5-tetramethyl-1,3,2-dioxaborolane (170 mg, 0.81 mmol) were dissolved in 1,4-dioxane (5 mL) and 2M potassium carbonate in water (0.8 mL) was added. The mixture was flushed with nitrogen and bis[3-(diphenylphosphanyl)cyclopenta-2,4-dien-1-yl]iron dichloropalladium dichloromethane complex (20 mg, 0.02 mmol) was added. The mixture was heated at 90° C. for 16 h. The mixture was diluted with EtOAc (30 mL), then washed with water (2×10 mL) and brine (10 mL). The organic layer was dried over sodium sulfate and concentrated under vacuum. The resulting dark orange solid was purified by FCC, eluting with 0-100% EtOAc in heptanes followed by 0-10% MeOH in EtOAc, to afford the title compound (159 mg, 79%) as a peach solid. $\delta_H$ (250 MHz, CDCl$_3$) 8.87 (d, J 1.1 Hz, 1H), 7.62 (s, 1H), 7.17-7.01 (m, 3H), 6.93-6.29 (m, 3H), 4.32 (q, J 2.5 Hz, 2H), 4.24 (s, 2H), 3.88 (t, J 5.5 Hz, 2H), 2.50 (s, 3H), 2.43-2.32 (m, 2H). Method A HPLC-MS: MH+ m/z 372, RT 3.74 minutes.

Example 41

1-[4-(3-{[2-(Difluoromethoxy)phenyl]methyl}-2-methylimidazo[1,2-a]pyrazin-6-yl)-piperidin-1-yl]ethan-1-one Intermediate 35 (100 mg, 0.24 mmol) was dissolved in DCM (5 mL), then triethylamine (0.07 mL, 0.49 mmol) and acetic anhydride (23.12 µL, 0.24 mmol) were added at r.t. The mixture was stirred at r.t. for 2 h, then concentrated under reduced pressure and purified by preparative HPLC, to afford the title compound (56 mg, 55%) as a brown sticky solid. $\delta_H$ (500 MHz, CDCl$_3$) 9.04 (s, 1H), 7.60 (s, 1H), 7.34-7.27 (m, 1H), 7.22-7.08 (m, 2H), 6.93 (d, J 7.4 Hz, 1H), 6.62 (t, J 73.6 Hz, 1H), 4.78 (t, J 13.4 Hz, 1H), 4.27 (s, 2H), 3.94 (d, J 13.6 Hz, 1H), 3.80-3.60 (m, 1H), 3.18 (td, J 13.3, 2.5 Hz, 1H), 2.65 (td, J 13.1, 2.6 Hz, 1H), 2.56 (s, 3H), 2.12 (s, 3H), 2.07-1.99 (m, 1H), 1.92 (d, J 13.0 Hz, 1H), 1.67 (dtd, J 25.5, 12.6, 6.2 Hz, 2H). Method D HPLC-MS: MH+ m/z 415, RT 2.10 minutes.

Example 42

4-[5-(3-{[2-(Difluoromethoxy)phenyl]methyl}-2-methylimidazo[1,2-a]pyrazin-6-yl)-4-methylpyridin-2-yl]piperazin-2-one Intermediate 36 (100 mg, 0.25 mmol) was added to piperazin-2-one (75 mg, 0.75 mmol) in 1-methyl-2-pyrrolidinone (2.5 mL) in a microwave tube. The mixture was stirred at 200° C. under microwave irradiation for 1.5 h, then at 220° C. for 1 h. The mixture was purified using a SCX cartridge, then further purified by preparative HPLC, to afford the title compound (61.2 mg, 51%) as an off-white solid. $\delta_H$ (250 MHz, CDCl$_3$) 9.01 (s, 1H), 8.06 (s, 1H), 7.69 (d, J 1.2 Hz, 1H), 7.26 (s, 1H), 7.17-7.05 (m, 2H), 6.91-6.26 (m, 3H), 4.29 (s, 2H), 4.13 (s, 2H), 3.90 (t, J 5.1 Hz, 2H), 3.49 (br s, 2H), 2.54 (s, 3H), 2.28 (s, 3H). Method A HPLC-MS: MH+ m/z 479, RT 3.02 minutes.

Example 43

6-(3-{[2-(Difluoromethoxy)phenyl]methyl}-2-methylimidazo[1,2-a]pyrazin-6-yl)-2,3-dihydro-1H-indol-2-one A mixture of Intermediate 6 (300 mg, 0.81 mmol), (2-oxo-2,3-dihydro-1H-indol-6-yl)boronic acid (216.29 mg, 1.22 mmol) and 2M aqueous potassium carbonate solution (1.63 mL) in 1,4-dioxane (10 mL) was purged with nitrogen for 5 minutes, then bis[3-(diphenylphosphanyl)cyclopenta-2,4-dien-1-yl]iron dichloropalladium dichloromethane complex (33 mg, 0.04 mmol) was added and the mixture was heated at 100° C. for 3 h. The mixture was cooled to r.t., filtered through celite and concentrated under reduced pressure. The residue was purified by FCC, then recrystallized from MeOH, to afford the title compound (39 mg, 10%) as a beige solid. $\delta_H$ (500 MHz, DMSO-d$_6$) 10.54 (s, 1H), 8.98 (d, J 1.2 Hz, 1H), 8.76 (d, J 1.2 Hz, 1H), 7.58 (dd, J 7.8, 1.5 Hz, 1H), 7.50 (s, 1H), 7.42-7.27 (m, 2H), 7.27-7.08 (m, 4H), 4.45 (s, 2H), 3.52 (s, 2H), 2.34 (s, 3H). Method D HPLC-MS: MH+ m/z 421, RT 2.48 minutes.

Example 44

1-[5-(3-{[2-(Difluoromethoxy)phenyl]methyl}-2-methylimidazo[1,2-a]pyrazin-6-yl)-pyridin-2-yl]piperidine-4-carboxylic acid Intermediate 38 (38 mg, 0.07 mmol) was dissolved in ethanol (1.5 mL) and 2M aqueous potassium hydroxide solution (36.5 µL) was added. The reaction mixture was heated at 80° C. for 5 h, then heating was continued overnight. The cooled reaction mixture was filtered. A solid was collected, which was washed with ethanol (10 mL) and dried under vacuum to afford an off-white solid. The filtrate was evaporated to afford an off-white solid. This material was triturated with hot EtOAc to afford an off-white solid. All the solids and filtrate were combined and purified by preparative HPLC to afford the title compound (8.5 mg, 23%) as a white solid. $\delta_H$ (500 MHz, DMSO-d$_6$) 8.95 (s, 1H), 8.73 (d, J 2.3 Hz, 1H), 8.67 (s, 1H), 8.10 (dd, J 8.9, 2.4 Hz, 1H), 7.45-7.07 (m, 5H), 6.94 (d, J 9.0 Hz, 1H), 4.42 (s, 2H), 4.26 (d, J 13.3 Hz, 2H), 2.99 (t, J 11.2 Hz, 2H), 2.33 (s, 3H), 1.87 (d, J 10.7 Hz, 2H), 1.53 (q, J 11.2 Hz, 2H), plus one signal obscured by DMSO peak. Method D HPLC-MS: MH+ m/z 494, RT 2.10 minutes.

Example 45

Potassium 1-[5-(3-{[2-(difluoromethoxy)phenyl]methyl}-2-methylimidazo[1,2-a]pyrazin-6-yl)pyridin-2-yl]-4-methylpiperidine-4-carboxylate Intermediate 39 (65 mg, 0.08 mmol) was dissolved in ethanol (3 mL) and 2M aqueous potassium hydroxide solution (61 µL) was added. The reaction mixture was heated at 80° C. for 2 h. Further 2M aqueous potassium hydroxide solution (0.24 mL) was added and the reaction mixture was heated at 80° C. for 1.5 h. Further 2M aqueous potassium hydroxide solution (0.30 mL) was added and the reaction mixture was heated at 80° C. for 2 h. The cooled reaction mixture was acidified with 2M hydrochloric acid to pH 2. The mixture was partitioned between 1:10 isopropanol/chloroform (6 mL) and water (3 mL). The aqueous layer was separated and further extracted into 1:10 isopropanol/chloroform (2×6 mL). The combined organic extracts were washed with brine (6 mL), dried over sodium sulfate and evaporated, to give a yellow solid (55 mg). A second portion of Intermediate 39 (45 mg, 0.12 mmol) was hydrolysed using the foregoing procedure to afford a yellow solid (32 mg). The batches were dissolved in 1:10 isopropanol/chloroform (3 mL), combined and evaporated. The resulting yellow solid (82 mg) was dissolved in ethanol (5 mL), then 2M aqueous potassium hydroxide solution (79 iut) was added. The mixture was stirred at r.t. for 1 h, before being heated at 50° C. for 2 h, then at 80° C. for 2 h. The reaction mixture remained a suspension. The cooled mixture was evaporated, and the resulting solid was dissolved in a mixture of isopropanol (7 mL) and water (3 mL) by warming with a heat gun. The resultant solution was stirred at r.t. for 20 minutes, then evaporated, to afford the title compound (80 mg, 71%) as a yellow solid. $\delta_H$ (500 MHz, DMSO-d$_6$) 8.93 (d, J 1.3 Hz, 1H), 8.70 (d, J 2.5 Hz, 1H), 8.64 (d, J 1.2 Hz, 1H), 8.06 (dd, J 9.0, 2.5 Hz, 1H), 7.41-7.06 (m, 5H), 6.89 (d, J 9.1 Hz, 1H), 4.41 (s, 2H), 4.00-3.90 (m, 2H), 3.19-3.15 (m, 2H), 2.33 (s, 3H), 2.00 (d, J 13.2 Hz, 2H), 1.30-1.21 (m, 2H), 1.07 (s, 3H). Method D HPLC-MS: MH+ m/z 508, RT 2.27 minutes.

Example 46

3-[(2,5-Dichlorophenyl)methyl]-2-methyl-6-(1-methylpyrazol-4-yl)imidazo[1,2-a]-pyrazine A mixture of Intermediate 41 (183 mg, 0.47 mmol), iodine (119 mg, 0.47 mmol), phosphinic acid (0.1 mL) and acetic acid (2 mL) was heated at 100° C. for 2 h. To the cooled reaction mixture were added aqueous NaOH solution (2M) and DCM, then the organic layer was dried over magnesium sulfate and concentrated. The crude residue was purified by column chromatography (SiO$_2$, EtOAc:hexanes, 0 to 100%, then MeOH: EtOAc, 0 to 20%), then further purified by preparative HPLC, to afford the title compound (17 mg, 10%) as a white solid. $\delta_H$ (400 MHz, DMSO-d$_6$) 8.94 (d, J 0.9 Hz, 1H), 8.64 (d, J 0.8 Hz, 1H), 8.20 (s, 1H), 7.96 (s, 1H), 7.56 (d, J 8.5 Hz, 1H), 7.40 (dd, J 8.5, 2.4 Hz, 1H), 7.08 (d, J 2.4 Hz, 1H), 4.47 (2H, s), 3.89 (3H, s), 2.25 (3H, s). HPLC-MS: MH+ m/z 372, RT 2.15 minutes.

Example 47

3-[5-(3-{[2-(Difluoromethoxy)phenyl]methyl}-2-methylimidazo[1,2-d]pyrazin-6-yl)-pyrimidin-2-yl]-3-azabicyclo[4.1.0]heptane-6-carboxylic acid To a solution of Intermediate 43 (55.5 mg, 0.104 mmol) was added a 2M solution of potassium hydroxide in water (0.052 mL, 0.104 mmol) at r.t. The reaction mixture was stirred at 60° C. for 24 h and left standing at r.t. for 48 h. Further 2M solution of potassium hydroxide in water (0.052 mL, 0.104 mmol) was added and the reaction mixture was stirred at 60° C. for a further 24 h. The reaction mixture was cooled to r.t. and the mixture was concentrated to ~2 mL, then the resulting solid was filtered and washed with diethyl ether. The solid was dissolved in water/DMSO (~6 mL) by sonication and heating. The precipitated solid was discarded, and the filtrate was concentrated under vacuum to yield a solid which was triturated in DMSO/water. The resulting solid was filtered, washed with water and discarded. The new filtrate was washed with diethyl ether (2×2 mL). The aqueous extract was acidified to pH 5 using a 1M aqueous solution of HCl, then extracted with diethyl ether (1×2 mL) and isopropanol:chloroform (2×2 mL). The organic extracts were combined and evaporated. The resulting solid was further purified by trituration in EtOAc, to afford the title compound (11 mg, 19%) as a beige solid. $\delta_H$ (500 MHz, DMSO-d$_6$) 12.28 (s, 1H), 8.97 (d, J 1.2 Hz, 1H), 8.93 (s, 2H), 8.76 (d, J 1.2 Hz, 1H), 7.41-7.10 (m, 5H), 4.41 (s, 2H), 4.26 (dd, J 13.7, 2.3 Hz, 1H), 3.91 (dd, J 13.7, 4.7 Hz, 1H), 3.78 (dt, J 12.1, 5.8 Hz, 1H), 3.39 (ddd, J 13.6, 8.5, 5.4 Hz, 2H), 2.33 (s, 3H), 1.86-1.71 (m, 3H), 1.28 (dd, J 9.1, 4.2 Hz, 1H), 0.78-0.70 (m, 1H). Method D HPLC-MS: MH+ m/z 507, RT 2.80 minutes.

Example 48

2-[5-(3-{[2-(Difluoromethoxy)phenyl]methyl}-2-methylimidazo[1,2-a]pyrazin-6-yl)-pyrimidin-2-yl]propan-2-ol A mixture of Intermediate 6 (0.5 g, 1.36 mmol), 2-[5-(4,4,5,5-tetramethyl-1,3,2-dioxaborolan-2-yl)pyrimidin-2-yl]propan-2-ol (0.5 g, 1.89 mmol), [1,1'-bis(diphenyl-phosphino)ferrocene]dichloropalladium(II) dichloromethane complex (30 mg, 0.037 mmol) and 2M aqueous sodium carbonate solution (3 mL) in 1,4-dioxane (12 mL) was degassed and stirred at 110° C. for 2 h. The cooled reaction mixture was diluted with EtOAc and washed with brine. The organic layer was dried over magnesium sulfate andconcentrated under reduced pressure. The crude residue was purified by column chromatography (SiO$_2$, EtOAc:hexanes, 80 to 100%). The resulting material was triturated in diethyl ether, filtered, washed with diethyl ether and dried, to give the title compound (64 mg, 10%) as a beige solid. $\delta_H$ (400 MHz, DMSO-d$_6$) 9.37 (s, 2H), 9.09 (m, 2H), 7.26 (m, 5H), 5.15 (s, 1H), 4.47 (s, 2H), 2.35 (s, 3H), 1.55 (m, 6H). HPLC-MS: MH+ m/z 426, RT 1.99 minutes.

Example 49

(1R,4R)-4-[5-(3-{[2-(Difluoromethoxy)phenyl]methyl}-2-methylimidazo[1,2-a]pyrazin-6-yl)pyrimidin-2-yl]cyclohexane-1-carboxylic acid Intermediate 45 (158 mg, 0.3 mmol) was dissolved in ethanol (5 mL), sodium ethoxide (62 mg, 0.91 mmol) was added and the reaction mixture was heated at 70° C. for 18 h. Water (4 mL) was added, and the mixture was stirred at 70° C. for 22 h. A 6M aqueous solution of sodium hydroxide (0.25 mL) was added and the reaction was stirred for 2 h. The reaction mixture was allowed to cool, then diluted with a 1M aqueous solution of sodium hydroxide (10 mL) and washed with EtOAc (20 mL). The organic phase was discarded. The aqueous phase was acidified to pH 5 using 6M aqueous hydrogen chloride solution to give a cloudy solution, which was extracted with a mixture of 2-propanol/chloroform (3×20 mL). The organic extracts were combined, dried over sodium sulfate and concentrated. The crude residue was purified by preparative HPLC. The resulting material (30 mg) was dissolved in 1,4-dioxane (3 mL) and water (3 mL). A 1M aqueous solution of potassium hydroxide (70 μL) was added, and the mixture was sonicated until a solution was obtained. The solution was concentrated to dryness, water (1 mL) was added and the solution was dried, to afford the title compound (29 mg, 88%) as a white solid. $\delta_H$ (500 MHz, DMSO-d$_6$) 9.28 (s, 2H), 9.05 (s, 2H), 7.43-7.08 (m, 5H), 4.45 (s, 2H), 2.76 (tt, J 12.0, 3.5 Hz, 1H), 2.33 (s, 3H), 1.97-1.87 (m, 4H), 1.79-1.70 (m, 1H), 1.60-1.48 (m, 2H), 1.40-1.28 (m, 2H). Method A HPLC-MS: MH+ m/z 494, RT 2.82 minutes.

Example 50

5-(3-{[2-(Difluoromethoxy)phenyl]methyl}-2-methylimidazo[1,2-a]pyrazin-6-yl)-pyridine-2-carbonitrile Tetrakis(triphenylphosphine)palladium(O) (16 mg, 0.01 mmol) was added to a thoroughly degassed mixture of Intermediate 6 (50 mg, 0.14 mmol) and 5-(4,4,5,5-tetramethyl-1,3,2-dioxaborolan-2-yl)pyridine-2-carbonitrile (47 mg, 0.2 mmol) in 2M aqueous sodium carbonate solution (0.22 mL) and 1,2-dimethoxyethane (1.1 mL). The mixture was heated in a sealed tube at 90° C. under a nitrogen atmosphere for 2 h. The reaction mixture was allowed to cool to room temperature and diluted with DCM (10 mL). The mixture was washed with saturated aqueous sodium bicarbonate solution (10 mL) and brine, then dried over sodium sulphate and concentrated under vacuum. The residue was purified by FCC, eluting with a 0-2% gradient of methanol in DCM. The crude product was further purified by preparative HPLC, to afford the title compound (24 mg, 45%) as an off-white solid. $\delta_H$ (250 MHz, CDCl$_3$) 9.18-9.05 (m, 2H), 8.40 (dd, J 8.2, 2.3 Hz, 1H), 8.32 (d, J 1.4 Hz, 1H), 7.78 (dd, J 8.2, 0.7 Hz, 1H), 7.36-7.27 (m, 1H), 7.22-7.09 (m, 2H), 7.01 (dd, J 7.6, 1.5 Hz, 1H), 6.66 (t, J 73.5 Hz, 1H), 4.37 (s, 2H), 2.61 (s, 3H). Method D HPLC-MS: MH+ m/z 392, RT 3.13 minutes.

Example 51

5-(3-{[2-(Difluoromethoxy)phenyl]methyl}-2-methylimidazo[1,2-d]pyrazin-6-yl)-pyridine-3-carbonitrile Tetrakis(triphenylphosphine)palladium(O) (31.4 mg, 0.03 mmol) was added to a thoroughly degassed mixture of Intermediate 6 (100 mg, 0.27 mmol) and (5-cyano-pyridin-3-yl)boronic acid (60.27 mg, 0.41 mmol) in a 2M solution of sodium carbonate in water (0.65 mL) and 1,2-dimethoxyethane (3.3 mL). The mixture was heated in a sealed tube at 90° C. overnight under a nitrogen atmosphere. The reaction mixture was allowed to cool to room temperature and diluted with dichloromethane (20 mL). The mixture was washed with a saturated aqueous solution of sodium bicarbonate (20 mL) and brine, then dried over sodium sulfate, filtered and concentrated in vacuo. The resulting crude mixture was purified by preparative HPLC to afford the title compound (8 mg, 6%) as a pale yellow solid. $\delta_H$ (250 MHz, CDCl$_3$) 9.21 (d, J 2.2 Hz, 1H), 9.06 (d, J 1.4 Hz, 1H), 8.86 (d, J 2.0 Hz, 1H), 8.54 (t, J 2.1 Hz, 1H), 8.27 (d, J 1.4 Hz, 1H), 7.36-7.27 (m, 1H), 7.22-7.09 (m, 2H), 7.04-6.35 (m, 2H), 4.36 (s, 2H), 2.59 (s, 3H). Method D HPLC-MS: MH+ m/z 392, RT 2.98 minutes.

Example 52

1-[4-(3-{[2-(Difluoromethoxy)phenyl]methyl}-2-methylimidazo[1,2-a]pyrazin-6-yl)-1,2,3,6-tetrahydropyridin-1-yl]ethan-1-one Triethylamine (0.07 mL, 0.49 mmol) and acetic anhydride (23.23 μL, 0.25 mmol) were added to a suspension of Intermediate 46 (100 mg, 0.25 mmol) in dichloromethane (5 mL) at room temperature. The mixture was stirred at room temperature for 2 h, then concentrated under reduced pressure. The crude residue was purified by preparative HPLC (Method C) to afford the title compound (55.5 mg, 55%) as a brown oil. $\delta_H$ (500 MHz, CDCl$_3$) 8.96 (s, 1H), 7.69 (d, J 10.4 Hz, 1H), 7.27 (d, J 14.4 Hz, 1H), 7.19-7.07 (m, 2H), 6.94 (t, J 8.5 Hz, 1H), 6.82-6.42 (m, 2H), 4.28 (d, J 5.8 Hz, 3H), 4.18 (d, J 2.8 Hz, 1H), 3.82 (t, J 5.7 Hz, 1H), 3.66 (t, J 5.7 Hz, 1H), 2.56 (d, J 1.8 Hz, 3H), 2.54 (s, 1H), 2.41 (s, 1H), 2.15 (d, J 19.0 Hz, 3H). Method D HPLC-MS: MH+ m/z 413, RT 2.31 minutes.

Example 53

4-(3-{[2-(Difluoromethoxy)phenyl]methyl}-2-methylimidazo[1,2-a]pyrazin-6-yl)-1-(methanesulfonyl)piperidine Intermediate 35 (100 mg, 0.24 mmol) was suspended in dichloromethane (3 mL) at room temperature and triethylamine (0.07 mL, 0.49 mmol) was added, followed by methanesulfonic anhydride (42.6 mg, 0.24 mmol). The mixture was stirred for 2 h, then concentrated under reduced pressure. The residue was purified by HPLC (Method C) to afford the title compound (83 mg, 75%) as a beige solid. $\delta_H$ (500 MHz, CDCl$_3$) 9.04 (s, 1H), 7.62 (s, 1H), 7.31 (t, J 7.8 Hz, 1H), 7.14 (dd, J 16.7, 8.2 Hz, 2H), 6.95 (d, J 7.5 Hz, 1H), 6.63 (t, J 73.6 Hz, 1H), 4.28 (s, 2H), 3.94 (d, J 12.0 Hz, 2H), 3.85-3.56 (m, 1H), 2.82 (d, J 6.0 Hz, 5H), 2.57 (s, 3H), 2.08 (d, J 12.3 Hz, 2H), 1.81 (qd, J 12.5, 4.0 Hz, 2H). Method D HPLC-MS: MH+ m/z 451, RT 2.35 minutes.

Example 54

3-(3-{[2-(Difluoromethoxy)phenyl]methyl}-2-methylimidazo[1,2-a]pyrazin-6-yl)-8-(methanesulfonyl)-8-azabicyclo[3.2.1]oct-2-ene Intermediate 47 (80% purity, 110 mg, 0.2 mmol) was stirred in dichloromethane (5 mL) and triethylamine (42 μL, 0.3 mmol) was added. After cooling to 0° C., methanesulfonyl chloride (47 μL, 0.61 mmol) was added slowly. The reaction mixture was allowed to warm slowly to room temperature and stirred for 2 h. The reaction mixture was washed with water (5 mL), saturated sodium bicarbonate solution (10 mL) and brine (10 mL). The organic phase was dried over sodium sulfate and concentrated. The crude yellow oil was purified by chromatography on silica (Biotage, 10 g cartridge), eluting with 0 to 50% dichloromethane in a 10% methanol solution in dichloromethane, to afford the title compound (62 mg, 64%) as a dark orange oil. $\delta_H$ (500 MHz, CDCl$_3$) 8.90 (s, 1H), 7.66 (s, 1H), 7.28 (dd, J 13.9, 6.1 Hz, 1H), 7.16 (d, J 8.2 Hz, 1H), 7.12 (t, J 7.5 Hz, 1H), 7.05 (d, J 5.5 Hz, 1H), 6.64 (t, J 73.6 Hz, 1H), 4.52 (q, J 6.3 Hz, 2H), 4.27 (s, 2H), 2.97 (dd, J 16.7, 4.0 Hz, 1H), 2.91 (s, 3H), 2.54 (s, 3H), 2.35-2.24 (m, 2H), 2.17 (ddd, J 17.8, 11.8, 6.3 Hz, 1H), 2.12-1.98 (m, 2H), 1.77-1.68 (m, 1H). Method D HPLC-MS: MH+ m/z 475, RT 2.73 minutes.

Example 55

4-[5-(3-{[2-(Difluoromethoxy)phenyl]methyl}-2-methylimidazo[1,2-a]pyrazin-6-yl)-1,3-thiazol-2-yl]morpholine Intermediate 6 (150 mg, 0.41 mmol) and 4-[5-(4,4,5,5-tetramethyl-1,3,2-dioxaborolan-2-yl)-1,3-thiazol-2-yl]morpholine (180 mg, 0.61 mmol) were dissolved in 1,4-dioxane (3 mL) and a 2M solution of potassium carbonate in water (0.6 mL) was added. The mixture was flushed with nitrogen, then Pd(dppf)Cl$_2$ complex with dichloromethane (30 mg, 0.04 mmol) was added. The mixture was heated at 90° C. for 16 h, then at 100° C. for 4 h. The mixture was diluted with ethyl acetate (20 mL), then washed with water (2×10 mL) and brine (10 mL). The organic layer was dried over magnesium sulfate and concentrated under vacuum. The resulting dark green crude solid was successively purified by chromatography on silica, eluting with 0 to 100% ethyl acetate in heptane and 0 to 10% methanol in ethyl acetate, then by preparative HPLC (Method A), to afford the title compound (45 mg, 24%) as an off-white solid. $\delta_H$ (250 MHz, CDCl$_3$) 8.90 (d, J 1.3 Hz, 1H), 7.91 (d, J 1.3 Hz, 1H), 7.49 (s, 1H), 7.26 (s, 1H), 7.19-7.06 (m, 2H), 6.98-6.33 (m, 2H), 4.28 (s, 2H), 3.89-3.74 (m, 4H), 3.58-3.44 (m, 4H), 2.53 (s, 3H). Method A HPLC-MS: MH+ m/z 458, RT 3.81 minutes.

Example 56

3-{[2-(Difluoromethoxy)phenyl]methyl}-6-(3,6-dihydro-2H-thiopyran-4-yl)-2-methyl-imidazo[1,2-a]pyrazine Intermediate 6 (50 mg, 0.136 mmol), 2-(3,6-dihydro-2H-thiopyran-4-yl)-4,4,5,5-tetramethyl-1,3,2-dioxaborolane (46.07 mg, 0.2 mmol) and a 2M solution of sodium bicarbonate in water (0.43 mL) were combined in 1,2-dimethoxyethane (2.2 mL) and the mixture was degassed thoroughly under nitrogen. Tetrakis(triphenylphosphine)-palladium(0) (16 mg, 0.014 mmol) was added and the mixture was heated at 90° C. in a sealed tube for 2 h. The reaction mixture was cooled to room temperature and diluted using dichloromethane (10 mL). The mixture was washed using an aqueous saturated solution of sodium bicarbonate (2×5 mL) and brine (10 mL). The organic phase was dried over sodium sulfate and concentrated in vacuo. The crude orange oil was purified by chromatography on silica (Biotage, 10 g cartridge), eluting with 0 to 100% ethyl acetate in heptane, to afford the title compound (23.5 mg, 45%) as a yellow solid. $\delta_H$ (500 MHz, CDCl$_3$) 8.94 (s, 1H), 7.74-7.66 (m, 1H), 7.32-7.27 (m, 1H), 7.16 (d, J 8.1 Hz, 1H), 7.11 (t, J 7.5 Hz, 1H), 6.93-6.89 (m, 1H), 6.88 (t, J 4.4 Hz, 1H), 6.63 (t, J 73.6 Hz, 1H), 4.28 (s, 2H), 3.39 (dd, J 12.7, 10.5 Hz, 2H), 2.88 (t, J 5.8 Hz, 2H), 2.69-2.61 (m, 2H), 2.55 (s, 3H). Method D HPLC-MS: MH+ m/z 388, RT 3.06 minutes.

Example 57

6-Bromo-3-[2-(difluoromethoxy)benzyl]-2-methyl-imidazo[1,2-a]pyrazine

See Intermediate 6.

Examples 58 & 59

1-[5-(3-{[2-(Difluoromethoxy)phenyl](methoxy)methyl}-2-methylimidazo[1,2-a]-pyrazin-6-yl)pyrimidin-2-yl]-1,4-diazepan-5-one (Isomers A and B)

Example 34 (96 mg) was separated into its component enantiomers using SFC on Chiralcel OD-H, eluting with 12% isopropanol: 88% CO$_2$, to afford Isomer A (40.5 mg) as a pale solid and Isomer B (37.9 mg) as a pale solid.

Isomer A (Example 58): $\delta_H$ (250 MHz, CDCl$_3$) 9.06 (s, 1H), 8.77 (s, 2H), 8.36 (s, 1H), 7.74 (m, 1H), 7.35 (m, 2H), 7.09 (d, J 8.7 Hz, 1H), 6.46 (t, J 73.6 Hz, 1H), 6.25 (s, 1H), 6.00 (s, 1H), 4.13 (m, 4H), 3.42 (s, 3H), 3.39 (m, 2H), 2.72 (m, 2H), 2.57 (s, 3H).

Isomer B (Example 59): $\delta_H$ (250 MHz, CDCl$_3$) 9.06 (s, 1H), 8.76 (s, 2H), 8.36 (s, 1H), 7.73 (m, 1H), 7.35 (m, 2H), 7.09 (d, J 8.7 Hz, 1H), 6.45 (t, J 73.6 Hz, 1H), 6.25 (s, 1H), 6.00 (s, 1H), 4.12 (m, 4H), 3.41 (s, 3H), 3.38 (m, 2H), 2.72 (m, 2H), 2.57 (s, 3H).

Examples 60 & 61

4-[5-(3-{[2-(Difluoromethoxy)phenyl](hydroxy)methyl}-2-methylimidazo[1,2-a]pyrazin-6-yl)pyrimidin-2-yl]piperazin-2-one (Isomers A and B)

Example 37 (130 mg) was separated into its component enantiomers using HPLC on Chiralcel OD-H 25 cm, eluting with MeOH+0.1% diethylamine, to afford Isomer A (10 mg) as a light brown solid and Isomer B (12 mg) as a light brown solid.

Isomer A (Example 60): $\delta_H$ (500 MHz, DMSO-d$_6$) 8.98 (m, 3H), 8.89 (s, 1H), 8.15 (s, 1H), 8.05 (dd, J 5.6, 3.8 Hz, 1H), 7.41-7.35 (m, 2H), 7.23-6.91 (m, 2H), 6.55 (s, 1H), 4.25 (s, 2H), 4.01-3.95 (m, 2H), 3.16 (s, 2H), 2.19 (s, 3H).

Isomer B (Example 61): $\delta_H$ (500 MHz, DMSO-d$_6$) 8.98 (m, 3H), 8.89 (s, 1H), 8.15 (s, 1H), 8.05 (dd, J 5.7, 3.7 Hz, 1H), 7.41-7.35 (m, 2H), 7.22-6.90 (m, 2H), 6.55 (s, 1H), 4.25 (s, 2H), 4.01-3.95 (m, 2H), 3.16 (s, 2H), 2.19 (s, 3H).

Example 62

[2-(Difluoromethoxy)phenyl]{2-methyl-6-[6-(piperazin-1-yl)pyridin-3-yl]imidazo[1,2-a]-pyrazin-3-yl}methanol (Isomer B)

Example 16 (150 mg) was separated into its component enantiomers using HPLC on Chiralcel OD-H 25 cm, eluting with 15% EtOH:85% heptanes+0.1% diethylamine, to afford the title compound (36 mg) as a light brown solid. $\delta_H$ (500 MHz, acetone-d$_6$) 8.85 (d, J 1.3 Hz, 1H), 8.67 (dd, J 10.2, 1.8 Hz, 2H), 8.15 (dd, J 7.0, 2.1 Hz, 1H), 8.06 (dd, J 8.9, 2.5 Hz, 1H), 7.41 (ddt, J 10.6, 7.3, 3.3 Hz, 2H), 7.17 (d, J 8.0 Hz, 1H), 7.05-6.71 (m, 2H), 6.67 (s, 1H), 3.59-3.50 (m, 4H), 2.93-2.84 (m, 4H+ water), 2.34 (s, 3H).

Example 63

Ethyl (1R,5S,6r)-3-(5-{3-[2-(difluoromethoxy)benzyl]-2-methylimidazo[1,2-a]pyrazin-6-yl}pyrimidin-2-yl)-3-azabicyclo[3.1.0]hexane-6-carboxylate See Intermediate 25.

Example 64

4-(3-{[2-(Difluoromethoxy)phenyl]methyl}-2-methylimidazo[1,2-a]pyrazin-6-yl)-1-(methanesulfonyl)-1,2,3,6-tetrahydropyridine Intermediate 46 (100 mg, 0.25 mmol) was suspended in DCM (3 mL) at room temperature, then triethylamine (0.07 mL, 0.49 mmol) was added, followed by methanesulfonic anhydride (43 mg, 0.25 mmol). The mixture was stirred for 2 h, then concentrated under reduced pressure and purified by HPLC (Method C), to afford the title compound (52 mg, 47%) as an off white solid. $\delta_H$ (250 MHz, CDCl$_3$) 8.93 (s, 1H), 7.71 (s, 1H), 7.26 (s, 1H), 7.19-7.05 (m, 2H), 6.94 (d, J 7.6 Hz, 1H), 6.82-6.40 (m, 2H), 4.28 (s, 2H), 4.00 (d, J 2.9 Hz, 2H), 3.52 (t, J 5.7 Hz, 2H), 2.84 (s, 3H), 2.60-2.56 (m, 2H), 2.55 (s, 3H). Method D HPLC-MS: MH+ m/z 449, RT 2.60 minutes.

The invention claimed is:
1. A compound of formula (IIA) or an N-oxide thereof, or a pharmaceutically acceptable salt thereof,

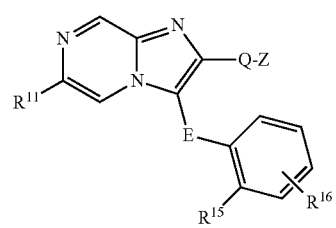

(IIA)

wherein
E represents —CH$_2$—, —CH(OH)—, —CH(OCH$_3$)—, —CH(CH$_3$)— or —C(CH$_3$)(OH)—;
Q represents a covalent bond; or Q represents —O—, —S—, —S(O)$_2$—, —N(R$^5$)—, —C(O)N(R$^5$)—, —N(R$^5$)C(O)—, —S(O)$_2$N(R$^5$)— or —N(R$^5$)S(O)$_2$—; or Q represents an optionally substituted straight or branched C$_{1-6}$ alkylene chain optionally comprising one, two or three heteroatom-containing linkages independently selected from —O—, —S—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—, wherein each optional substituent is independently halogen, trifluoromethyl, hydroxy, C$_{1-6}$ alkoxy or amino;
Z represents hydrogen, halogen or trifluoromethyl; or Z represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups is optionally substituted by one, two, or three substituents; or Z represents —Z$^1$—Z$^2$ or —$Z^1$—C(O)—$Z^2$, either of which moieties is optionally substituted by one, two, or three substituents, wherein each optional substituent is independently halogen, cyano, nitro, $C_{1-6}$ alkyl, trifluoromethyl, oxo, hydroxy, hydroxy($C_{1-6}$)alkyl, $C_{1-6}$ alkoxy, difluoromethoxy, trifluoromethoxy, $C_{1-3}$ alkylenedioxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylamino-carbonyl, aminosulfonyl, $C_{1-6}$ alkylaminosulfonyl, di($C_{1-6}$) alkylaminosulfonyl, aminocarbonylamino or hydrazinocarbonyl;

$Z^1$ represents a divalent radical derived from an aryl, $C_{3-7}$ heterocycloalkyl or heteroaryl group;

$Z^2$ represents aryl, $C_{3-7}$ heterocycloalkyl, $C_{3-7}$ heterocycloalkenyl or heteroaryl;

$R^5$ represents hydrogen or $C_{1-6}$ alkyl;

represents halogen or cyano; or $C_{1-6}$ alkyl, aryl, $C_{3-7}$ heterocycloalkyl, $C_{3-7}$ heterocycloalkenyl, $(C_{4-9})$heterobicycloalkenyl, heteroaryl, $(C_{3-7})$heterocycloalkyl$(C_{1-6})$-alkyl-aryl-, heteroaryl-$(C_{3-7})$heterocycloalkyl-, $(C_{3-7})$ cycloalkylheteroaryl-, $(C_{4-7})$cycloalkenyl-heteroaryl-, $(C_{3-7})$heterocycloalkyl-heteroaryl-, $(C_{3-7})$heterocycloalkyl-$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups is optionally substituted by one, two, or three substituents, wherein the optional substituents are independently halogen, cyano, cyano$(C_{1-6})$alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy$(C_{1-6})$alkyl, $C_{1-6}$ alkyl-thio, $C_{1-6}$ alkylsulfonyl, $(C_{1-6})$alkylsulfonyl$(C_{1-6})$alkyl, oxo, amino, $C_{1-6}$ alkylamino, di($C_{1-6}$)alkylamino, $(C_{1-6})$alkoxy$(C_{1-6})$alkylamino, N—[$(C_{1-6})$alkyl]-N-[hydroxy$(C_{1-6})$alkyl]-amino, $C_{2-6}$ alkylcarbonylamino, $C_{2-6}$ alkoxycarbonylamino, $C_{1-6}$ alkylaminocarbonylamino, $C_{1-6}$ alkylsulfonylamino, formyl, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, tetrazolyl, aminocarbonyl, $C_{1-6}$ alkylaminocarbonyl, di($C_{1-6}$)alkylaminocarbonyl, $C_{1-6}$ alkylsulfonylaminocarbonyl, aminosulfonyl, $C_{1-6}$ alkylaminosulfonyl and di($C_{1-6}$)alkylaminosulfonyl, difluoromethyl, difluoroethyl, hydroxy$(C_{1-6})$alkyl, $C_{1-6}$ alkylsulfinyl, hydroxy$(C_{1-6})$alkylamino, [$(C_{1-6})$alkoxy](hydroxy)$(C_{1-6})$alkylamino, [$(C_{1-6})$alkylthio]-(hydroxy)$(C_{1-6})$ alkylamino, di($C_{1-6}$)alkylamino$(C_{1-6})$alkylamino, N-[di($C_{1-6}$)alkylamino-$(C_{1-6})$alkyl]-N-[hydroxy$(C_{1-6})$alkyl]amino, hydroxy$(C_{1-6})$alkyl$(C_{3-7})$cycloalkylamino, (hydroxy)[$(C_{3-7})$cycloalkyl$(C_{1-6})$alkyl]amino, $(C_{3-7})$heterocycloalkylamino, $(C_{3-7})$-heterocycloalkyl$(C_{1-6})$alkylamino, oxo$(C_{3-7})$heterocycloalkyl$(C_{1-6})$alkylamino, $(C_{1-6})$alkyl-heteroarylamino, heteroaryl$(C_{1-6})$alkylamino, $(C_{1-6})$alkylheteroaryl$(C_{1-6})$alkylamino, N—[$(C_{1-6})$alkyl]-N—[$(C_{2-6})$alkylcarboyl]amino, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, N-[carboxy$(C_{1-6})$-alkyl]-N—[$(C_{1-6})$alkyl]amino, $C_{2-6}$ alkoxycarbonyl$(C_{1-6})$ alkylamino, N—[$(C_{1-6})$-alkyl]-N—[$(C_{1-6})$ alkylsulfonyl]amino, $(C_{3-7})$cycloalkylcarbonyl, phenylcarbonyl, tetrazolyl$(C_{1-6})$-alkyl, aminocarbonyl$(C_{1-6})$ alkyl or hydroxy$(C_{1-6})$alkylaminocarbonyl; and $R^{15}$ and $R^{16}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$) alkylaminocarbonyl, aminosulfonyl, $C_{1-6}$ alkylaminosulfonyl or di($C_{1-6}$)alkylaminosulfonyl.

2. A compound as claimed in claim 1 represented by formula (IIB) or an N-oxide thereof, or a pharmaceutically acceptable salt thereof,

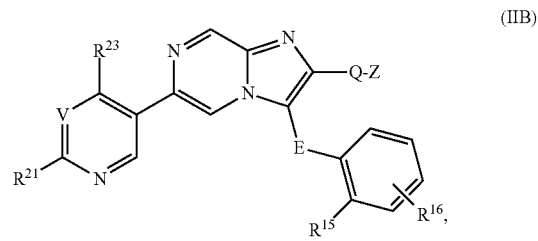

wherein

V represents C—$R^{22}$ or N;

$R^{21}$ represents hydrogen, halogen, halo($C_{1-6}$)alkyl, cyano, $C_{1-6}$ alkyl, trifluoromethyl, $C_{2-6}$ alkenyl, $C_{2-6}$ alkynyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulfonyl, amino, amino($C_{1-6}$)alkyl, $C_{1-6}$ alkylamino, di($C_{1-6}$)alkylamino, $(C_{1-6})$alkoxy$(C_{1-6})$alkylamino, N—[$(C_{1-6})$alkyl]-N-[hydroxy$(C_{1-6})$alkyl]amino, $(C_{3-7})$heterocycloalkylamino, $C_{2-6}$ alkylcarbonylamino, $(C_{2-6})$alkylcarbonylamino$(C_{1-6})$alkyl, $C_{2-6}$ alkoxycarbonylamino, $C_{1-6}$ alkylsulfonylamino, $(C_{1-6})$alkylsulfonylamino$(C_{1-6})$alkyl, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylamino-sulfonyl; or $R^{21}$ represents $(C_{3-7})$cycloalkyl, $(C_{4-7})$cycloalkenyl, $(C_{3-7})$heterocycloalkyl, $(C_{3-7})$heterocycloalkenyl, $(C_{4-9})$heterobicycloalkyl or $(C_{4-9})$spiroheterocycloalkyl, any of which groups is optionally substituted by one, two, or three substituents, wherein the optional substituents are independently halogen, cyano, cyano($C_{1-6}$)alkyl, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-6}$ alkylthio, $C_{1-6}$ alkylsulfonyl, $(C_{1-6})$alkyl-sulfonyl($C_{1-6}$)alkyl, oxo, amino, $C_{1-6}$ alkylamino, di($C_{1-6}$)alkylamino, $C_{2-6}$ alkylcarbonyl-amino, $C_{2-6}$ alkoxycarbonylamino, $C_{1-6}$ alkylsulfonylamino, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl, aminocarbonyl, $C_{1-6}$ alkylaminocarbonyl, di($C_{1-6}$)alkylaminocarbonyl, $C_{1-6}$ alkylsulfonylaminocarbonyl, aminosulfonyl, $C_{1-6}$ alkylaminosulfonyl and di($C_{1-6}$)alkylaminosulfonyl, tetrazolyl($C_{1-6}$)alkyl or aminocarbonyl($C_{1-6}$)alkyl;

$R^{22}$ represents hydrogen, halogen, cyano or $C_{1-6}$ alkyl; and $R^{23}$ represents hydrogen or $C_{1-6}$ alkyl.

3. A compound as claimed in claim 2 represented by formula (IIC), formula (IID) or formula (IIE) or an N-oxide thereof, or a pharmaceutically acceptable salt thereof, (IIC)
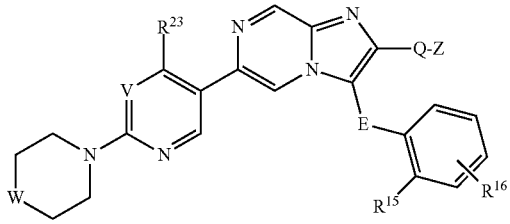

(IID)
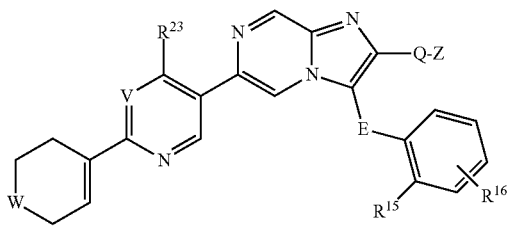

(IIE)
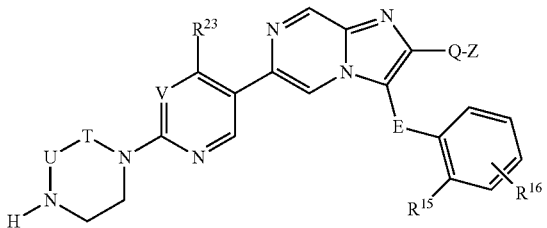

wherein
T represents —CH$_2$— or —CH$_2$CH$_2$—;
U represents C(O) or S(O)$_2$;
W represents O, S, S(O), S(O)$_2$, N(R$^{31}$) or C(R$^{32}$)(R$^{33}$);
R$^{31}$ represents hydrogen, cyano(C$_{1-6}$)alkyl, C$_{1-6}$ alkyl, trifluoromethyl, trifluoroethyl, C$_{1-6}$ alkylsulfonyl, (C$_{1-6}$)alkylsulfonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, tetrazolyl(C$_{1-6}$) alkyl, aminocarbonyl, aminocarbonyl(C$_{1-6}$)alkyl, C$_{1-6}$ alkylaminocarbonyl, di(C$_{1-6}$) alkylaminocarbonyl, aminosulfonyl, C$_{1-6}$ alkylaminosulfonyl or di(C$_{1-6}$) alkylaminosulfonyl;
R$^{32}$ represents halogen, C$_{1-6}$ alkoxy, carboxy, carboxy (C$_{1-6}$)alkyl, C$_{2-6}$ alkoxycarbonyl, C$_{2-6}$ alkoxycarbonyl (C$_{1-6}$)alkyl, tetrazolyl or aminocarbonyl; and
R$^{33}$ represents hydrogen, halogen, C$_{1-6}$ alkyl, hydroxy or amino.

4. A compound as claimed in claim 2 represented by formula (IIF) or formula (IIG) or an N-oxide thereof, or a pharmaceutically acceptable salt thereof, (IIF)
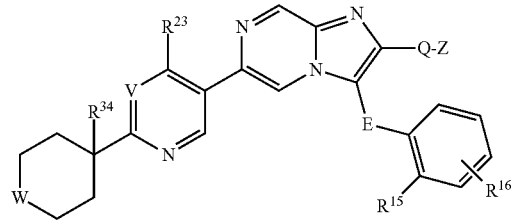

(IIG)
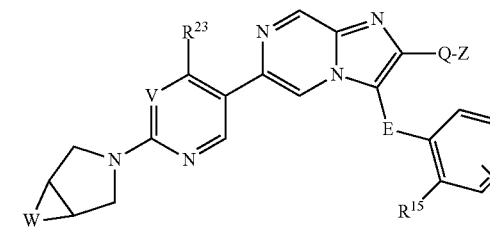

wherein
R$^{34}$ represents hydrogen, halogen, hydroxy, C$_{1-6}$ alkoxy, C$_{1-6}$ alkylthio, C$_{1-6}$ alkylsulfinyl, C$_{1-6}$ alkylsulfonyl, amino, C$_{1-6}$ alkylamino or di(C$_{1-6}$)alkylamino; and
W represents O, S, S(O), S(O)$_2$, N(R$^{31}$) or C(R$^{32}$)(R$^{33}$).

5. A compound as claimed in claim 4 or an N-oxide thereof, or a pharmaceutically acceptable salt thereof, wherein R$^{34}$ represents hydrogen or hydroxy.

6. A compound as claimed in claim 2 or an N-oxide thereof, or a pharmaceutically acceptable salt thereof, wherein R$^{21}$ represents hydroxy(C$_{1-6}$)alkyl.

7. A compound as claimed in claim 1 or an N-oxide thereof, or a pharmaceutically acceptable salt thereof, wherein E represents —CH$_2$— or —CH(CH$_3$)—.

8. A compound as claimed in claim 7 or an N-oxide thereof, or a pharmaceutically acceptable salt thereof, wherein R$^{15}$ represents difluoromethoxy.

9. A compound as claimed in claim 1 or an N-oxide thereof, or a pharmaceutically acceptable salt thereof, wherein R$^{11}$ represents heteroaryl or (C$_{3-7}$)heterocycloalkyl-heteroaryl-, either of which groups is optionally substituted by one, two, or three substituents.

10. A compound as claimed in claim 1 or an N-oxide thereof, or a pharmaceutically acceptable salt thereof, wherein R$^{15}$ represents difluoromethoxy.

11. A compound as claimed in claim 1, wherein the compound is
5-[3-(2,5-Dichlorobenzyl)-2-methylimidazo[1,2-a]pyrazin-6-yl]-1H-pyridin-2-one,
[2-(Difluoromethoxy)phenyl][6-(6-methoxypyridin-3-yl)-2-methylimidazo[1,2-a]pyrazin-3-yl]methanol,
5-{3-[2-(Difluoromethoxy)benzyl]-2-methylimidazo[1,2-a]pyrazin-6-yl}-2-methoxy-pyridine,
5-{3-[2-(Difluoromethoxy)benzyl]-2-methylimidazo[1,2-a]pyrazin-6-yl}-2-(piperazin-1-yl)pyrimidine,
5-{3-[2-(Difluoromethoxy)benzyl]-2-methylimidazo[1,2-a]pyrazin-6-yl}pyridin-2(1H)-one,
4-(5-{3-[2-(Difluoromethoxy)benzyl]-2-methylimidazo[1,2-a]pyrazin-6-yl}pyrimidin-2-yl)piperazin-2-one,
1-(5-{3-[2-(Difluoromethoxy)benzyl]-2-methylimidazo[1,2-a]pyrazin-6-yl}pyrimidin-2-yl)-1,4-diazepan-5-one,
tert-Butyl 4-(3-{[2-(difluoromethoxy)phenyl]methyl}-2-methylimidazo[1,2-a]pyrazin-6-yl)-1,2,3,6-tetrahydropyridine-1-carboxylate, tert-Butyl 4-(3-{[2-(difluoromethoxy)phenyl]methyl}-2-methylimidazo[1,2-a]pyrazin-6-yl)piperidine-1-carboxylate,
4-(3-{[2-(Difluoromethoxy)phenyl]methyl}-2-methyl-imidazo[1,2-a]pyrazin-6-yl)-benzene-1-sulfonamide,
4-[5-(3-{[2-(Difluoromethoxy)phenyl]methyl}-2-methylimidazo[1,2-a]pyrazin-6-yl)-pyridin-2-yl]morpholine,
5-(3-{[2-(Difluoromethoxy)phenyl]methyl}-2-methylimidazo[1,2-a]pyrazin-6-yl)-2-[4-(methanesulfonyl)piperazin-1-yl]pyrimidine,
tert-Butyl 3-(3-{[2-(difluoromethoxy)phenyl]methyl}-2-methylimidazo[1,2-a]pyrazin-6-yl)-8-azabicyclo[3.2.1]oct-2-ene-8-carboxylate,
2-{4-[5-(3-{[2-(Difluoromethoxy)phenyl]methyl}-2-methylimidazo[1,2-a]pyrazin-6-yl)-pyrimidin-2-yl]piperazin-1-yl}acetic acid, formate salt,
2-{4-[5-(3-{[2-(Difluoromethoxy)phenyl]methyl}-2-methylimidazo[1,2-a]pyrazin-6-yl)-pyrimidin-2-yl]piperazin-1-yl}acetamide,
[2-(Difluoromethoxy)phenyl]{2-methyl-6-[6-(piperazin-1-yl)pyridin-3-yl]imidazo[1,2-a]-pyrazin-3-yl}methanol,
5-(3-{[2-(Difluoromethoxy)phenyl]methyl}-2-methyl-imidazo[1,2-a]pyrazin-6-yl)-N-(oxolan-3-yl)pyrimidin-2-amine,
5-(3-{[2-(Difluoromethoxy)phenyl]methyl}-2-methyl-imidazo[1,2-a]pyrazin-6-yl)-2-(4,4-difluoropiperidin-1-yl)pyrimidine,
6-[5-(3-{[2-(Difluoromethoxy)phenyl]methyl}-2-methylimidazo[1,2-a]pyrazin-6-yl)-pyrimidin-2-yl]-2-oxa-6-azaspiro[3.3]heptane,
4-[5-(3-{[2-(Difluoromethoxy)phenyl]methyl}-2-methylimidazo[1,2-a]pyrazin-6-yl)-pyrimidin-2-yl]-2,6-dimethylmorpholine,
1-[5-(3-{[2-(Difluoromethoxy)phenyl]methyl}-2-methylimidazo[1,2-a]pyrazin-6-yl)-pyrimidin-2-yl]piperidine-4-carboxylic acid,
(1R,5S,6r)-3-(5-{3-[2-(Difluoromethoxy)benzyl]-2-methylimidazo[1,2-a]pyrazin-6-yl}-pyrimidin-2-yl)-3-azabicyclo[3.1.0]hexane-6-carboxylic acid,
Ethyl 1-[5-(3-{[2-(difluoromethoxy)phenyl]methyl}-2-methylimidazo[1,2-a]pyrazin-6-yl)pyrimidin-2-yl]-4-methylpiperidine-4-carboxylate,
1-[5-(3-{[2-(Difluoromethoxy)phenyl]methyl}-2-methylimidazo[1,2-a]pyrazin-6-yl)-pyrimidin-2-yl]-4-methylpiperidine-4-carboxylic acid,
5-(3-{[2-(Difluoromethoxy)phenyl]methyl}-2-methyl-imidazo[1,2-a]pyrazin-6-yl)-2-(3-methoxypyrrolidin-1-yl)pyrimidine,
2-[5-(3-{[2-(Difluoromethoxy)phenyl]methyl}-2-methylimidazo[1,2-a]pyrazin-6-yl)-pyrimidin-2-yl]-2-azaspiro[3.3]heptane-6-carboxylic acid,
1-[5-(3-{[2-(Difluoromethoxy)phenyl]methyl}-2-methylimidazo[1,2-a]pyrazin-6-yl)-pyrimidin-2-yl]-4-hydroxypiperidine-4-carboxylic acid,
(3S)-1-[5-(3-{[2-(Difluoromethoxy)phenyl]methyl}-2-methylimidazo[1,2-a]pyrazin-6-yl)pyrimidin-2-yl]piperidine-3-carboxylic acid,
5-(3-{[2-(Difluoromethoxy)phenyl]methyl}-2-methyl-imidazo[1,2-a]pyrazin-6-yl)-2-[4-(1H-1,2,3,4-tetrazol-5-ylmethyl)piperazin-1-yl]pyrimidine formate,
(3R)-1-[5-(3-{[2-(Difluoromethoxy)phenyl]methyl}-2-methylimidazo[1,2-a]pyrazin-6-yl)pyrimidin-2-yl]piperidine-3-carboxylic acid,
1-[5-(3-{1-[2-(Difluoromethoxy)phenyl]-1-hydroxy-ethyl}-2-methylimidazo[1,2-a]-pyrazin-6-yl)pyrimidin-2-yl]piperidine-4-carboxylic acid,
1-[5-(3-{1-[2-(Difluoromethoxy)phenyl]ethyl}-2-methylimidazo[1,2-a]pyrazin-6-yl)-pyrimidin-2-yl]piperidine-4-carboxylic acid formate,
1-[5-(3-{[2-(Difluoromethoxy)phenyl](methoxy)methyl}-2-methylimidazo[1,2-a]-pyrazin-6-yl)pyrimidin-2-yl]piperidine-4-carboxylic acid,
1-[5-(3-{[2-(Difluoromethoxy)phenyl](methoxy)methyl}-2-methylimidazo[1,2-a]-pyrazin-6-yl)pyrimidin-2-yl]-1,4-diazepan-5-one,
1-[5-(3-{[2-(Difluoromethoxy)phenyl]methyl}-2-methylimidazo[1,2-a]pyrazin-6-yl)-pyrimidin-2-yl]pyrrolidine-3-carboxylic acid,
2-{4-[5-(3-{[2-(Difluoromethoxy)phenyl]methyl}-2-methylimidazo[1,2-a]pyrazin-6-yl)-pyrimidin-2-yl]piperazin-1-yl}propanoic acid,
4-[5-(3-{[2-(Difluoromethoxy)phenyl](hydroxy)methyl}-2-methylimidazo[1,2-a]pyrazin-6-yl)pyrimidin-2-yl]piperazin-2-one,
3-[5-(3-{[2-(Difluoromethoxy)phenyl]methyl}-2-methylimidazo[1,2-a]pyrazin-6-yl)-pyrimidin-2-yl]-3,6-diazabicyclo[3.2.2]nonan-7-one,
1-[5-(3-{[2-(Difluoromethoxy)phenyl]methyl}-2-methylimidazo[1,2-a]pyrazin-6-yl)-pyridin-2-yl]piperazine,
3-{[2-(Difluoromethoxy)phenyl]methyl}-6-(3,6-dihydro-2H-pyran-4-yl)-2-methyl-imidazo[1,2-a]pyrazine,
1-[4-(3-{[2-(Difluoromethoxy)phenyl]methyl}-2-methylimidazo[1,2-a]pyrazin-6-yl)-piperidin-1-yl]ethan-1-one,
4-[5-(3-{[2-(Difluoromethoxy)phenyl]methyl}-2-methylimidazo[1,2-a]pyrazin-6-yl)-4-methylpyridin-2-yl]piperazin-2-one,
6-(3-{[2-(Difluoromethoxy)phenyl]methyl}-2-methyl-imidazo[1,2-a]pyrazin-6-yl)-2,3-dihydro-1H-indol-2-one,
1-[5-(3-{[2-(Difluoromethoxy)phenyl]methyl}-2-methylimidazo[1,2-a]pyrazin-6-yl)-pyridin-2-yl]piperidine-4-carboxylic acid,
Potassium 1-[5-(3-{[2-(difluoromethoxy)phenyl]methyl}-2-methylimidazo[1,2-a]pyrazin-6-yl)pyridin-2-yl]-4-methylpiperidine-4-carboxylate,
3-[(2,5-Dichlorophenyl)methyl]-2-methyl-6-(1-methyl-pyrazol-4-yl)imidazo[1,2-a]-pyrazine,
3-[5-(3-{[2-(Difluoromethoxy)phenyl]methyl}-2-methylimidazo[1,2-a]pyrazin-6-yl)-pyrimidin-2-yl]-3-azabicyclo[4.1.0]heptane-6-carboxylic acid,
2-[5-(3-{[2-(Difluoromethoxy)phenyl]methyl}-2-methylimidazo[1,2-a]pyrazin-6-yl)-pyrimidin-2-yl]propan-2-ol,
(1R,4R)-4-[5-(3-{[2-(Difluoromethoxy)phenyl]methyl}-2-methylimidazo[1,2-a]pyrazin-6-yl)pyrimidin-2-yl]cyclohexane-1-carboxylic acid,
5-(3-{[2-(Difluoromethoxy)phenyl]methyl}-2-methyl-imidazo[1,2-a]pyrazin-6-yl)-pyridine-2-carbonitrile,
5-(3-{[2-(Difluoromethoxy)phenyl]methyl}-2-methyl-imidazo[1,2-a]pyrazin-6-yl)-pyridine-3-carbonitrile,
1-[4-(3-{[2-(Difluoromethoxy)phenyl]methyl}-2-methylimidazo[1,2-a]pyrazin-6-yl)-1,2,3,6-tetrahydropyridin-1-yl]ethan-1-one,
4-(3-{[2-(Difluoromethoxy)phenyl]methyl}-2-methyl-imidazo[1,2-a]pyrazin-6-yl)-1-(methanesulfonyl)piperidine,
3-(3-{[2-(Difluoromethoxy)phenyl]methyl}-2-methyl-imidazo[1,2-a]pyrazin-6-yl)-8-(methanesulfonyl)-8-azabicyclo[3.2.1]oct-2-ene, 4-[5-(3-{[2-(Difluoromethoxy)phenyl]methyl}-2-methylimidazo[1,2-a]pyrazin-6-yl)-1,3-thiazol-2-yl]morpholine, 3-{[2-(Difluoromethoxy)phenyl]methyl}-6-(3,6-dihydro-2H-thiopyran-4-yl)-2-methylimidazo[1,2-a]pyrazine, 6-Bromo-3-[2-(difluoromethoxy)benzyl]-2-methylimidazo[1,2-a]pyrazine, 1-[5-(3-{[2-(Difluoromethoxy)phenyl](methoxy)methyl}-2-methylimidazo[1,2-a]-pyrazin-6-yl)pyrimidin-2-yl]-1,4-diazepan-5-one, 4-[5-(3-{[2-(Difluoromethoxy)phenyl](hydroxy)methyl}-2-methylimidazo[1,2-a]pyrazin-6-yl)pyrimidin-2-yl]piperazin-2-one, Ethyl (1R,5S,6r)-3-(5-{3-[2-(difluoromethoxy)benzyl]-2-methylimidazo[1,2-a]pyrazin-6-yl}pyrimidin-2-yl)-3-azabicyclo[3.1.0]hexane-6-carboxylate, or 4-(3-{[2-Difluoromethoxy)phenyl]methyl}-2-methylimidazo[1,2-a]pyrazin-6-yl)-1-(methanesulfonyl)-1,2,3,6-tetrahydropyridine, or an N-oxide thereof, or a pharmaceutically acceptable salt.

12. A pharmaceutical composition comprising a compound of formula (IIA) as defined in claim 1 or an N-oxide thereof, or a pharmaceutically acceptable salt thereof, in association with a pharmaceutically acceptable carrier.

13. A pharmaceutical composition as claimed in claim 12 further comprising an additional pharmaceutically active ingredient.

14. A method for modulating tumor necrosis factor α activity in a patient, which method comprises administering to a patient in need of such modulation an effective amount of a compound of formula (IIA) according to claim 1 or an N-oxide thereof, or a pharmaceutically acceptable salt thereof.

* * * * *